United States Patent
Specht et al.

(12) 
(10) Patent No.: US 6,620,923 B1
(45) Date of Patent: Sep. 16, 2003

(54) HUMAN NUCLEIC ACID SEQUENCES FROM ENDOMETRIAL TUMOR TISSUE

(75) Inventors: Thomas Specht, Berlin (DE); Bernd Hinzmann, Berlin (DE); Armin Schmitt, Berlin (DE); Christian Pilarsky, Schonfeld-Weissig (DE); Edgar Dahl, Potsdam (DE); André Rosenthal, Berlin (DE)

(73) Assignee: Metagen Pharmaceuticals GmbH, Berlin (DE)

( * ) Notice: Subject to any disclaimer, the term of this patent is extended or adjusted under 35 U.S.C. 154(b) by 0 days.

(21) Appl. No.: 09/673,395

(22) PCT Filed: Apr. 15, 1999

(86) PCT No.: PCT/DE99/01174

§ 371 (c)(1),
(2), (4) Date: Dec. 27, 2000

(87) PCT Pub. No.: WO99/54461

PCT Pub. Date: Oct. 28, 1999

(30) Foreign Application Priority Data

Apr. 17, 1998 (DE) .......................................... 198 17 948

(51) Int. Cl.[7] .............................. C07H 21/04; C12Q 1/68
(52) U.S. Cl. .................. 536/23.1; 536/25.3; 536/24.31; 536/24.3; 435/6
(58) Field of Search .............................. 536/23.1, 25.3, 536/24.31, 24.3; 530/350

(56) References Cited

U.S. PATENT DOCUMENTS 6,174,992 B1 * 1/2001 Ni et al. ...................... 530/324

FOREIGN PATENT DOCUMENTS

WO    WO 97/34997    * 9/1997 ............. C12Q/1/20

OTHER PUBLICATIONS

Genbank Accession No. AF071219, "Homo sapiens mRNA for lipophilin C." Nov. 26, 1998.*
Genbank Accession No. AJ224173, "Homo sapiens mammaglobin B precursor, mRNA." Mar. 25, 1999.*
Adams M.D. et al.: "EST41316 Endometrial tumor Homo sapiens cDNA 5' end." EMBL Accession No. AA336687, Apr. 18, 1997, XP002127129.

Mahmood Manavi, M.D. et al.: "Amplification and expression of the c–erbB–2 oncogene in Muellerian–derived Genital–tract tumors." Gynecologic Oncology, Bd. 71, Nr. 2, Nov. 1998, Seiten 165–171, XP002127134.

M.F. Arlt et al.: "Frequent deletion of chromosome 1p sequences in an aggressive histologic subtype of endometrial cancer." Human Molecular Genetics, Bd. 5, Nr. 7, 1996, Seiten 1017–1021, XP002127133.

To Hoa Thai et al.: "Mutations in the BRCA1–associated RING domain (BARD1) gene in primary breast, ovarian and uterine cancers." Human Molecular Genetics, Bd. 7, Nr. 2, 1998, Seiten 195–202, XP002127132.

E. Strunck et al.: "Basement membrane regulates gen expression in HEC1B(L) Endometrial adenocarcinoma cells." Biochemical and Biophysical Research Communications., Bd. 221, Nr. 2, 1996, Seiten 346–350, XP002127131.

Adams M.D. et al.: "EST41427 Endometrial tumor Homo sapiens cDNA 5' end." EMBL Accession No. AA336787, Apr. 18, 1997, XP002127130.

Mahmood Manavi, M.D. et al.: "Amplification and expression of the c–erbB–2 oncogene in Muellerian–derived Genital–tract tumors." Gynecologic Oncology, Bd. 71, Nr. 2, Nov. 1998, Seiten 165–171, XP002127134.

M. Sakata et al.: "Messenger RNA differential display reverse–transcriptase–polymerase–chain–reaction analysis of a progestogen–suppressive gene in a human endometrial–cancer cell line." International Journal of Cancer, Bd. 78, Nr. 1, Sep. 25, 1998, Seiten 125–129, XP002127136.

A. Koul et al.: "A somatic BRCA2 mutation in RER+ endometrial carcinomas that specifically deletes the amino- –terminal transactivation domain" Genes, Chromosomes & Cancer, Bd. 24, Nr. 3, Mar. 1999, Seiten 207–212, XP002127135.

* cited by examiner

Primary Examiner—Gary Benzion
Assistant Examiner—Jeanine Goldberg
(74) Attorney, Agent, or Firm—Millen, White, Zelano & Branigan, P.C.

(57) ABSTRACT

Human nucleic acid sequences—mRNA, cDNA, genomic sequences—from endometrial tumor tissue, which code for gene products or portions thereof, and their use, are described. In addition, the polypeptides that can be obtained by way of the sequences and their use are described.

1 Claim, 10 Drawing Sheets

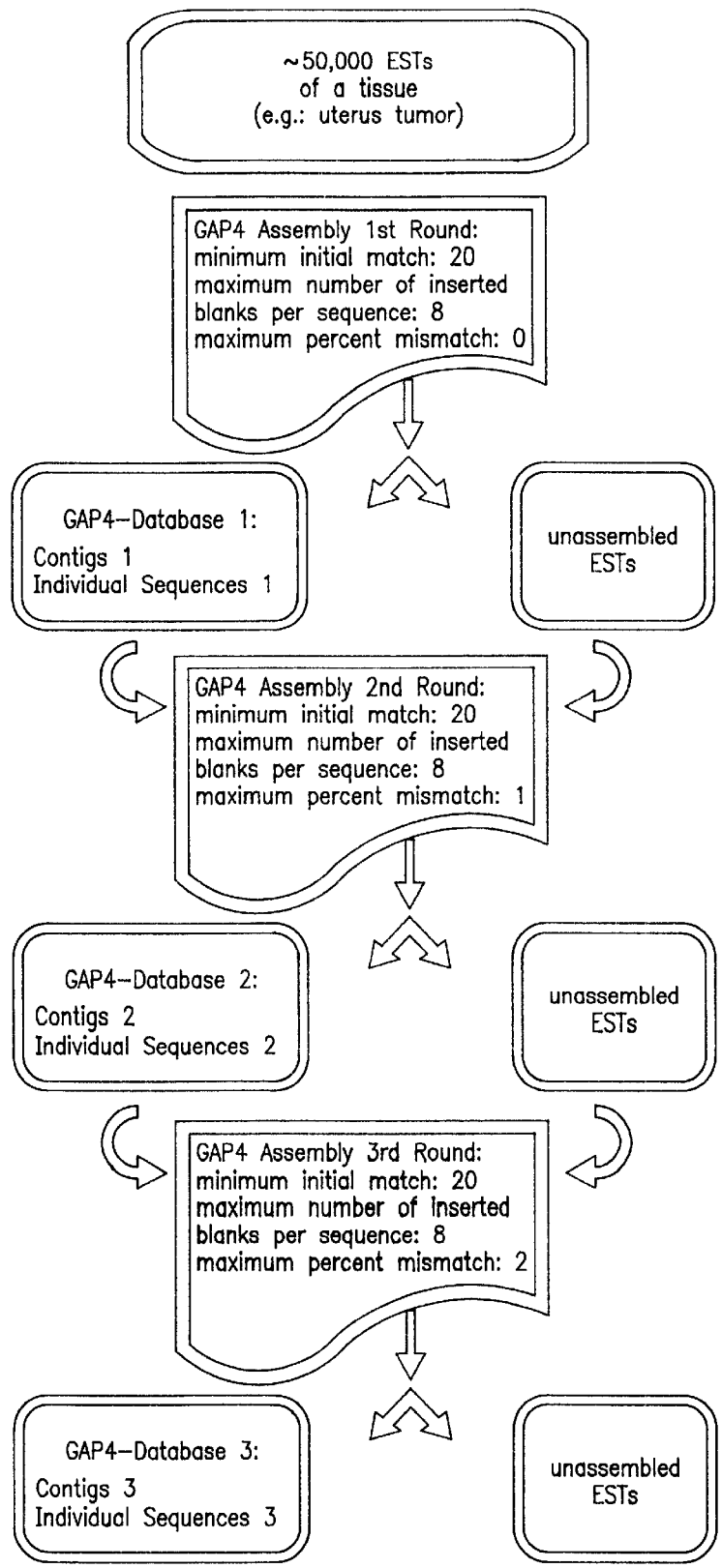
FIG. 2b-I

HUMAN NUCLEIC ACID SEQUENCES FROM ENDOMETRIAL TUMOR TISSUE

The invention relates to human nucleic acid sequences from endometrial tumors, which code for gene products or portions thereof, their functional genes that code at least one bioactive polypeptide and their use.

In addition, the invention relates to the polypeptides that can be obtained by way of the sequences and their use.

One of the main causes of death by cancer in women is the endometrial tumor, for control of which new therapies are necessary. Previously used therapies, such as, e.g., chemotherapy, hormone therapy or surgical removal of tumor tissue, frequently do not result in a complete cure.

The cancer phenomenon often goes along with overexpression or underexpression of certain genes in degenerated cells, it still being unclear whether these altered expression rates are the cause or the result of the malignant transformation. Identification of these genes would be an important step for development of new therapies against cancer. Spontaneous formation of cancer is often preceded by a host of mutations. They can have the most varied effects on the expression pattern in the affected tissue, such as, e.g., underexpression or overexpression, but also expression of shortened genes. Several such changes due to these mutation cascades can ultimately lead to malignant degeneration. The complexity of these relationships makes an experimental approach very difficult.

A database that consists of so-called ESTs is used to look for candidate genes, i.e., genes that compared to the tumor tissue are more strongly expressed in normal tissue. ESTs (expressed sequence tags) are sequences of cDNAs, i.e., mRNAs transcribed in reverse, therefore molecules that reflect gene expression. The EST sequences are determined for normal and degenerated tissue. These databases are offered to some extent commercially by various companies. The ESTs of the LifeSeq database, which is used here, are generally between 150 and 350 nucleotides long. They represent a pattern that is unmistakable for a certain gene, although this gene is normally very much longer (>2000 nucleotides). By comparison of the expression patterns of normal and tumor tissue, ESTs can be identified that are important for tumor formation and proliferation. There is, however, the following problem: Since the EST sequences that are found can belong to different regions of an unknown gene due to different constructions of cDNA libraries, in this case a completely incorrect ratio of the occurrence of these ESTs in the respective tissue would arise. This would only be noticed when the complete gene is known and thus ESTs can be assigned to the same gene.

It has now been found that this possibility of error can be reduced if all ESTs from the respective tissue type are assembled beforehand, before the expression patterns are compared to one another. Overlapping ESTs of the same gene were thus combined into longer sequences (see FIG. 1, FIG. 2a and FIG. 3). This lengthening and thus coverage of an essentially larger gene region in each of the respective bases are intended to largely avoid the above-described error. Since there were no existing software products for this purpose, programs for assembling genomic sections were employed, which were used modified and to which our own programs were added. A flow chart of the assembly procedure is shown in FIGS. 2b1–2b4.

Nucleic acid sequences Seq. ID No. 1 to Seq. ID No. 141 and Seq. ID Nos. 531–552, 554, and 555, which play a role as candidate genes in endometrial tumors, have now been found.

Nucleic acid sequences Seq. ID Nos. 1–126 and Seq. ID Nos. 531–552, 554, and 555 are of special interest.

The invention thus relates to nucleic acid sequences that code a gene product or a portion thereof, comprising a) a nucleic acid sequence selected from the group of nucleic acid sequences Seq. ID Nos. 1–126 and Seq. ID Nos. 531–552, 554, and 555, b) an allelic variation of the nucleic acid sequences named under a) or c) a nucleic acid sequence that is complementary to the nucleic acid sequences named under a) or b).

In addition, the invention relates to a nucleic acid sequence according to one of the sequences Seq. ID Nos. 1–126 or a complementary or allelic variant thereof and the nucleic acid sequences thereof, which have 90% to 95% homology to a human nucleic acid sequence.

The invention also relates to nucleic acid sequences Seq. ID No. 1 to Seq. ID No. 141 and Seq. ID Nos. 531–552, 554, and 555, which are expressed elevated in the endometrial tumor.

The invention further relates to nucleic acid sequences comprising a portion of the above-mentioned nucleic acid sequences in such a sufficient amount that they hybridize with sequences Seq. ID Nos. 1–126 and Seq. ID Nos. 531–552, 554, and 555.

The nucleic acid sequences according to the invention generally have a length of at least 50 to 4500 bp, preferably a length of at least 150 to 4000 bp, especially a length of 450 to 3500 bp.

With the partial sequences Seq. ID Nos. 1–126 and Seq. ID Nos. 531–552, 554, and 555 according to the invention, expression cassettes can also be built using current process practice, whereby on the cassette at least one of the nucleic acid sequences according to the invention is combined with at least one control or regulatory sequence generally known to one skilled in the art, such as, e.g., a suitable promoter. The sequences according to the invention can be inserted in a sense or antisense orientation.

A large number of expression cassettes or vectors and promoters which can be used are known in the literature.

Expression cassettes or vectors are defined as: 1. bacterial, such as, e.g., phagescript, pBs, φX174, pBluescript SK, pBs KS, pNH8a, pNH16a, pNH18a, pNH46a (Stratagene), pTrc99A, pKK223-3, pKK233-3, pDR540, pRIT5 (Pharmacia), 2. eukaryotic, such as, e.g., pWLneo, pSV2cat, pOG44, pXT1, pSG (Stratagene), pSVK3, pBPV, pMSG, pSVL (Pharmacia).

Control or regulatory sequences are defined as suitable promoters. Here, two preferred vectors are the pKK232-8 and the PCM7 vector. In particular, the following promoters are intended: lacI, lacZ, T3, T7, gpt, lambda $P_R$, trc, CMV, HSV thymidine-kinase, SV40, LTRs from retrovirus and mouse metallothionein-I.

The DNA sequences located on the expression cassette can code a fusion protein which comprises a known protein and a bioactive polypeptide fragment.

The expression cassettes are likewise the subject matter of this invention.

The nucleic acid fragments according to the invention can be used to produce full-length genes. The genes that can be obtained are likewise the subject matter of this invention.

The invention also relates to the use of the nucleic acid sequences according to the invention and the gene fragments that can be obtained from use.

The nucleic acid sequences according to the invention can be moved with suitable vectors into host cells, in which as the heterologous part, the genetic information which is contained on the nucleic acid fragments and which is expressed is located.

The host cells containing the nucleic acid fragments are likewise the subject matter of this invention.

Suitable host cells are, e.g., prokaryotic cell systems such as E. coli or eukaryotic cell systems such as animal or human cells or yeasts.

The nucleic acid sequences according to the invention can be used in the sense or antisense form.

Production of polypeptides or their fragments is done by cultivation of the host cells according to current cultivation methods and subsequent isolation and purification of the peptides or fragments, likewise using current methods. The invention further relates to nucleic acid sequences, which code at least a partial sequence of a bioactive polypeptide.

This invention further relates to polypeptide partial sequences, so-called ORF (open-reading-frame)-peptides, according to the sequence protocols Seq. ID Nos. 142–528 and Seq. ID Nos. Seq. 561–575, 577–625, and 630–635.

The invention further relates to the polypeptide sequences that have at least 80% homology, especially 90% homology to the polypeptide partial sequences of ORF ID Nos. 142–528 and Seq. ID Nos. ORF 561–575, 577–625, and 630–635 according to the invention.

The invention also relates to antibodies that are directed against a polypeptide or a fragment thereof and that are coded by the nucleic acids of sequences Seq. ID No. 1 to Seq. ID No. 141 and Seq. ID Nos. 531–552, 554, and 555 according to the invention.

Antibodies are defined especially as monoclonal antibodies.

The antibodies according to the invention can be identified by, i.a., a phage display process. These antibodies are also the subject matter of the invention.

The polypeptide partial sequences according to the invention can be used in a phage display process. The polypeptides that are identified with this process and that bind to the polypeptide partial sequences according to the invention are also the subject matter of the invention.

The nucleic acid sequences according to the invention can also be used in a phage display process.

The polypeptides of sequences Seq. ID Nos. 142–528 and Seq. ID Nos. Seq. 561–575, 577–625, and 630–635 according to the invention can also be used as tools for finding active ingredients against endometrial tumors, which is likewise the subject matter of this invention.

Likewise the subject matter of this invention is the use of nucleic acid sequences according to sequences Seq. ID No. 1 to Seq. ID No. 141 and Seq. ID Nos. 531–552, 554, and 555 for expression of polypeptides, which can be used as tools for finding active ingredients against endometrial tumors.

The invention also relates to the use of the found polypeptide partial sequences Seq. ID Nos. 142–528 and Seq. ID Nos. 561–575, 577–625, and 630–635 as pharmaceutical agents in the gene therapy for treatment of uterus tumors or for the production of a pharmaceutical agent for treatment of uterus tumors.

The invention also relates to pharmaceutical agents that contain at least one polypeptide partial sequence Seq. ID Nos. 142–528 and Seq. ID Nos. Seq. 561–575, 577–625, and 630–635.

The nucleic acid sequences found according to the invention can also be genomic or mRNA sequences.

The invention also relates to genomic genes, their exon and intron structures and their splice variants that can be obtained from cDNAs of sequences Seq. ID No. 1 to Seq. ID No. 141 and Seq. ID Nos. 531–552, 554, and 555, and their use together with suitable regulatory elements, such as suitable promoters and/or enhancers.

With the nucleic acids according to the invention (cDNA sequences) Seq. ID Nos. 1–141 and Seq. ID Nos. 531–552, 554, and 555, genomic BAC, PAC and cosmid libraries are screened, and specifically human clones are isolated via complementary base pairing (hybridization). The BAC, PAC and cosmid clones isolated in this way are hybridized using fluorescence-in-situ hybridization on metaphase chromosomes, and the corresponding chromosome sections on which the corresponding genomic genes lie are identified. BAC, PAC and cosmid clones are sequenced in order to clarify the corresponding genomic genes in their complete structure (promoters, enhancers, silencers, exons and introns). BAC, PAC and cosmid clones can be used as independent molecules for gene transfer (see FIG. 5).

The invention also relates to BAC, PAC and cosmid clones containing functional genes and their chromosomal localization according to sequences Seq. ID No. 1 to Seq. ID No. 141 and Seq. ID Nos. 531–552, 554, and 555, for use as vehicles for gene transfer.

Meanings of Technical Terms and Abbreviations

| | |
|---|---|
| Nucleic acids = | Nucleic acids in this invention are defined as: mRNA, partial cDNA, full-length cDNA and genomic genes (chromosomes) |
| ORF = | Open Reading Frame, a defined sequence of amino acids which can be derived from the cDNA sequence |
| Contig = | A set of DNA sequences that can be combined as a result of very great similarities into one sequence (consensus) |
| Singleton = | A contig that contains only one sequence |
| Module = | Domain of a protein with a defined sequence, which represents one structural unit and which occurs in various proteins |
| N = | selectively the nucleotide A, T, G or C |
| X = | selectively one of the 20 naturally occurring amino acids |

Explanation of the Alignment Parameters
minimal initial match=minimal initial identity area
maximum pads per read=maximum number of insertions
maximum percent mismatch=maximum deviation in %

EXPLANATION OF FIGURES

FIGS. 2b1–2b4 show the entire principle of EST assembling

The following examples explain the production of the nucleic acid sequences according to the invention without limiting the invention to these examples and nucleic acid sequences.

EXAMPLE 1

Search for Tumor-Related Candidate Genes

First, all ESTs of the corresponding tissue from the LifeSeq database (from October 1997) were extracted. They were then assembled by means of the GAP4 program of the Staden package with the parameters 0% mismatch, 8 pads per read and a minimal match of 20. The sequences (fails) not recorded in the GAP4 database were assembled first at 1% mismatch and then again at 2% mismatch with the database. Consensus sequences were computed from the contigs of the database that consisted of more than one sequence. The singletons of the database, which consisted of only one sequence, were re-assembled at 2% mismatch with the sequences not recorded in the GAP4 database. In turn, the consensus sequences were determined for the contigs.

All other ESTs were re-assembled at 4% mismatch. The consensus sequences were extracted once again and finally assembled with the previous consensus sequences and the singletons and the sequences not recorded in the database at 4% mismatch. The consensus sequences were formed and used with the singletons and fails as the initial basis for tissue comparisons. This procedure ensured that among the parameters used, all sequences represented gene regions independent of one another.

Figure 1:
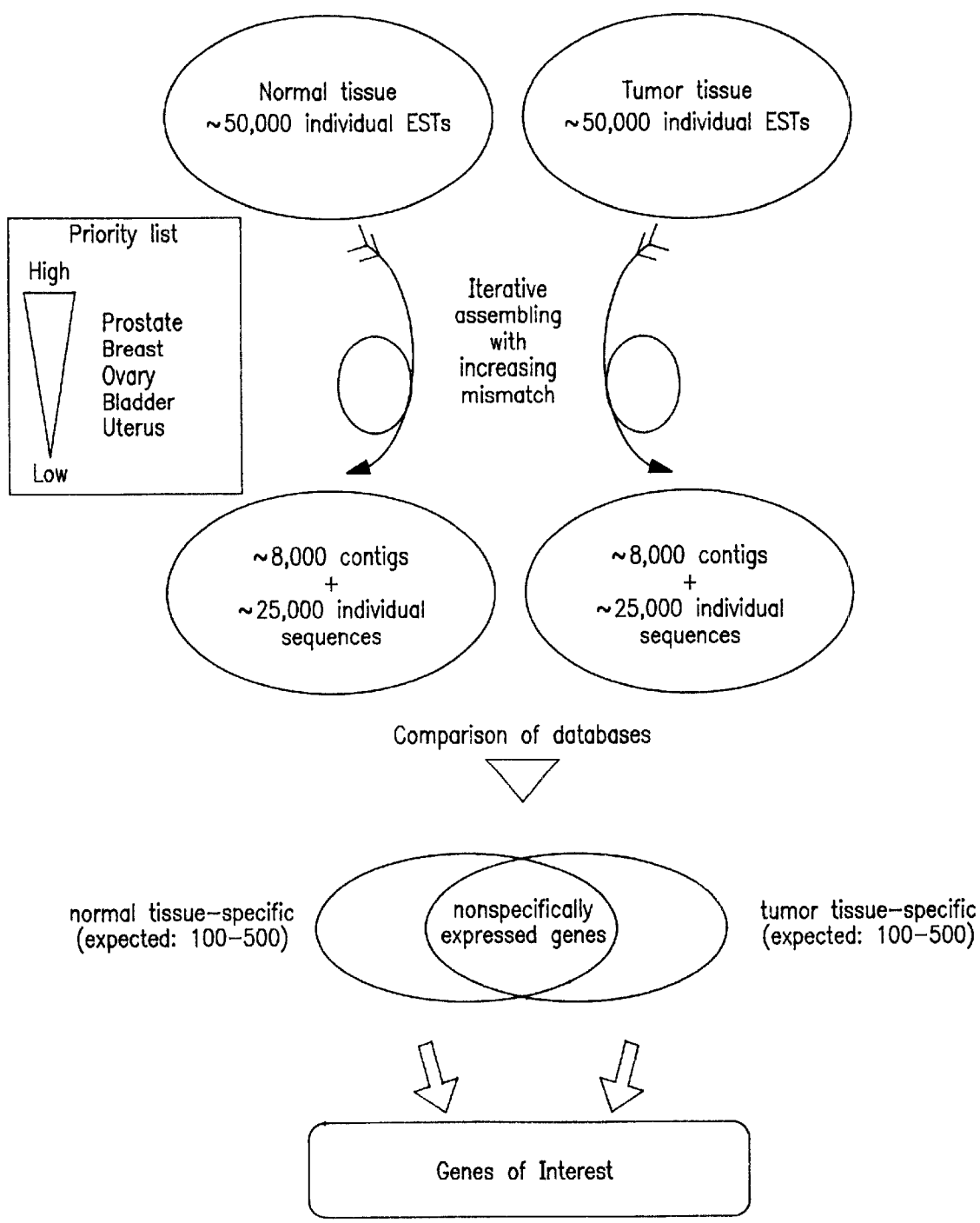
FIG. 1 shows the systematic gene search in the Incyte LifeSeq database
Figure 2A:
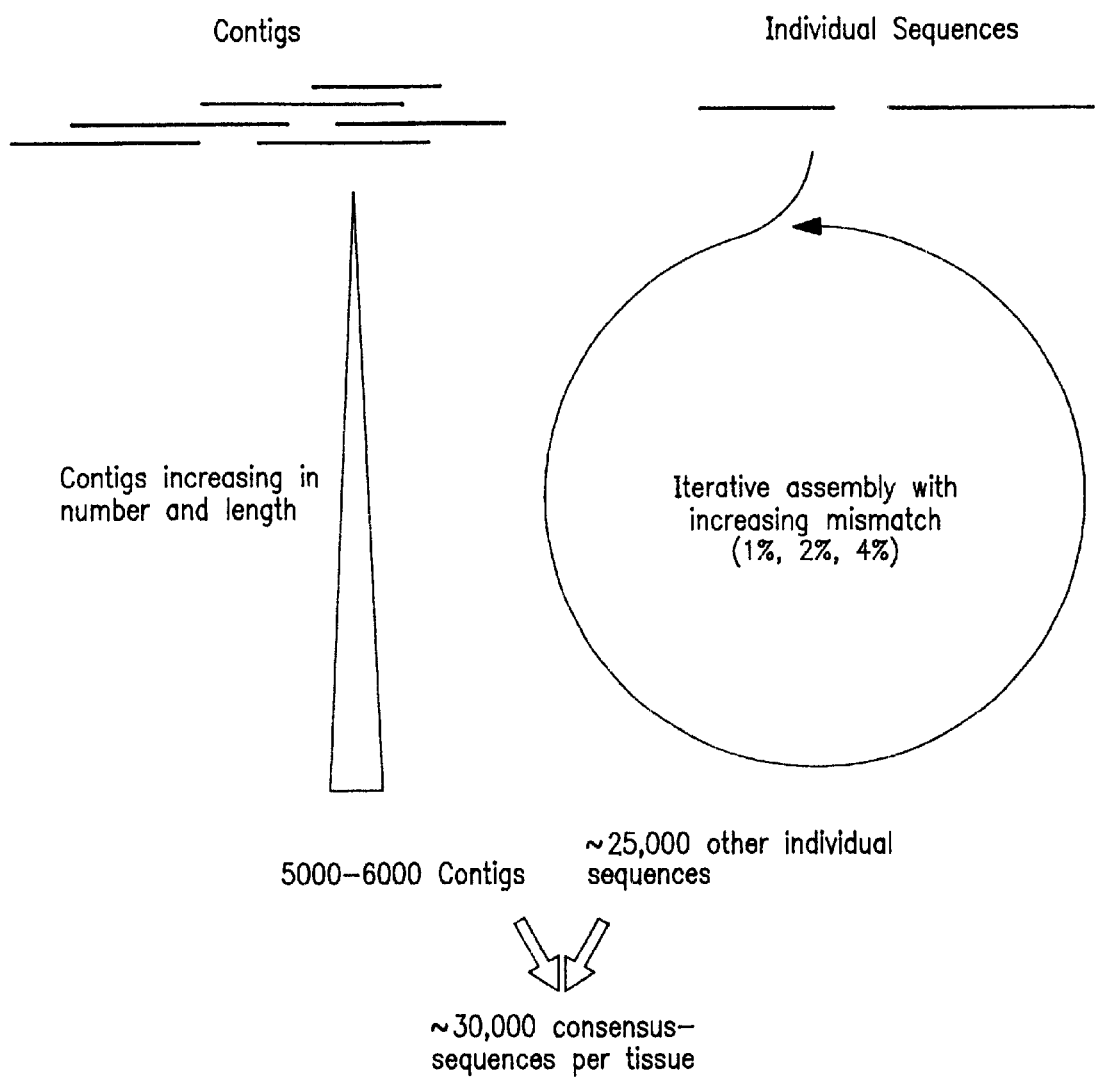
FIG. 2a shows the principle of EST assembling
Figures 2, 2B:
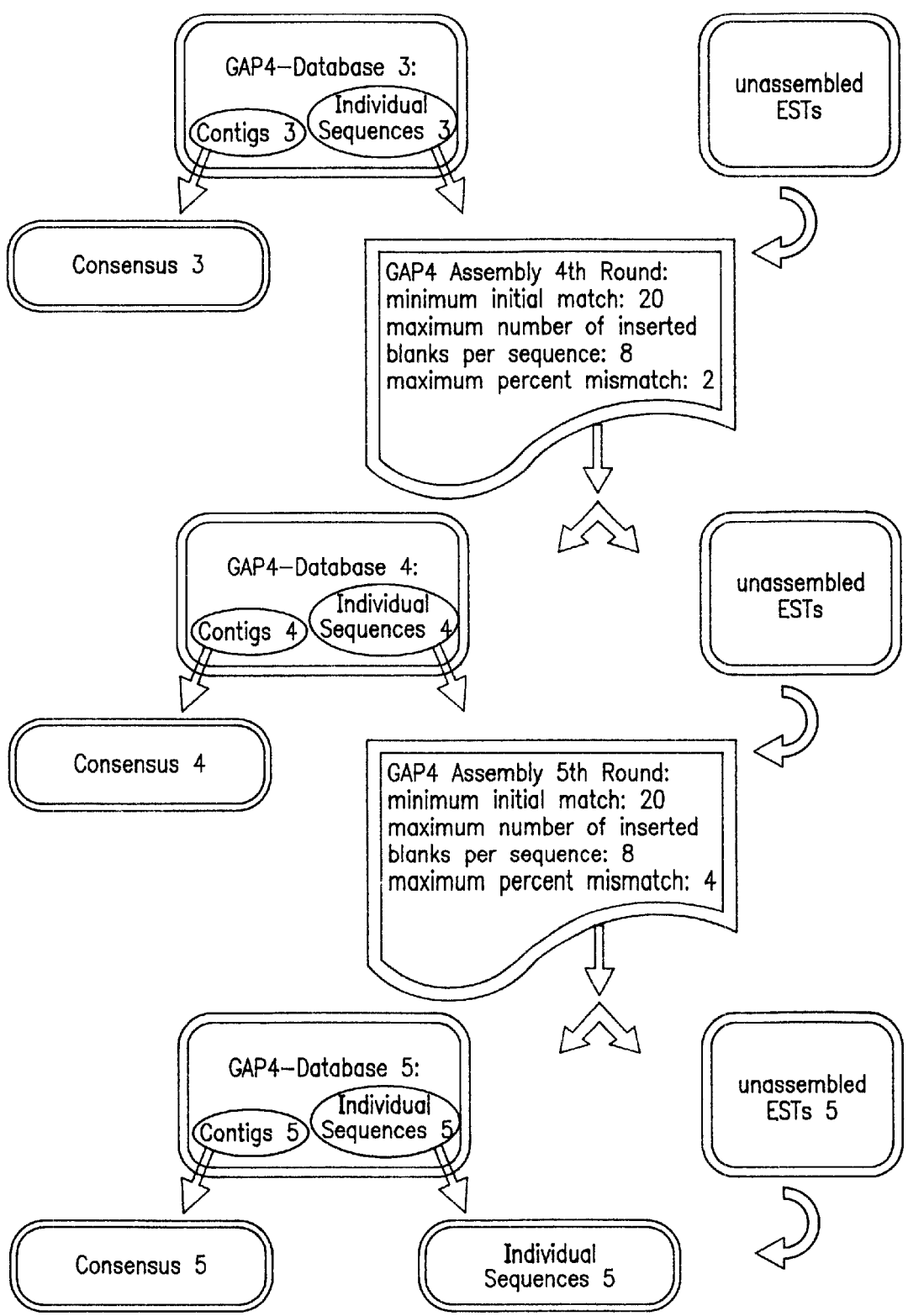
Figures 2, 2B, 3:
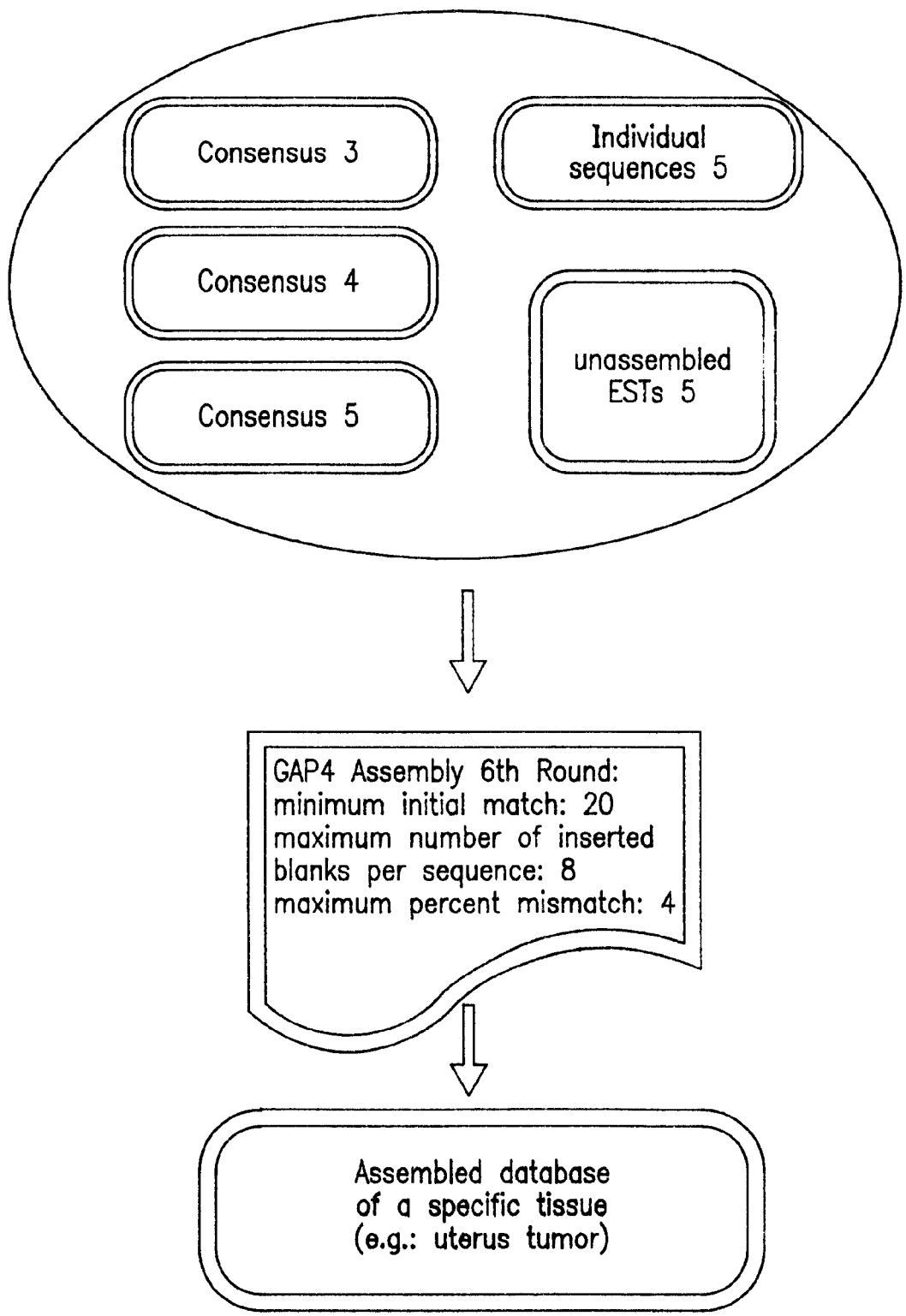
Figures 2, 2B, 3, 4:
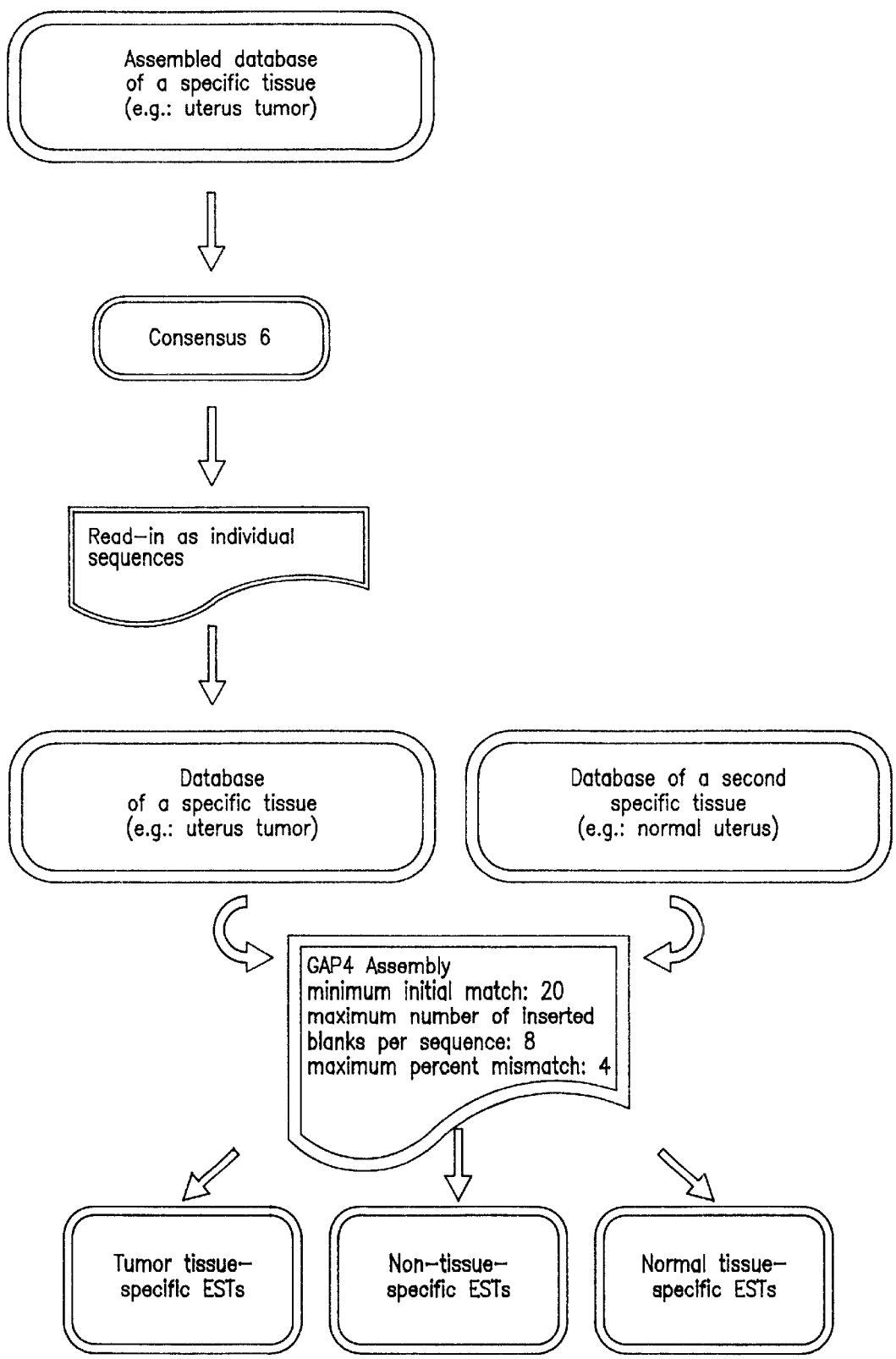
Figure 3:
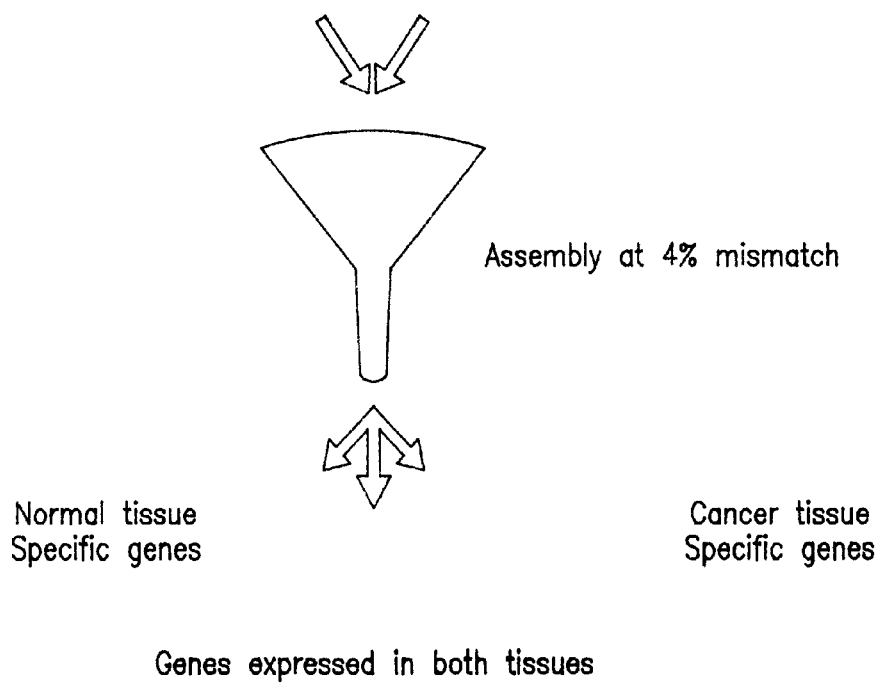
FIG. 3 shows the in-silico subtraction of gene expression in various tissues

FIGS. 2b1–2b4 illustrate the lengthening of the uterus tissue ESTS.

The sequences of the respective tissue assembled in this way were then compared to one another by means of the same program (FIG. 3). To do this, first all sequences of the first tissue were input into the database. (It was therefore important that they were independent of one another.)

Then, all sequences of the second tissue were compared to all those of the first. The result was sequences that were specific to the first or the second tissue as well as those which occurred in both. In the latter, the ratio of the frequency of occurrence in the respective tissue was evaluated. All programs pertaining to the evaluation of the assembled sequences were themselves developed.

Figure 4A:
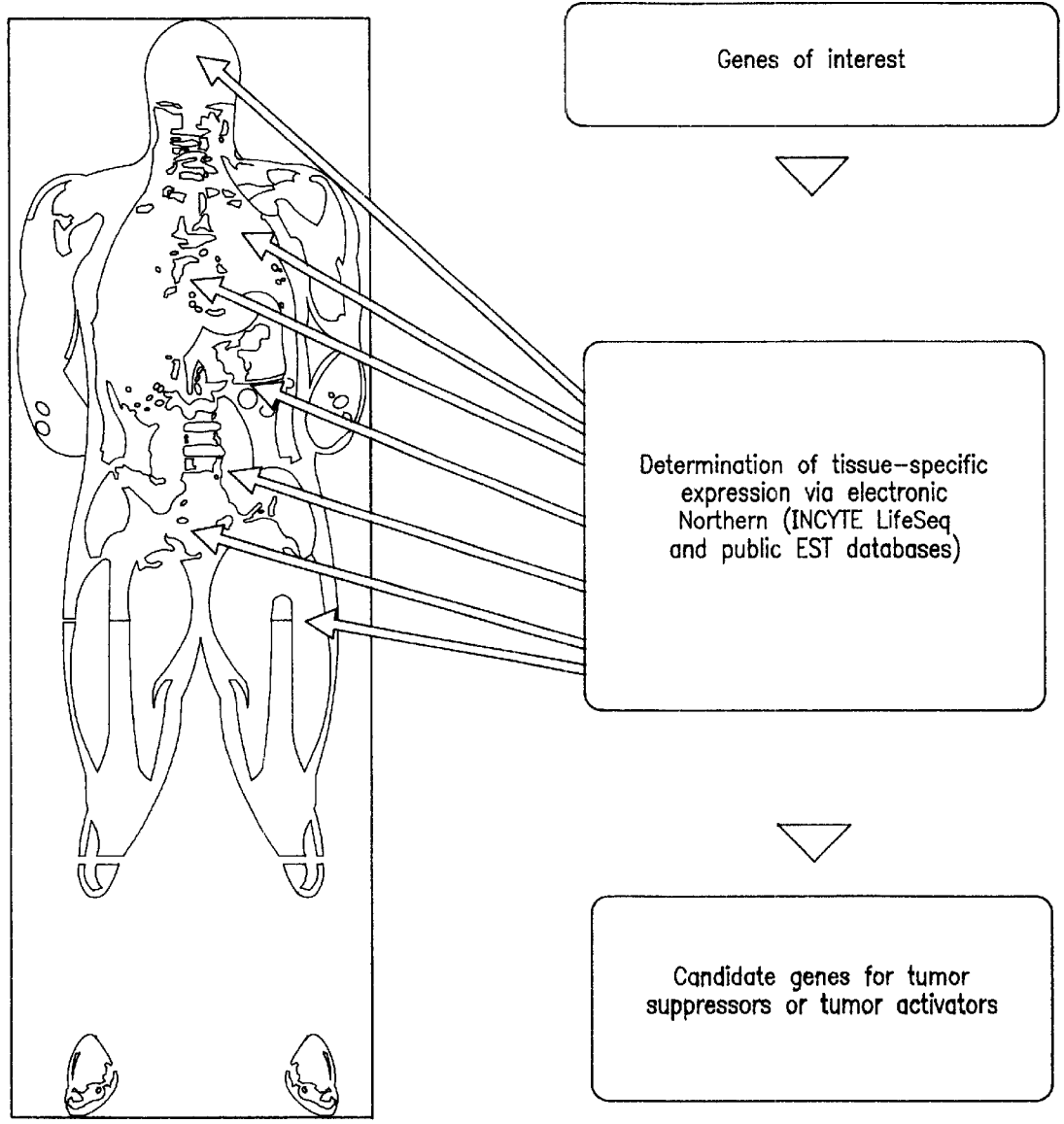
FIG. 4a shows the determination of tissue-specific expression via electronic Northern
Figure 4B:
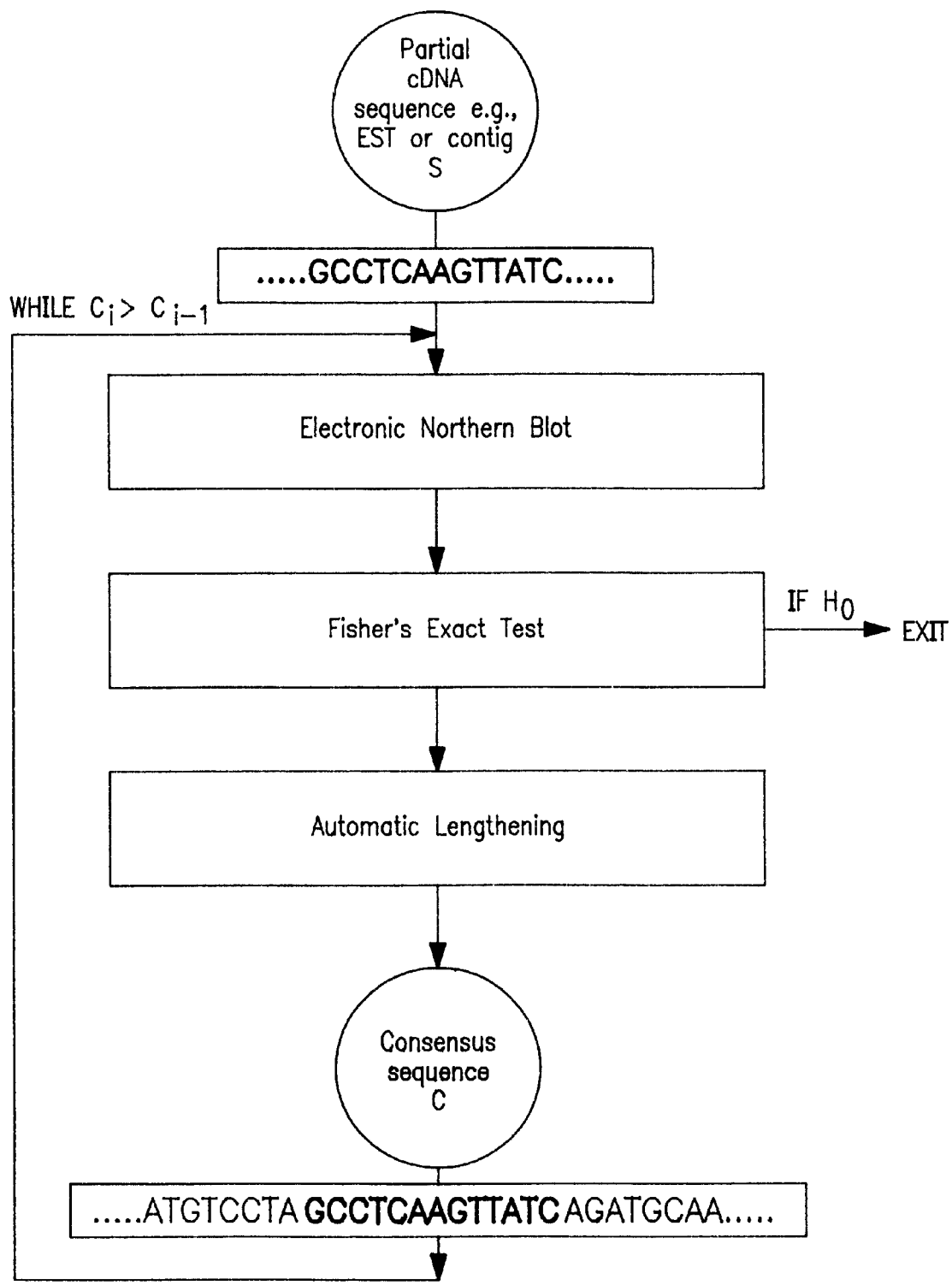
FIG. 4b shows the electronic Northern
Figure 5:
FIG. 5 shows the isolation of genomic BAC and PAC clones.
Figure 5:
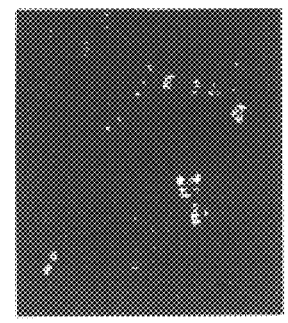
Figure 5:
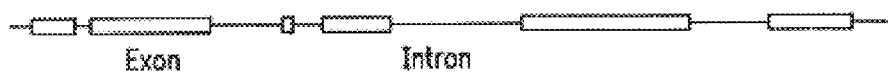

All sequences that occurred more than four times in respectively one of the compared tissues and all that occurred at least five times as often in one of the two tissues were further studied. These sequences were subjected to an electronic Northern (see Example 2.1), by which the distribution in all tumor and normal tissues was studied (see FIG. 4a and FIG. 4b). The relevant candidates were then lengthened using all Incyte ESTs and all ESTs of public databases (see Example 3). Then, the sequences and their translation into possible proteins were compared to all nucleotide and protein databases and were studied for possible regions that code for proteins.

EXAMPLE 2

Algorithm for Identification and Lengthening of Partial cDNA Sequences with Altered Expression Pattern An algorithm for finding overexpressed or underexpressed genes will be explained below. The individual steps are also summarized in a flow chart for the sake of clarity (see FIG. 4b).

2.1. Electronic Northern Blot

By means of a standard program for homology search, e.g., BLAST (Altschul, S. F.; Gish, W.; Miller, W.; Myers, E. W. and Lipman, D. J. (1990) J. Mol. Biol. 215, 403–410), BLAST2 (Altschul, S. F.; Madden, T. L.; Schäffer, A. A.; Zhang, J.; Zhang, Z.; Miller, W., and Lipman, D. J. (1997) Nucleic Acids Research 25 3389–3402) or FASTA (Pearson, W. R. and Lipman, D. J. (1988) Proc. Natl. Acad. Sci. USA 85 2444–2448), the homologous sequences in various EST libraries (private or public) arranged by tissues are determined for a partial DNA sequence S, e.g., an individual EST or a contig of ESTs. The (relative or absolute) tissue-specific occurrence frequencies of this partial sequence S which were determined in this way are called electronic Northern Blots.

2.1.1

Analogously to the procedure described under 2.1, the sequence Seq. ID No. 136 was found, which occurs 15.6× more strongly in the endometrial tumor than in normal tissue.

The result is as follows:

Electronic Northern for SEQ. ID NO.: 136

|  | NORMAL | TUMOR | Ratios | |
| --- | --- | --- | --- | --- |
|  | % frequency | % frequency | N/T | T/N |
| Bladder | 0.0000 | 0.0026 | 0.0000 | undef |
| Breast | 0.0102 | 0.0038 | 2.7221 | 0.3674 |
| Small intestine | 0.0092 | 0.0165 | 0.5561 | 1.7982 |
| Ovary | 0.0090 | 0.0078 | 1.1513 | 0.8686 |
| Endocrine tissue | 0.0000 | 0.0150 | 0.0000 | undef |
| Gastrointestinal | 0.0019 | 0.0093 | 0.2071 | 4.8289 |
| Brain | 0.0059 | 0.0031 | 1.9199 | 0.5209 |
| Hematopoietic | 0.0040 | 0.0379 | 0.1059 | 9.4460 |
| Skin | 0.0073 | 0.0000 | undef | 0.0000 |
| Hepatic | 0.0048 | 0.0065 | 0.7353 | 1.3600 |
| Heart | 0.0000 | 0.0000 | undef | undef |
| Testicles | 0.0000 | 0.0117 | 0.0000 | undef |
| Lung | 0.0114 | 0.0041 | 2.7942 | 0.3579 |
| Stomach-esophagus | 0.0097 | 0.0153 | 0.6303 | 1.5866 |
| Muscle-skeleton | 0.0103 | 0.0120 | 0.8567 | 1.1673 |
| Kidney | 0.0081 | 0.0000 | undef | 0.0000 |
| Pancreas | 0.0050 | 0.0000 | undef | 0.0000 |
| Penis | 0.0060 | 0.0000 | undef | 0.0000 |
| Prostate | 0.0000 | 0.0064 | 0.0000 | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0104 | | | |
| Cervix | 0.0000 | | | |

|  | FETUS | STANDARDIZED/SUB-TRACTED LIBRARIES | |
| --- | --- | --- | --- |
|  | % frequency | | % frequency |
| Development | 0.0139 | Breast | 0.0068 |
| Gastrointestinal | 0.0056 | Ovary_n | 0.0000 |
| Brain | 0.0000 | Ovary_t | 0.0000 |
| Hematopoietic | 0.0079 | Endocrine tissue | 0.0000 |
| Skin | 0.0000 | Fetal | 0.0076 |
| Hepatic | 0.0000 | Gastrointestinal | 0.0000 |
| Heart-blood vessels | 0.0142 | Hematopoietic | 0.0171 |
| Lung | 0.0108 | Skin-muscle | 0.0000 |
| Suprarenal gland | 0.0254 | Testicles | 0.0000 |
| Kidney | 0.0000 | Lung | 0.0164 |
| Placenta | 0.0061 | Nerves | 0.0060 |
| Prostate | 0.0000 | Prostate | 0.0068 |
| Sensory organs | 0.0126 | Sensory Organs | 0.0000 |
| | | Uterus_n | 0.0125 |

In an analogous procedure, the following Northerns were also found:

Electronic Northern for SEQ. ID NO.: 1

|  | NORMAL | TUMOR | Ratios | |
| --- | --- | --- | --- | --- |
|  | % frequency | % frequency | N/T | T/N |
| Bladder | 0.0039 | 0.0026 | 1.5254 | 0.6555 |
| Breast | 0.0038 | 0.0056 | 0.6805 | 1.4694 |
| Small intestine | 0.0061 | 0.0000 | undef | 0.0000 |
| Ovary | 0.0030 | 0.0104 | 0.2878 | 3.4745 |
| Endocrine tissue | 0.0017 | 0.0000 | undef | 0.0000 |
| Gastrointestinal | 0.0019 | 0.0000 | undef | 0.0000 |
| Brain | 0.0030 | 0.0031 | 0.9599 | 1.0417 |
| Hematopoietic | 0.0040 | 0.0000 | undef | 0.0000 |
| Skin | 0.0037 | 0.0000 | undef | 0.0000 |
| Hepatic | 0.0000 | 0.0000 | undef | undef |
| Heart | 0.0011 | 0.0000 | undef | 0.0000 |
| Testicles | 0.0000 | 0.0117 | 0.0000 | undef |
| Lung | 0.0031 | 0.0000 | undef | 0.0000 |
| Stomach-esophagus | 0.0000 | 0.0077 | 0.0000 | undef |
| Muscle-skeleton | 0.0000 | 0.0060 | 0.0000 | undef |
| Kidney | 0.0000 | 0.0000 | undef | undef |
| Pancreas | 0.0000 | 0.0000 | undef | undef |

-continued

| | | | |
|---|---|---|---|
| Penis | 0.0000 | 0.0000 | undef | undef |
| Prostate | 0.0022 | 0.0000 | undef | 0.0000 |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUBTRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0035 |
| Hepatic | 0.0000 | Gastrointestinal | 0.0000 |
| Heart-blood vessels | 0.0036 | Hematopoietic | 0.0000 |
| Lung | 0.0036 | Skin-muscle | 0.0000 |
| Suprarenal gland | 0.0000 | Testicles | 0.0077 |
| Kidney | 0.0000 | Lung | 0.0000 |
| Placenta | 0.0000 | Nerves | 0.0010 |
| Prostate | 0.0000 | Prostate | 0.0000 |
| Sensory organs | 0.0000 | Sensory Organs | 0.0077 |
| | | Uterus_n | 0.0042 |

Electronic Northern for SEQ. ID NO.: 2

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.3166 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUBTRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0122 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |

-continued

| | | | |
|---|---|---|---|
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 3

| | NORMAL | TUMOR | Ratios | |
|---|---|---|---|---|
| | % frequency | % frequency | N/T | T/N |
| Bladder | 0.0078 | 0.0281 | 0.2774 | 3.6055 |
| Breast | 0.0090 | 0.0188 | 0.4764 | 2.0992 |
| Small intestine | 0.0031 | 0.0000 | undef | 0.0000 |
| Ovary | 0.0030 | 0.0052 | 0.5756 | 1.7372 |
| Endocrine tissue | 0.0085 | 0.0176 | 0.4852 | 2.0611 |
| Gastrointestinal | 0.0019 | 0.0093 | 0.2071 | 4.8289 |
| Brain | 0.0118 | 0.0123 | 0.9599 | 1.0417 |
| Hematopoietic | 0.0027 | 0.0000 | undef | 0.0000 |
| Skin | 0.0073 | 0.0000 | undef | 0.0000 |
| Hepatic | 0.0000 | 0.0000 | undef | undef |
| Heart | 0.0042 | 0.0000 | undef | 0.0000 |
| Testicles | 0.0058 | 0.0117 | 0.4920 | 2.0326 |
| Lung | 0.0073 | 0.0020 | 3.5562 | 0.2812 |
| Stomach-esophagus | 0.0097 | 0.0153 | 0.6303 | 1.5866 |
| Muscle-skeleton | 0.0034 | 0.0240 | 0.1428 | 7.0040 |
| Kidney | 0.0136 | 0.0274 | 0.4956 | 2.0176 |
| Pancreas | 0.0050 | 0.0000 | undef | 0.0000 |
| Penis | 0.0090 | 0.0000 | undef | 0.0000 |
| Prostate | 0.0109 | 0.0149 | 0.7312 | 1.3677 |
| Uterus-endometrium | 0.0068 | 0.1583 | 0.0427 | 23.4317 |
| Uterus-myometrium | 0.0076 | 0.0272 | 0.2806 | 3.5642 |
| Uterus-general | 0.0102 | 0.0000 | undef | 0.0000 |
| Breast hyperplasia | 0.0160 | | | |
| Prostate hyperplasia | 0.0119 | | | |
| Seminal vesicle | 0.0178 | | | |
| Sensory organs | 0.0000 | | | |
| White blood cells | 0.0009 | | | |
| Cervix | 0.0000 | | | |

| | FETUS % frequency | STANDARDIZED/SUBTRACTED LIBRARIES % frequency | |
|---|---|---|---|
| Development | 0.0278 | Breast | 0.0272 |
| Gastrointestinal | 0.0194 | Ovary_n | 0.0000 |
| Brain | 0.0063 | Ovary_t | 0.0203 |
| Hematopoietic | 0.0157 | Endocrine tissue | 0.0000 |
| Skin | 0.0000 | Fetal | 0.0076 |
| Hepatic | 0.0000 | Gastrointestinal | 0.0000 |
| Heart-blood vessels | 0.0107 | Hematopoietic | 0.0114 |
| Lung | 0.0145 | Skin-muscle | 0.0194 |
| Suprarenal gland | 0.0254 | Testicles | 0.0000 |
| Kidney | 0.0124 | Lung | 0.0164 |
| Placenta | 0.0121 | Nerves | 0.0120 |
| Prostate | 0.0249 | Prostate | 0.0137 |
| Sensory organs | 0.0000 | Sensory Organs | 0.0155 |
| | | Uterus_n | 0.0083 |

Electronic Northern for SEQ. ID NO.: 4

| | NORMAL | TUMOR | Ratios | |
|---|---|---|---|---|
| | % frequency | % frequency | N/T | T/N |
| Bladder | 0.0039 | 0.0000 | undef | 0.0000 |
| Breast | 0.0026 | 0.0000 | undef | 0.0000 |
| Small intestine | 0.0000 | 0.0165 | 0.0000 | undef |
| Ovary | 0.0030 | 0.0000 | undef | 0.0000 |
| Endocrine tissue | 0.0017 | 0.0000 | undef | 0.0000 |
| Gastrointestinal | 0.0077 | 0.0000 | undef | 0.0000 |
| Brain | 0.0015 | 0.0021 | 0.7200 | 1.3890 |
| Hematopoietic | 0.0000 | 0.0000 | undef | undef |
| Skin | 0.0000 | 0.0000 | undef | undef |
| Hepatic | 0.0048 | 0.0000 | undef | 0.0000 |
| Heart | 0.0011 | 0.0000 | undef | 0.0000 |
| Testicles | 0.0000 | 0.0000 | undef | undef |
| Lung | 0.0021 | 0.0020 | 1.0161 | 0.9842 |

-continued

| | | | |
|---|---|---|---|
| Stomach-esophagus | 0.0193 | 0.0077 | 2.5211 | 0.3967 |
| Muscle-skeleton | 0.0000 | 0.0060 | 0.0000 | undef |
| Kidney | 0.0000 | 0.0000 | undef | undef |
| Pancreas | 0.0017 | 0.0000 | undef | 0.0000 |
| Penis | 0.0030 | 0.0000 | undef | 0.0000 |
| Prostate | 0.0000 | 0.0000 | undef | undef |
| Uterus-endometrium | 0.0000 | 0.1055 | 0.0000 | undef |
| Uterus-myometrium | 0.0076 | 0.0068 | 1.1223 | 0.8911 |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0017 | | | |
| Cervix | 0.0213 | | | |

| | FETUS % frequency | STANDARDIZED/SUB-TRACTED LIBRARIES % frequency | | |
|---|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0041 |
| Hepatic | 0.0000 | Gastrointestinal | 0.0000 |
| Heart-blood vessels | 0.0036 | Hematopoietic | 0.0000 |
| Lung | 0.0036 | Skin-muscle | 0.0032 |
| Suprarenal gland | 0.0000 | Testicles | 0.0000 |
| Kidney | 0.0000 | Lung | 0.0082 |
| Placenta | 0.0000 | Nerves | 0.0020 |
| Prostate | 0.0000 | Prostate | 0.0000 |
| Sensory organs | 0.0000 | Sensory Organs | 0.0000 |
| | | Uterus_n | 0.0167 |

Electronic Northern for SEQ. ID NO.: 5

| | NORMAL % frequency | TUMOR % frequency | Ratios N/T | Ratios T/N |
|---|---|---|---|---|
| Bladder | 0.0039 | 0.0026 | 1.5254 | 0.6555 |
| Breast | 0.0038 | 0.0038 | 1.0208 | 0.9796 |
| Small intestine | 0.0031 | 0.0000 | undef | 0.0000 |
| Ovary | 0.0060 | 0.0000 | undef | 0.0000 |
| Endocrine tissue | 0.0000 | 0.0025 | 0.0000 | undef |
| Gastrointestinal | 0.0000 | 0.0093 | 0.0000 | undef |
| Brain | 0.0015 | 0.0021 | 0.7200 | 1.3890 |
| Hematopoietic | 0.0053 | 0.0000 | undef | 0.0000 |
| Skin | 0.0000 | 0.0000 | undef | undef |
| Hepatic | 0.0000 | 0.0000 | undef | undef |
| Heart | 0.0053 | 0.0137 | 0.3855 | 2.5941 |
| Testicles | 0.0000 | 0.0000 | undef | undef |
| Lung | 0.0000 | 0.0000 | undef | undef |
| Stomach-esophagus | 0.0193 | 0.0000 | undef | 0.0000 |
| Muscle-skeleton | 0.0017 | 0.0000 | undef | 0.0000 |
| Kidney | 0.0000 | 0.0000 | undef | undef |
| Pancreas | 0.0017 | 0.0055 | 0.2991 | 3.3428 |
| Penis | 0.0060 | 0.0267 | 0.2246 | 4.4517 |
| Prostate | 0.0065 | 0.0021 | 3.0709 | 0.3256 |
| Uterus-endometrium | 0.0135 | 0.1055 | 0.1280 | 7.8106 |
| Uterus-myometrium | 0.0000 | 0.0068 | 0.0000 | undef |
| Uterus-general | 0.0051 | 0.0000 | undef | 0.0000 |
| Breast hyperplasia | 0.0096 | | | |
| Prostate hyperplasia | 0.0000 | | | |
| Seminal vesicle | 0.0178 | | | |
| Sensory organs | 0.0000 | | | |
| White blood cells | 0.0078 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0083 | Ovary_n | 0.0000 |
| Brain | 0.0000 | Ovary_t | 0.0759 |
| Hematopoietic | 0.0079 | Endocrine tissue | 0.0000 |
| Skin | 0.0000 | Fetal | 0.0029 |
| Hepatic | 0.0000 | Gastrointestinal | 0.0122 |
| Heart-blood vessels | 0.0000 | Hematopoietic | 0.0057 |
| Lung | 0.0036 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0040 |
| Prostate | 0.0000 | Prostate | 0.0000 |
| Sensory organs | 0.0000 | Sensory Organs | 0.0000 |
| | | Uterus_n | 0.0083 |

Electronic Northern for SEQ. ID NO.: 6

| | NORMAL % frequency | TUMOR % frequency | Ratios N/T | Ratios T/N |
|---|---|---|---|---|
| Bladder | 0.0156 | 0.0077 | 2.0339 | 0.4917 |
| Breast | 0.0051 | 0.0075 | 0.6805 | 1.4694 |
| Small intestine | 0.0123 | 0.0331 | 0.3707 | 2.6973 |
| Ovary | 0.0120 | 0.0104 | 1.1513 | 0.8686 |
| Endocrine tissue | 0.0085 | 0.0075 | 1.1321 | 0.8833 |
| Gastrointestinal | 0.0096 | 0.0278 | 0.3451 | 2.8974 |
| Brain | 0.0133 | 0.0164 | 0.8100 | 1.2346 |
| Hematopoietic | 0.0120 | 0.0000 | undef | 0.0000 |
| Skin | 0.0073 | 0.0000 | undef | 0.0000 |
| Hepatic | 0.0000 | 0.0000 | undef | undef |
| Heart | 0.0170 | 0.0000 | undef | 0.0000 |
| Testicles | 0.0058 | 0.0117 | 0.4920 | 2.0326 |
| Lung | 0.0197 | 0.0164 | 1.2066 | 0.8288 |
| Stomach-esophagus | 0.0193 | 0.0000 | undef | 0.0000 |
| Muscle-skeleton | 0.0034 | 0.0180 | 0.1904 | 5.2530 |
| Kidney | 0.0054 | 0.0274 | 0.1983 | 5.0439 |
| Pancreas | 0.0066 | 0.0055 | 1.1966 | 0.8357 |
| Penis | 0.0240 | 0.0267 | 0.8985 | 1.1129 |
| Prostate | 0.0044 | 0.0192 | 0.2275 | 4.3961 |
| Uterus-endometrium | 0.0000 | 0.1055 | 0.0000 | undef |
| Uterus-myometrium | 0.0229 | 0.0272 | 0.8417 | 1.1881 |
| Uterus-general | 0.0102 | 0.0000 | undef | 0.0000 |
| Breast hyperplasia | 0.0192 | | | |
| Prostate hyperplasia | 0.0059 | | | |
| Seminal vesicle | 0.0089 | | | |
| Sensory organs | 0.0000 | | | |
| White blood cells | 0.0104 | | | |
| Cervix | 0.0106 | | | |

| | FETUS % frequency | STANDARDIZED/SUB-TRACTED LIBRARIES % frequency | |
|---|---|---|---|
| Development | 0.0139 | Breast | 0.0136 |
| Gastrointestinal | 0.0250 | Ovary_n | 0.0000 |
| Brain | 0.0063 | Ovary_t | 0.0354 |
| Hematopoietic | 0.0157 | Endocrine tissue | 0.0000 |
| Skin | 0.0000 | Fetal | 0.0245 |
| Hepatic | 0.0260 | Gastrointestinal | 0.0244 |
| Heart-blood vessels | 0.0178 | Hematopoietic | 0.0228 |
| Lung | 0.0036 | Skin-muscle | 0.0551 |
| Suprarenal gland | 0.0000 | Testicles | 0.0386 |
| Kidney | 0.0000 | Lung | 0.0082 |
| Placenta | 0.0121 | Nerves | 0.0181 |
| Prostate | 0.0000 | Prostate | 0.0068 |
| Sensory organs | 0.0251 | Sensory Organs | 0.0000 |
| | | Uterus_n | 0.0167 |

Electronic Northern for SEQ. ID NO.: 7

| | NORMAL % frequency | TUMOR % frequency | Ratios N/T | Ratios T/N |
|---|---|---|---|---|
| Bladder | 0.0000 | 0.0000 | undef | undef |
| Breast | 0.0026 | 0.0019 | 1.3611 | 0.7347 |
| Small intestine | 0.0061 | 0.0000 | undef | 0.0000 |
| Ovary | 0.0060 | 0.0026 | 2.3025 | 0.4343 |
| Endocrine tissue | 0.0051 | 0.0000 | undef | 0.0000 |
| Gastrointestinal | 0.0096 | 0.0139 | 0.6903 | 1.4487 |
| Brain | 0.0037 | 0.0092 | 0.4000 | 2.5001 |
| Hematopoietic | 0.0013 | 0.0000 | undef | 0.0000 |
| Skin | 0.0000 | 0.0000 | undef | undef |

-continued

| | | | | |
|---|---|---|---|---|
| Hepatic | 0.0000 | 0.0000 | undef | undef |
| Heart | 0.0042 | 0.0000 | undef | 0.0000 |
| Testicles | 0.0000 | 0.0000 | undef | undef |
| Lung | 0.0042 | 0.0041 | 1.0161 | 0.9842 |
| Stomach-esophagus | 0.0097 | 0.0153 | 0.6303 | 1.5866 |
| Muscle-skeleton | 0.0000 | 0.0120 | 0.0000 | undef |
| Kidney | 0.0027 | 0.0000 | undef | 0.0000 |
| Pancreas | 0.0017 | 0.0000 | undef | 0.0000 |
| Penis | 0.0150 | 0.0000 | undef | 0.0000 |
| Prostate | 0.0087 | 0.0043 | 2.0473 | 0.4885 |
| Uterus-endometrium | 0.0068 | 0.1055 | 0.0640 | 15.6211 |
| Uterus-myometrium | 0.0076 | 0.0000 | undef | 0.0000 |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0089 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency |
|---|---|---|
| Development | 0.0000 | Breast | 0.0000 |
| Gastrointestinal | 0.0000 | Ovary_n | 0.1595 |
| Brain | 0.0000 | Ovary_t | 0.0000 |
| Hematopoietic | 0.0000 | Endocrine tissue | 0.0000 |
| Skin | 0.0000 | Fetal | 0.0082 |
| Hepatic | 0.0000 | Gastrointestinal | 0.0000 |
| Heart-blood vessels | 0.0036 | Hematopoietic | 0.0000 |
| Lung | 0.0000 | Skin-muscle | 0.0097 |
| Suprarenal gland | 0.0000 | Testicles | 0.0000 |
| Kidney | 0.0062 | Lung | 0.0000 |
| Placenta | 0.0000 | Nerves | 0.0000 |
| Prostate | 0.0000 | Prostate | 0.0000 |
| Sensory organs | 0.0126 | Sensory Organs | 0.0155 |
| | | Uterus_n | 0.0000 |

Electronic Northern for SEQ. ID NO.: 8

| | NORMAL % frequency | TUMOR % frequency | Ratios N/T | Ratios T/N |
|---|---|---|---|---|
| Bladder | 0.0000 | 0.0026 | 0.0000 | undef |
| Breast | 0.0000 | 0.0019 | 0.0000 | undef |
| Small intestine | 0.0031 | 0.0000 | undef | 0.0000 |
| Ovary | 0.0000 | 0.0000 | undef | undef |
| Endocrine tissue | 0.0000 | 0.0025 | 0.0000 | undef |
| Gastrointestinal | 0.0019 | 0.0046 | 0.4142 | 2.4145 |
| Brain | 0.0000 | 0.0021 | 0.0000 | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0021 | 0.0000 | undef | 0.0000 |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0034 | 0.0000 | undef | 0.0000 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0118 | | | |
| White blood cells | 0.0009 | | | |
| Cervix | 0.0000 | | | |

| | FETUS % frequency | STANDARDIZED/SUB- TRACTED LIBRARIES % frequency |
|---|---|---|
| Development | 0.0000 | Breast | 0.0068 |
| Gastrointestinal | 0.0000 | Ovary_n | 0.0000 |
| Brain | 0.0000 | Ovary_t | 0.0203 |
| Hematopoietic | 0.0079 | Endocrine tissue | 0.0000 |
| Skin | 0.0000 | Fetal | 0.0047 |
| Hepatic | 0.0000 | Gastrointestinal | 0.0000 |
| Heart-blood vessels | 0.0000 | Hematopoietic | 0.0057 |
| Lung | 0.0108 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0050 |
| Prostate | 0.0000 | Prostate | 0.0137 |
| Sensory organs | 0.0000 | Sensory Organs | 0.0000 |
| | | Uterus_n | 0.0000 |

Electronic Northern for SEQ. ID NO.: 9

| | NORMAL % frequency | TUMOR % frequency | Ratios N/T | Ratios T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0019 | 0.0000 | undef | 0.0000 |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency |
|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

-continued

Electronic Northern for SEQ. ID NO.: 10

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 11

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0090 | 0.0188 | 0.4764 | 2.0992 |
| Small intestine | 0.0153 | 0.0000 | undef | 0.0000 |
| Ovary | 0.0000 | 0.0000 | undef | undef |
| Endocrine tissue | 0.0051 | 0.0050 | 1.0189 | 0.9815 |
| Gastrointestinal | 0.0038 | 0.0000 | undef | 0.0000 |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0115 | 0.0117 | 0.9839 | 1.0163 |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0066 | 0.0055 | 1.1966 | 0.8357 |
| Penis | 0.0000 | 0.0000 | undef | undef |
| Prostate | 0.0131 | 0.0213 | 0.6142 | 1.6282 |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0032 | | | |
| Prostate hyperplasia | 0.0178 | | | |
| Seminal vesicle | 0.0000 | | | |
| Sensory organs | 0.0000 | | | |
| White blood cells | 0.0017 | | | |
| Cervix | 0.0106 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0154 |
| Kidney | 0.0000 | Lung | 0.0000 |
| Placenta | 0.0000 | Nerves | 0.0000 |
| Prostate | 0.0000 | Prostate | 0.0342 |
| Sensory organs | 0.0000 | Sensory Organs | 0.0000 |
| | | Uterus_n | 0.0000 |

Electronic Northern for SEQ. ID NO.: 12

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0019 | 0.0000 | undef | 0.0000 |
| Brain | 0.0007 | 0.0000 | undef | 0.0000 |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0021 | 0.0000 | undef | 0.0000 |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0051 |
| Hematopoietic | 0.0000 | Endocrine tissue | 0.0000 |
| Skin | 0.0000 | Fetal | 0.0035 |
| Hepatic | 0.0000 | Gastrointestinal | 0.0000 |
| Heart-blood vessels | 0.0000 | Hematopoietic | 0.0057 |
| Lung | 0.0072 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0030 |

| | | | | |
|---|---|---|---|---|
| Prostate | 0.0000 | Prostate | 0.0000 | |
| Sensory organs | 0.0000 | Sensory Organs | 0.0000 | |
| | | Uterus_n | 0.0000 | |

Electronic Northern for SEQ. ID NO.: 13

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0038 | 0.0019 | 2.0416 | 0.4898 |
| Small intestine | 0.0061 | 0.0000 | undef | 0.0000 |
| Ovary | 0.0000 | 0.0208 | 0.0000 | undef |
| Endocrine tissue | 0.0034 | 0.0201 | 0.1698 | 5.8889 |
| Gastrointestinal | 0.0057 | 0.0000 | undef | 0.0000 |
| Brain | 0.0081 | 0.0072 | 1.1314 | 0.8839 |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0021 | 0.0000 | undef | 0.0000 |
| Testicles | 0.0058 | 0.0000 | undef | 0.0000 |
| Lung | 0.0010 | 0.0020 | 0.5080 | 1.9684 |
| Stomach-esophagus | 0.0000 | 0.0000 | undef | undef |
| Muscle-skeleton | 0.0051 | 0.0000 | undef | 0.0000 |
| Kidney | 0.0054 | 0.0000 | undef | 0.0000 |
| Pancreas | 0.0017 | 0.0000 | undef | 0.0000 |
| Penis | 0.0030 | 0.0000 | undef | 0.0000 |
| Prostate | 0.0065 | 0.0043 | 1.5354 | 0.6513 |
| Uterus-endometrium | 0.0068 | 0.1583 | 0.0427 | 23.4317 |
| Uterus-myometrium | 0.0152 | 0.0000 | undef | 0.0000 |
| Uterus-general | 0.0051 | 0.0000 | undef | 0.0000 |
| Breast hyperplasia | 0.0096 | | | |
| Prostate hyperplasia | 0.0149 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | | |
|---|---|---|---|---|
| Development | 0.0000 | Breast | 0.0000 | |
| Gastrointestinal | 0.0028 | Ovary_n | 0.0000 | |
| Brain | 0.0000 | Ovary_t | 0.0000 | |
| Hematopoietic | 0.0039 | Endocrine tissue | 0.0000 | |
| Skin | 0.0000 | Fetal | 0.0093 | |
| Hepatic | 0.0000 | Gastrointestinal | 0.0000 | |
| Heart-blood vessels | 0.0036 | Hematopoietic | 0.0057 | |
| Lung | 0.0036 | Skin-muscle | 0.0032 | |
| Suprarenal gland | 0.0000 | Testicles | 0.0309 | |
| Kidney | 0.0062 | Lung | 0.0000 | |
| Placenta | 0.0000 | Nerves | 0.0100 | |
| Prostate | 0.0000 | Prostate | 0.0000 | |
| Sensory organs | 0.0000 | Sensory Organs | 0.0077 | |
| | | Uterus_n | 0.0250 | |

Electronic Northern for SEQ. ID NO.: 14

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0030 | 0.0000 | undef | 0.0000 |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0054 | 0.0000 | undef | 0.0000 |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 15

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |

-continued

| | | |
|---|---|---|
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 16

| | NORMAL | TUMOR | Ratios | |
|---|---|---|---|---|
| | % frequency | % frequency | N/T | T/N |
| Bladder | 0.0078 | 0.0128 | 0.6102 | 1.6389 |
| Breast | 0.0153 | 0.0188 | 0.8166 | 1.2245 |
| Small intestine | 0.0184 | 0.0000 | undef | 0.0000 |
| Ovary | 0.0090 | 0.0182 | 0.4934 | 2.0268 |
| Endocrine tissue | 0.0187 | 0.0100 | 1.8679 | 0.5354 |
| Gastrointestinal | 0.0192 | 0.0324 | 0.5917 | 1.6901 |
| Brain | 0.0067 | 0.0205 | 0.3240 | 3.0866 |
| Hematopoietic | 0.0147 | 0.0379 | 0.3882 | 2.5762 |
| Skin | 0.0073 | 0.0000 | undef | 0.0000 |
| Hepatic | 0.0143 | 0.0323 | 0.4412 | 2.2666 |
| Heart | 0.0148 | 0.0275 | 0.5397 | 1.8529 |
| Testicles | 0.0115 | 0.0000 | undef | 0.0000 |
| Lung | 0.0156 | 0.0102 | 1.5241 | 0.6561 |
| Stomach-esophagus | 0.0290 | 0.0307 | 0.9454 | 1.0578 |
| Muscle-skeleton | 0.0154 | 0.0120 | 1.2850 | 0.7782 |
| Kidney | 0.0407 | 0.0068 | 5.9478 | 0.1681 |
| Pancreas | 0.0132 | 0.0110 | 1.1966 | 0.8357 |
| Penis | 0.0120 | 0.0267 | 0.4493 | 2.2259 |
| Prostate | 0.0153 | 0.0085 | 1.7913 | 0.5582 |
| Uterus-endometrium | 0.0000 | 0.1055 | 0.0000 | undef |
| Uterus-myometrium | 0.0229 | 0.0068 | 3.3668 | 0.2970 |
| Uterus-general | 0.0153 | 0.0000 | undef | 0.0000 |
| Breast hyperplasia | 0.0192 | | | |
| Prostate hyperplasia | 0.0059 | | | |
| Seminal vesicle | 0.0178 | | | |
| Sensory organs | 0.0353 | | | |
| White blood cells | 0.0165 | | | |
| Cervix | 0.0319 | | | |

| | FETUS | STANDARDIZED/SUB-TRACTED LIBRARIES | |
|---|---|---|---|
| | % frequency | | % frequency |
| Development | 0.0278 | Breast | 0.0476 |
| Gastrointestinal | 0.0056 | Ovary_n | 0.0000 |
| Brain | 0.0000 | Ovary_t | 0.1114 |
| Hematopoietic | 0.0393 | Endocrine tissue | 0.0245 |
| Skin | 0.0000 | Fetal | 0.0175 |
| Hepatic | 0.0000 | Gastrointestinal | 0.0244 |
| Heart-blood vessels | 0.0000 | Hematopoietic | 0.0114 |
| Lung | 0.0072 | Skin-muscle | 0.0292 |
| Suprarenal gland | 0.0000 | Testicles | 0.0000 |
| Kidney | 0.0124 | Lung | 0.0082 |
| Placenta | 0.0061 | Nerves | 0.0020 |
| Prostate | 0.0249 | Prostate | 0.0000 |
| Sensory organs | 0.0000 | Sensory Organs | 0.0310 |
| | | Uterus_n | 0.0167 |

Electronic Northern for SEQ. ID NO.: 17

| | NORMAL | TUMOR | Ratios | |
|---|---|---|---|---|
| | % frequency | % frequency | N/T | T/N |
| Bladder | 0.0039 | 0.0026 | 1.5254 | 0.6555 |
| Breast | 0.0051 | 0.0000 | undef | 0.0000 |
| Small intestine | 0.0031 | 0.0000 | undef | 0.0000 |
| Ovary | 0.0030 | 0.0000 | undef | 0.0000 |
| Endocrine tissue | 0.0017 | 0.0025 | 0.6792 | 1.4722 |
| Gastrointestinal | 0.0000 | 0.0046 | 0.0000 | undef |
| Brain | 0.0111 | 0.0031 | 3.5998 | 0.2778 |
| Hematopoietic | 0.0000 | 0.0000 | undef | undef |
| Skin | 0.0037 | 0.0000 | undef | 0.0000 |
| Hepatic | 0.0000 | 0.0129 | 0.0000 | undef |
| Heart | 0.0011 | 0.0000 | undef | 0.0000 |
| Testicles | 0.0000 | 0.0000 | undef | undef |
| Lung | 0.0031 | 0.0041 | 0.7621 | 1.3122 |
| Stomach-esophagus | 0.0000 | 0.0000 | undef | undef |
| Muscle-skeleton | 0.0034 | 0.0060 | 0.5711 | 1.7510 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0076 | 0.0000 | undef | 0.0000 |
| Uterus-general | 0.0000 | 0.0000 | undef | undef |
| Breast hyperplasia | 0.0096 | | | |
| Prostate hyperplasia | 0.0000 | | | |
| Seminal vesicle | 0.0000 | | | |
| Sensory organs | 0.0000 | | | |
| White blood cells | 0.0035 | | | |
| Cervix | 0.0000 | | | |

| | FETUS | STANDARDIZED/SUB-TRACTED LIBRARIES | |
|---|---|---|---|
| | % frequency | | % frequency |
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0079 | Endocrine tissue | 0.0000 |
| Skin | 0.0000 | Fetal | 0.0070 |
| Hepatic | 0.0000 | Gastrointestinal | 0.0000 |
| Heart-blood vessels | 0.0036 | Hematopoietic | 0.0000 |
| Lung | 0.0036 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0100 |
| Prostate | 0.0000 | Prostate | 0.0000 |
| Sensory organs | 0.0000 | Sensory Organs | 0.0000 |
| | | Uterus_n | 0.0208 |

Electronic Northern for SEQ. ID NO.: 18

| | NORMAL | TUMOR | Ratios | |
|---|---|---|---|---|
| | % frequency | % frequency | N/T | T/N |
| Bladder | 0.0078 | 0.0256 | 0.3051 | 3.2777 |
| Breast | 0.0090 | 0.0113 | 0.7939 | 1.2595 |
| Small intestine | 0.0092 | 0.0000 | undef | 0.0000 |
| Ovary | 0.0090 | 0.0286 | 0.3140 | 3.1849 |
| Endocrine tissue | 0.0255 | 0.0050 | 5.0944 | 0.1963 |
| Gastrointestinal | 0.0096 | 0.0185 | 0.5177 | 1.9316 |
| Brain | 0.0044 | 0.0082 | 0.5400 | 1.8520 |
| Hematopoietic | 0.0134 | 0.0379 | 0.3529 | 2.8338 |
| Skin | 0.0073 | 0.0000 | undef | 0.0000 |
| Hepatic | 0.0285 | 0.0194 | 1.4706 | 0.6800 |
| Heart | 0.0042 | 0.0275 | 0.1542 | 6.4853 |
| Testicles | 0.0000 | 0.0117 | 0.0000 | undef |
| Lung | 0.0083 | 0.0184 | 0.4516 | 2.2144 |
| Stomach-esophagus | 0.0000 | 0.0077 | 0.0000 | undef |
| Muscle-skeleton | 0.0000 | 0.0060 | 0.0000 | undef |
| Kidney | 0.0109 | 0.0274 | 0.3965 | 2.5219 |
| Pancreas | 0.0017 | 0.0110 | 0.1496 | 6.6857 |
| Penis | 0.0060 | 0.0533 | 0.1123 | 8.9035 |
| Prostate | 0.0262 | 0.0192 | 1.3648 | 0.7327 |
| Uterus-endometrium | 0.0068 | 0.1583 | 0.0427 | 23.4317 |
| Uterus-myometrium | 0.0000 | 0.0068 | 0.0000 | undef |
| Uterus-general | 0.0000 | 0.0000 | undef | undef |
| Breast hyperplasia | 0.0128 | | | |
| Prostate hyperplasia | 0.0297 | | | |
| Seminal vesicle | 0.0356 | | | |
| Sensory organs | 0.0000 | | | |
| White blood cells | 0.0113 | | | |
| Cervix | 0.0000 | | | |

| | FETUS | STANDARDIZED/SUB-TRACTED LIBRARIES | |
|---|---|---|---|
| | % frequency | | % frequency |
| Development | 0.0278 | Breast | 0.0028 |
| Gastrointestinal | 0.0028 | Ovary_n | 0.0000 |
| Brain | 0.0188 | Ovary_t | 0.0152 |

-continued

| | | | |
|---|---|---|---|
| Hematopoietic | 0.0039 | Endocrine tissue | 0.0245 |
| Skin | 0.0000 | Fetal | 0.0064 |
| Hepatic | 0.0000 | Gastrointestinal | 0.0244 |
| Heart-blood vessels | 0.0107 | Hematopoietic | 0.0057 |
| Lung | 0.0000 | Skin-muscle | 0.0389 |
| Suprarenal gland | 0.0000 | Testicles | 0.0077 |
| Kidney | 0.0124 | Lung | 0.0000 |
| Placenta | 0.0182 | Nerves | 0.0080 |
| Prostate | 0.0000 | Prostate | 0.0274 |
| Sensory organs | 0.0126 | Sensory Organs | 0.0000 |
| | | Uterus_n | 0.0458 |

Electronic Northern for SEQ. ID NO.: 19

| | NORMAL | TUMOR | Ratios | |
|---|---|---|---|---|
| | % frequency | % frequency | N/T | T/N |
| Bladder | 0.0195 | 0.0102 | 1.9068 | 0.5244 |
| Breast | 0.0115 | 0.0132 | 0.8750 | 1.1429 |
| Small intestine | 0.0123 | 0.0165 | 0.7415 | 1.3487 |
| Ovary | 0.0060 | 0.0078 | 0.7675 | 1.3029 |
| Endocrine tissue | 0.0119 | 0.0125 | 0.9509 | 1.0516 |
| Gastrointestinal | 0.0096 | 0.0139 | 0.6903 | 1.4487 |
| Brain | 0.0096 | 0.0041 | 2.3399 | 0.4274 |
| Hematopoietic | 0.0080 | 0.0379 | 0.2117 | 4.7230 |
| Skin | 0.0330 | 0.2542 | 0.1300 | 7.6946 |
| Hepatic | 0.0048 | 0.0000 | undef | 0.0000 |
| Heart | 0.0127 | 0.0000 | undef | 0.0000 |
| Testicles | 0.0115 | 0.0468 | 0.2460 | 4.0652 |
| Lung | 0.0052 | 0.0082 | 0.6350 | 1.5747 |
| Stomach-esophagus | 0.0000 | 0.0153 | 0.0000 | undef |
| Muscle-skeleton | 0.0086 | 0.0060 | 1.4278 | 0.7004 |
| Kidney | 0.0081 | 0.0000 | undef | 0.0000 |
| Pancreas | 0.0050 | 0.0055 | 0.8974 | 1.1143 |
| Penis | 0.0150 | 0.0267 | 0.5616 | 1.7807 |
| Prostate | 0.0087 | 0.0106 | 0.8189 | 1.2211 |
| Uterus-endometrium | 0.0000 | 0.1055 | 0.0000 | undef |
| Uterus-myometrium | 0.0000 | 0.0000 | undef | undef |
| Uterus-general | 0.0458 | 0.0000 | undef | 0.0000 |
| Breast hyperplasia | 0.0384 | | | |
| Prostate hyperplasia | 0.0030 | | | |
| Seminal vesicle | 0.0000 | | | |
| Sensory organs | 0.0353 | | | |
| White blood cells | 0.0113 | | | |
| Cervix | 0.0000 | | | |

| | FETUS | STANDARDIZED/SUB-TRACTED LIBRARIES |
|---|---|---|
| | % frequency | % frequency |
| Development | 0.0139 | Breast 0.0136 |
| Gastrointestinal | 0.0056 | Ovary_n 0.0000 |
| Brain | 0.0000 | Ovary_t 0.0000 |
| Hematopoietic | 0.0000 | Endocrine tissue 0.0000 |
| Skin | 0.0000 | Fetal 0.0070 |
| Hepatic | 0.0000 | Gastrointestinal 0.0122 |
| Heart-blood vessels | 0.0036 | Hematopoietic 0.0000 |
| Lung | 0.0000 | Skin-muscle 0.0065 |
| Suprarenal gland | 0.0000 | Testicles 0.0077 |
| Kidney | 0.0000 | Lung 0.0000 |
| Placenta | 0.0121 | Nerves 0.0040 |
| Prostate | 0.0000 | Prostate 0.0000 |
| Sensory organs | 0.0000 | Sensory Organs 0.0077 |
| | | Uterus_n 0.0000 |

Electronic Northern for SEQ. ID NO.: 20

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0027 | 0.0000 | undef | 0.0000 |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.2111 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS | STANDARDIZED/SUB-TRACTED LIBRARIES |
|---|---|---|
| | % frequency | % frequency |
| Development | 0.0000 | Breast 0.0000 |
| Gastrointestinal | 0.0000 | Ovary_n 0.0000 |
| Brain | 0.0000 | Ovary_t 0.0000 |
| Hematopoietic | 0.0000 | Endocrine tissue 0.0000 |
| Skin | 0.0000 | Fetal 0.0000 |
| Hepatic | 0.0000 | Gastrointestinal 0.0000 |
| Heart-blood vessels | 0.0000 | Hematopoietic 0.0000 |
| Lung | 0.0000 | Skin-muscle 0.0000 |
| Suprarenal gland | 0.0000 | Testicles 0.0000 |
| Kidney | 0.0000 | Lung 0.0000 |
| Placenta | 0.0000 | Nerves 0.0000 |
| Prostate | 0.0000 | Prostate 0.0000 |
| Sensory organs | 0.0000 | Sensory Organs 0.0000 |
| | | Uterus_n 0.0000 |

Electronic Northern for SEQ. ID NO.: 21

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

|  | FETUS % frequency | STANDARDIZED/SUBTRACTED LIBRARIES % frequency |
|---|---|---|
| Development | 0.0000 | Breast 0.0000 |
| Gastrointestinal | 0.0000 | Ovary_n 0.0000 |
| Brain | 0.0000 | Ovary_t 0.0000 |
| Hematopoietic | 0.0000 | Endocrine tissue 0.0000 |
| Skin | 0.0000 | Fetal 0.0000 |
| Hepatic | 0.0000 | Gastrointestinal 0.0000 |
| Heart-blood vessels | 0.0000 | Hematopoietic 0.0000 |
| Lung | 0.0000 | Skin-muscle 0.0000 |
| Suprarenal gland | 0.0000 | Testicles 0.0000 |
| Kidney | 0.0000 | Lung 0.0000 |
| Placenta | 0.0000 | Nerves 0.0000 |
| Prostate | 0.0000 | Prostate 0.0000 |
| Sensory organs | 0.0000 | Sensory Organs 0.0000 |
|  |  | Uterus_n 0.0000 |

Electronic Northern for SEQ. ID NO.: 22

|  | NORMAL % frequency | TUMOR % frequency | Ratios N/T | Ratios T/N |
|---|---|---|---|---|
| Bladder | 0.0000 | 0.0128 | 0.0000 | undef |
| Breast | 0.0051 | 0.0075 | 0.6805 | 1.4694 |
| Small intestine | 0.0123 | 0.0000 | undef | 0.0000 |
| Ovary | 0.0060 | 0.0104 | 0.5756 | 1.7372 |
| Endocrine tissue | 0.0102 | 0.0125 | 0.8151 | 1.2268 |
| Gastrointestinal | 0.0172 | 0.0093 | 1.8638 | 0.5365 |
| Brain | 0.0052 | 0.0010 | 5.0397 | 0.1984 |
| Hematopoietic | 0.0027 | 0.0000 | undef | 0.0000 |
| Skin | 0.0000 | 0.0000 | undef | undef |
| Hepatic | 0.0000 | 0.0065 | 0.0000 | undef |
| Heart | 0.0201 | 0.0412 | 0.4883 | 2.0480 |
| Testicles | 0.0288 | 0.0234 | 1.2299 | 0.8130 |
| Lung | 0.0114 | 0.0184 | 0.6209 | 1.6105 |
| Stomach-esophagus | 0.0097 | 0.0077 | 1.2605 | 0.7933 |
| Muscle-skeleton | 0.0086 | 0.0180 | 0.4759 | 2.1012 |
| Kidney | 0.0217 | 0.0000 | undef | 0.0000 |
| Pancreas | 0.0149 | 0.0221 | 0.6731 | 1.4857 |
| Penis | 0.0150 | 0.0000 | undef | 0.0000 |
| Prostate | 0.0065 | 0.0170 | 0.3839 | 2.6051 |
| Uterus-endometrium | 0.0000 | 0.1055 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0192 |  |  |  |
| Prostate hyperplasia | 0.0149 |  |  |  |
| Seminal vesicle | 0.0000 |  |  |  |
| Sensory organs | 0.0118 |  |  |  |
| White blood cells | 0.0130 |  |  |  |
| Cervix | 0.0000 |  |  |  |

|  | FETUS % frequency | STANDARDIZED/SUBTRACTED LIBRARIES % frequency |
|---|---|---|
| Development | 0.0139 | Breast 0.0000 |
| Gastrointestinal | 0.0111 | Ovary_n 0.0000 |
| Brain | 0.0000 | Ovary_t 0.0203 |
| Hematopoietic | 0.0000 | Endocrine tissue 0.0000 |
| Skin | 0.0000 | Fetal 0.0052 |
| Hepatic | 0.0000 | Gastrointestinal 0.0244 |
| Heart-blood vessels | 0.0071 | Hematopoietic 0.0057 |
| Lung | 0.0072 | Skin-muscle 0.0227 |
| Suprarenal gland | 0.0000 | Testicles 0.0154 |
| Kidney | 0.0000 | Lung 0.0164 |
| Placenta | 0.0061 | Nerves 0.0030 |
| Prostate | 0.0249 | Prostate 0.0205 |
| Sensory organs | 0.0000 | Sensory Organs 0.0000 |
|  |  | Uterus_n 0.0125 |

Electronic Northern for SEQ. ID NO.: 23

|  | NORMAL % frequency | TUMOR % frequency | Ratios N/T | Ratios T/N |
|---|---|---|---|---|
| Bladder | 0.0078 | 0.0026 | 3.0509 | 0.3278 |
| Breast | 0.0026 | 0.0000 | undef | 0.0000 |
| Small intestine | 0.0184 | 0.0000 | undef | 0.0000 |
| Ovary | 0.0000 | 0.0026 | 0.0000 | undef |
| Endocrine tissue | 0.0017 | 0.0000 | undef | 0.0000 |
| Gastrointestinal | 0.0000 | 0.0000 | undef | undef |
| Brain | 0.0007 | 0.0041 | 0.1800 | 5.5559 |
| Hematopoietic | 0.0000 | 0.0000 | undef | undef |
| Skin | 0.0073 | 0.0000 | undef | 0.0000 |
| Hepatic | 0.0000 | 0.0000 | undef | undef |
| Heart | 0.0032 | 0.0137 | 0.2313 | 4.3235 |
| Testicles | 0.0000 | 0.0117 | 0.0000 | undef |
| Lung | 0.0021 | 0.0020 | 1.0161 | 0.9842 |
| Stomach-esophagus | 0.0097 | 0.0000 | undef | 0.0000 |
| Muscle-skeleton | 0.0000 | 0.0060 | 0.0000 | undef |
| Kidney | 0.0000 | 0.0205 | 0.0000 | undef |
| Pancreas | 0.0066 | 0.0055 | 1.1966 | 0.8357 |
| Penis | 0.0120 | 0.0000 | undef | 0.0000 |
| Prostate | 0.0000 | 0.0000 | undef | undef |
| Uterus-endometrium | 0.0000 | 0.1055 | 0.0000 | undef |
| Uterus-myometrium | 0.0076 | 0.0068 | 1.1223 | 0.8911 |
| Uterus-general | 0.0051 | 0.0000 | undef | 0.0000 |
| Breast hyperplasia | 0.0096 |  |  |  |
| Prostate hyperplasia | 0.0030 |  |  |  |
| Seminal vesicle | 0.0000 |  |  |  |
| Sensory organs | 0.0000 |  |  |  |
| White blood cells | 0.0017 |  |  |  |
| Cervix | 0.0106 |  |  |  |

|  | FETUS % frequency | STANDARDIZED/SUBTRACTED LIBRARIES % frequency |
|---|---|---|
| Development | 0.0000 | Breast 0.0000 |
| Gastrointestinal | 0.0028 | Ovary_n 0.0000 |
| Brain | 0.0063 | Ovary_t 0.0000 |
| Hematopoietic | 0.0000 | Endocrine tissue 0.0000 |
| Skin | 0.0000 | Fetal 0.0029 |
| Hepatic | 0.0000 | Gastrointestinal 0.0000 |
| Heart-blood vessels | 0.0000 | Hematopoietic 0.0000 |
| Lung | 0.0072 | Skin-muscle 0.0000 |
| Suprarenal gland | 0.0000 | Testicles 0.0154 |
| Kidney | 0.0000 | Lung 0.0000 |
| Placenta | 0.0000 | Nerves 0.0030 |
| Prostate | 0.0000 | Prostate 0.0000 |
| Sensory organs | 0.0000 | Sensory Organs 0.0000 |
|  |  | Uterus_n 0.0083 |

Electronic Northern for SEQ. ID NO.: 24

|  | NORMAL % frequency | TUMOR % frequency | Ratios N/T | Ratios T/N |
|---|---|---|---|---|
| Bladder | 0.0000 | 0.0077 | 0.0000 | undef |
| Breast | 0.0064 | 0.0019 | 3.4026 | 0.2939 |
| Small intestine | 0.0031 | 0.0000 | undef | 0.0000 |
| Ovary | 0.0030 | 0.0000 | undef | 0.0000 |
| Endocrine tissue | 0.0068 | 0.0025 | 2.7170 | 0.3681 |
| Gastrointestinal | 0.0019 | 0.0000 | undef | 0.0000 |
| Brain | 0.0118 | 0.0031 | 3.8398 | 0.2604 |
| Hematopoietic | 0.0053 | 0.0000 | undef | 0.0000 |
| Skin | 0.0000 | 0.0000 | undef | undef |
| Hepatic | 0.0000 | 0.0000 | undef | undef |
| Heart | 0.0042 | 0.0000 | undef | 0.0000 |
| Testicles | 0.0000 | 0.0000 | undef | undef |
| Lung | 0.0010 | 0.0020 | 0.5080 | 1.9684 |
| Stomach-esophagus | 0.0000 | 0.0077 | 0.0000 | undef |
| Muscle-skeleton | 0.0000 | 0.0000 | undef | undef |
| Kidney | 0.0109 | 0.0000 | undef | 0.0000 |
| Pancreas | 0.0017 | 0.0000 | undef | 0.0000 |
| Penis | 0.0030 | 0.0000 | undef | 0.0000 |
| Prostate | 0.0044 | 0.0085 | 0.5118 | 1.9538 |

| | | | | |
|---|---|---|---|---|
| Uterus-endometrium | 0.0000 | 0.1583 | 0.0000 | undef |
| Uterus-myometrium | 0.0000 | 0.0000 | undef | undef |
| Uterus-general | 0.0051 | 0.0000 | undef | 0.0000 |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0136 |
| Gastrointestinal | 0.0000 | Ovary_n | 0.0000 |
| Brain | 0.0063 | Ovary_t | 0.0000 |
| Hematopoietic | 0.0039 | Endocrine tissue | 0.0000 |
| Skin | 0.0000 | Fetal | 0.0111 |
| Hepatic | 0.0000 | Gastrointestinal | 0.0000 |
| Heart-blood vessels | 0.0036 | Hematopoietic | 0.0000 |
| Lung | 0.0000 | Skin-muscle | 0.0194 |
| Suprarenal gland | 0.0000 | Testicles | 0.0000 |
| Kidney | 0.0000 | Lung | 0.0082 |
| Placenta | 0.0000 | Nerves | 0.0080 |
| Prostate | 0.0000 | Prostate | 0.0000 |
| Sensory organs | 0.0377 | Sensory Organs | 0.0000 |
| | | Uterus_n | 0.0000 |

Electronic Northern for SEQ. ID NO.: 25

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0064 | 0.0000 | undef | 0.0000 |
| Small intestine | 0.0000 | 0.0000 | undef | undef |
| Ovary | 0.0030 | 0.0026 | 1.1513 | 0.8686 |
| Endocrine tissue | 0.0000 | 0.0000 | undef | undef |
| Gastrointestinal | 0.0019 | 0.0000 | undef | 0.0000 |
| Brain | 0.0000 | 0.0000 | undef | undef |
| Hematopoietic | 0.0000 | 0.0000 | undef | undef |
| Skin | 0.0110 | 0.0000 | undef | 0.0000 |
| Hepatic | 0.0048 | 0.0000 | undef | 0.0000 |
| Heart | 0.0042 | 0.0000 | undef | 0.0000 |
| Testicles | 0.0000 | 0.0000 | undef | undef |
| Lung | 0.0000 | 0.0041 | 0.0000 | undef |
| Stomach-esophagus | 0.0097 | 0.0000 | undef | 0.0000 |
| Muscle-skeleton | 0.0051 | 0.0000 | undef | 0.0000 |
| Kidney | 0.0027 | 0.0000 | undef | 0.0000 |
| Pancreas | 0.0017 | 0.0000 | undef | 0.0000 |
| Penis | 0.0030 | 0.0000 | undef | 0.0000 |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0064 | | | |
| Prostate hyperplasia | 0.0000 | | | |
| Seminal vesicle | 0.0089 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0052 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 26

| | NORMAL | TUMOR | Ratios | |
|---|---|---|---|---|
| | % frequency | % frequency | N/T | T/N |
| Bladder | 0.0117 | 0.0102 | 1.1441 | 0.8741 |
| Breast | 0.0038 | 0.0038 | 1.0208 | 0.9796 |
| Small intestine | 0.0061 | 0.0000 | undef | 0.0000 |
| Ovary | 0.0000 | 0.0026 | 0.0000 | undef |
| Endocrine tissue | 0.0051 | 0.0025 | 2.0377 | 0.4907 |
| Gastrointestinal | 0.0038 | 0.0185 | 0.2071 | 4.8289 |
| Brain | 0.0037 | 0.0031 | 1.1999 | 0.8334 |
| Hematopoietic | 0.0027 | 0.0000 | undef | 0.0000 |
| Skin | 0.0000 | 0.0000 | undef | undef |
| Hepatic | 0.0095 | 0.0065 | 1.4706 | 0.6800 |
| Heart | 0.0011 | 0.0000 | undef | 0.0000 |
| Testicles | 0.0000 | 0.0000 | undef | undef |
| Lung | 0.0062 | 0.0041 | 1.5241 | 0.6561 |
| Stomach-esophagus | 0.0000 | 0.0000 | undef | undef |
| Muscle-skeleton | 0.0017 | 0.0000 | undef | 0.0000 |
| Kidney | 0.0136 | 0.0068 | 1.9826 | 0.5044 |
| Pancreas | 0.0000 | 0.0110 | 0.0000 | undef |
| Penis | 0.0030 | 0.0000 | undef | 0.0000 |
| Prostate | 0.0044 | 0.0021 | 2.0473 | 0.4885 |
| Uterus-endometrium | 0.0068 | 0.1055 | 0.0640 | 15.6211 |
| Uterus-myometrium | 0.0000 | 0.0000 | undef | undef |
| Uterus-general | 0.0102 | 0.0954 | 0.1067 | 9.3678 |
| Breast hyperplasia | 0.0000 | | | |
| Prostate hyperplasia | 0.0030 | | | |
| Seminal vesicle | 0.0000 | | | |
| Sensory organs | 0.0118 | | | |
| White blood cells | 0.0026 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0056 | Ovary_n | 0.0000 |
| Brain | 0.0000 | Ovary_t | 0.0101 |
| Hematopoietic | 0.0000 | Endocrine tissue | 0.0000 |
| Skin | 0.0000 | Fetal | 0.0140 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0680 |
| Suprarenal gland | 0.0000 | Testicles | 0.0000 |
| Kidney | 0.0000 | Lung | 0.0000 |
| Placenta | 0.0000 | Nerves | 0.0070 |
| Prostate | 0.0000 | Prostate | 0.0068 |
| Sensory organs | 0.0000 | Sensory Organs | 0.0000 |
| | | Uterus_n | 0.0042 |

Electronic Northern for SEQ. ID NO.: 27

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0030 | 0.0026 | 1.1513 | 0.8686 |
| Endocrine tissue | 0.0000 | 0.0125 | 0.0000 | undef |
| Gastrointestinal | 0.0019 | 0.0000 | undef | 0.0000 |
| Brain | 0.0059 | 0.0041 | 1.4399 | 0.6945 |
| Hematopoietic | 0.0000 | 0.0000 | undef | undef |
| Skin | 0.0037 | 0.0000 | undef | 0.0000 |
| Hepatic | 0.0000 | 0.0063 | 0.0000 | undef |
| Heart | 0.0011 | 0.0000 | undef | 0.0000 |
| Testicles | 0.0058 | 0.0000 | undef | 0.0000 |
| Lung | 0.0010 | 0.0020 | 0.5080 | 1.9684 |
| Stomach-esophagus | 0.0000 | 0.0000 | undef | undef |
| Muscle-skeleton | 0.0000 | 0.0000 | undef | undef |

| | -continued | | | |
|---|---|---|---|---|
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0044 | 0.0000 | undef | 0.0000 |
| Uterus-endometrium | 0.0068 | 0.1055 | 0.0640 | 15.6211 |
| Uterus-myometrium | 0.0076 | 0.0068 | 1.1223 | 0.8911 |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0000 | | | |
| Sensory organs | 0.0118 | | | |
| White blood cells | 0.0009 | | | |
| Cervix | 0.0000 | | | |

| | FETUS<br>% frequency | STANDARDIZED/SUB-<br>TRACTED LIBRARIES<br>% frequency |
|---|---|---|
| Development | 0.0139 | Breast 0.0204 |
| Gastrointestinal | 0.0000 | Ovary_n 0.0000 |
| Brain | 0.0000 | Ovary_t 0.0051 |
| Hematopoietic | 0.0000 | Endocrine tissue 0.0000 |
| Skin | 0.0000 | Fetal 0.0064 |
| Hepatic | 0.0000 | Gastrointestinal 0.0000 |
| Heart-blood vessels | 0.0036 | Hematopoietic 0.0000 |
| Lung | 0.0000 | Skin-muscle 0.0032 |
| Suprarenal gland | 0.0000 | Testicles 0.0000 |
| Kidney | 0.0000 | Lung 0.0000 |
| Placenta | 0.0000 | Nerves 0.0020 |
| Prostate | 0.0000 | Prostate 0.0000 |
| Sensory organs | 0.0000 | Sensory Organs 0.0232 |
| | | Uterus_n 0.0083 |

Electronic Northern for SEQ. ID NO.: 28

| | NORMAL | TUMOR | Ratios | |
|---|---|---|---|---|
| | % frequency | % frequency | N/T | T/N |
| Bladder | 0.0000 | 0.0051 | 0.0000 | undef |
| Breast | 0.0153 | 0.0094 | 1.6333 | 0.6123 |
| Small intestine | 0.0000 | 0.0000 | undef | undef |
| Ovary | 0.0030 | 0.0130 | 0.2303 | 4.3431 |
| Endocrine tissue | 0.0034 | 0.0025 | 1.3585 | 0.7361 |
| Gastrointestinal | 0.0019 | 0.0000 | undef | 0.0000 |
| Brain | 0.0030 | 0.0000 | undef | 0.0000 |
| Hematopoietic | 0.0000 | 0.0000 | undef | undef |
| Skin | 0.0184 | 0.0000 | undef | 0.0000 |
| Hepatic | 0.0048 | 0.0000 | undef | 0.0000 |
| Heart | 0.0074 | 0.0000 | undef | 0.0000 |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0086 | 0.0060 | 1.4278 | 0.7004 |
| Kidney | 0.0027 | 0.0000 | undef | 0.0000 |
| Pancreas | 0.0033 | 0.0000 | undef | 0.0000 |
| Penis | 0.0030 | 0.0000 | undef | 0.0000 |
| Prostate | 0.0000 | 0.0000 | undef | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0256 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

| | FETUS<br>% frequency | STANDARDIZED/SUB-<br>TRACTED LIBRARIES<br>% frequency |
|---|---|---|
| Development | 0.0000 | Breast 0.0204 |
| Gastrointestinal | 0.0028 | Ovary_n 0.0000 |
| Brain | 0.0000 | Ovary_t 0.0000 |
| Hematopoietic | 0.0000 | Endocrine tissue 0.0000 |
| Skin | 0.0000 | Fetal 0.0105 |
| Hepatic | 0.0520 | Gastrointestinal 0.0000 |
| Heart-blood vessels | 0.0000 | Hematopoietic 0.0171 |
| Lung | 0.0000 | Skin-muscle 0.0162 |
| Suprarenal gland | 0.0000 | Testicles 0.0000 |
| Kidney | 0.0062 | Lung 0.0000 |
| Placenta | 0.0000 | Nerves 0.0060 |
| Prostate | 0.0000 | Prostate 0.0000 |
| Sensory organs | 0.0000 | Sensory Organs 0.0000 |
| | | Uterus_n 0.0167 |

Electronic Northern for SEQ. ID NO.: 29

| | NORMAL | TUMOR | Ratios | |
|---|---|---|---|---|
| | % frequency | % frequency | N/T | T/N |
| Bladder | 0.0000 | 0.0128 | 0.0000 | undef |
| Breast | 0.0013 | 0.0038 | 0.3403 | 2.9389 |
| Small intestine | 0.0031 | 0.0000 | undef | 0.0000 |
| Ovary | 0.0000 | 0.0078 | 0.0000 | undef |
| Endocrine tissue | 0.0034 | 0.0025 | 1.3585 | 0.7361 |
| Gastrointestinal | 0.0038 | 0.0046 | 0.8283 | 1.2072 |
| Brain | 0.0000 | 0.0000 | undef | undef |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0061 | 0.0000 | undef |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0017 | 0.0000 | undef | 0.0000 |
| Penis | 0.0000 | 0.0000 | undef | undef |
| Prostate | 0.0022 | 0.0085 | 0.2559 | 3.9077 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0096 | | | |
| Prostate hyperplasia | 0.0119 | | | |
| Seminal vesicle | 0.0089 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency |
|---|---|---|
| Development | 0.0000 | Breast 0.0000 |
| Gastrointestinal | 0.0028 | Ovary_n 0.0000 |
| Brain | 0.0000 | Ovary_t 0.0051 |
| Hematopoietic | 0.0000 | Endocrine tissue 0.0000 |
| Skin | 0.0000 | Fetal 0.0012 |
| Hepatic | 0.0000 | Gastrointestinal 0.0000 |
| Heart-blood vessels | 0.0000 | Hematopoietic 0.0000 |
| Lung | 0.0000 | Skin-muscle 0.0000 |
| Suprarenal gland | 0.0000 | Testicles 0.0000 |
| Kidney | 0.0000 | Lung 0.0082 |
| Placenta | 0.0000 | Nerves 0.0000 |
| Prostate | 0.0000 | Prostate 0.0137 |
| Sensory organs | 0.0000 | Sensory Organs 0.0000 |
| | | Uterus_n 0.0000 |

Electronic Northern for SEQ. ID NO.: 30

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0026 | 0.0019 | 1.3611 | 0.7347 |
| Small intestine | 0.0000 | 0.0000 | undef | undef |
| Ovary | 0.0000 | 0.0104 | 0.0000 | undef |
| Endocrine tissue | 0.0034 | 0.0025 | 1.3585 | 0.7361 |
| Gastrointestinal | 0.0038 | 0.0000 | undef | 0.0000 |
| Brain | 0.0022 | 0.0010 | 2.1599 | 0.4630 |
| Hematopoietic | 0.0000 | 0.0000 | undef | undef |
| Skin | 0.0000 | 0.0000 | undef | undef |
| Hepatic | 0.0048 | 0.0000 | undef | 0.0000 |
| Heart | 0.0032 | 0.0000 | undef | 0.0000 |

-continued

| | | | |
|---|---|---|---|
| Testicles | 0.0000 | 0.0000 | undef | undef |
| Lung | 0.0021 | 0.0020 | 1.0161 | 0.9842 |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0044 | 0.0064 | 0.6824 | 1.4654 |
| Uterus-endometrium | 0.0135 | 0.1055 | 0.1280 | 7.8106 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0089 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0082 |
| Placenta | 0.0000 | Nerves | 0.0020 |
| Prostate | 0.0000 | Prostate | 0.0000 |
| Sensory organs | 0.0000 | Sensory Organs | 0.0000 |
| | | Uterus_n | 0.0167 |

Electronic Northern for SEQ. ID NO.: 31

| | NORMAL % frequency | TUMOR % frequency | Ratios N/T | T/N |
|---|---|---|---|---|
| Bladder | 0.0039 | 0.0026 | 1.5254 | 0.6555 |
| Breast | 0.0013 | 0.0056 | 0.2268 | 4.4083 |
| Small intestine | 0.0061 | 0.0000 | undef | 0.0000 |
| Ovary | 0.0000 | 0.0078 | 0.0000 | undef |
| Endocrine tissue | 0.0017 | 0.0050 | 0.3396 | 2.9444 |
| Gastrointestinal | 0.0038 | 0.0046 | 0.8283 | 1.2072 |
| Brain | 0.0037 | 0.0041 | 0.8999 | 1.1112 |
| Hematopoietic | 0.0067 | 0.0000 | undef | 0.0000 |
| Skin | 0.0000 | 0.0000 | undef | undef |
| Hepatic | 0.0000 | 0.0065 | 0.0000 | undef |
| Heart | 0.0074 | 0.0000 | undef | 0.0000 |
| Testicles | 0.0000 | 0.0117 | 0.0000 | undef |
| Lung | 0.0042 | 0.0041 | 1.0161 | 0.9842 |
| Stomach-esophagus | 0.0000 | 0.0077 | 0.0000 | undef |
| Muscle-skeleton | 0.0034 | 0.0060 | 0.5711 | 1.7510 |
| Kidney | 0.0027 | 0.0137 | 0.1983 | 5.0439 |
| Pancreas | 0.0017 | 0.0000 | undef | 0.0000 |
| Penis | 0.0000 | 0.0267 | 0.0000 | undef |
| Prostate | 0.0022 | 0.0000 | undef | 0.0000 |
| Uterus-endometrium | 0.0000 | 0.1055 | 0.0000 | undef |
| Uterus-myometrium | 0.0076 | 0.0000 | undef | 0.0000 |
| Uterus-general | 0.0000 | 0.0000 | undef | undef |
| Breast hyperplasia | 0.0224 | | | |
| Prostate hyperplasia | 0.0030 | | | |
| Seminal vesicle | 0.0000 | | | |
| Sensory organs | 0.0000 | | | |
| White blood cells | 0.0035 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0051 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0036 | Hematopoietic | 0.0000 |
| Lung | 0.0036 | Skin-muscle | 0.0000 |
| Suprarenal gland | 0.0000 | Testicles | 0.0077 |
| Kidney | 0.0000 | Lung | 0.0082 |
| Placenta | 0.0182 | Nerves | 0.0010 |
| Prostate | 0.0000 | Prostate | 0.0068 |
| Sensory organs | 0.0000 | Sensory Organs | 0.0000 |
| | | Uterus_n | 0.0042 |

Electronic Northern for SEQ. ID NO.: 32

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0038 | 0.0000 | undef |
| Small intestine | 0.0031 | 0.0000 | undef | 0.0000 |
| Ovary | 0.0000 | 0.0000 | undef | undef |
| Endocrine tissue | 0.0068 | 0.0050 | 1.3585 | 0.7361 |
| Gastrointestinal | 0.0038 | 0.0000 | undef | 0.0000 |
| Brain | 0.0022 | 0.0041 | 0.5400 | 1.8520 |
| Hematopoietic | 0.0027 | 0.0000 | undef | 0.0000 |
| Skin | 0.0000 | 0.0000 | undef | undef |
| Hepatic | 0.0048 | 0.0129 | 0.3676 | 2.7200 |
| Heart | 0.0032 | 0.0000 | undef | 0.0000 |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0000 | 0.0000 | undef | undef |
| Kidney | 0.0054 | 0.0000 | undef | 0.0000 |
| Pancreas | 0.0000 | 0.0110 | 0.0000 | undef |
| Penis | 0.0000 | 0.0000 | undef | undef |
| Prostate | 0.0022 | 0.0043 | 0.5118 | 1.9538 |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0036 | Hematopoietic | 0.0000 |
| Lung | 0.0000 | Skin-muscle | 0.0000 |
| Suprarenal gland | 0.0000 | Testicles | 0.0000 |
| Kidney | 0.0062 | Lung | 0.0000 |
| Placenta | 0.0000 | Nerves | 0.0020 |
| Prostate | 0.0249 | Prostate | 0.0000 |
| Sensory organs | 0.0000 | Sensory Organs | 0.0000 |
| | | Uterus_n | 0.0000 |

Electronic Northern for SEQ. ID NO.: 33

| | NORMAL % frequency | TUMOR % frequency | Ratios N/T | T/N |
|---|---|---|---|---|
| Bladder | 0.0000 | 0.0000 | undef | undef |
| Breast | 0.0013 | 0.0000 | undef | 0.0000 |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |

-continued

| | | | |
|---|---|---|---|
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0017 | 0.0000 | undef | 0.0000 |
| Penis | 0.0000 | 0.0000 | undef | undef |
| Prostate | 0.0000 | 0.0000 | undef | undef |
| Uterus-endometrium | 0.0068 | 0.2639 | 0.0256 | 39.0528 |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0154 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 34

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0010 | 0.0000 | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0060 | 0.0000 | undef |
| Kidney | 0.0000 | 0.0068 | 0.0000 | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 35

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0026 | 0.0038 | 0.6805 | 1.4694 |
| Small intestine | 0.0000 | 0.0165 | 0.0000 | undef |
| Ovary | 0.0000 | 0.0026 | 0.0000 | undef |
| Endocrine tissue | 0.0034 | 0.0000 | undef | 0.0000 |
| Gastrointestinal | 0.0057 | 0.0000 | undef | 0.0000 |
| Brain | 0.0007 | 0.0021 | 0.3600 | 2.7779 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0032 | 0.0000 | undef | 0.0000 |
| Testicles | 0.0000 | 0.0000 | undef | undef |
| Lung | 0.0010 | 0.0082 | 0.1270 | 7.8735 |
| Stomach-esophagus | 0.0000 | 0.0077 | 0.0000 | undef |
| Muscle-skeleton | 0.0034 | 0.0000 | undef | 0.0000 |
| Kidney | 0.0081 | 0.0479 | 0.1699 | 5.8845 |
| Pancreas | 0.0000 | 0.0000 | undef | undef |
| Penis | 0.0060 | 0.0000 | undef | 0.0000 |
| Prostate | 0.0044 | 0.0021 | 2.0473 | 0.4885 |
| Uterus-endometrium | 0.0068 | 0.2639 | 0.0256 | 39.0528 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0059 | | | |
| Seminal vesicle | 0.0089 | | | |
| Sensory organs | 0.0000 | | | |
| White blood cells | 0.0052 | | | |
| Cervix | 0.0000 | | | |

| | FETUS % frequency | STANDARDIZED/SUB- TRACTED LIBRARIES % frequency | |
|---|---|---|---|
| Development | 0.0000 | Breast | 0.0340 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0029 |
| Hepatic | 0.0000 | Gastrointestinal | 0.0000 |
| Heart-blood vessels | 0.0000 | Hematopoietic | 0.0171 |
| Lung | 0.0036 | Skin-muscle | 0.0000 |
| Suprarenal gland | 0.0000 | Testicles | 0.0000 |
| Kidney | 0.0000 | Lung | 0.0246 |
| Placenta | 0.0000 | Nerves | 0.0030 |
| Prostate | 0.0000 | Prostate | 0.0000 |
| Sensory organs | 0.0000 | Sensory Organs | 0.0000 |
| | | Uterus_n | 0.0083 |

Electronic Northern for SEQ. ID NO.: 36

|  | NORMAL | TUMOR | Ratios | |
|---|---|---|---|---|
|  | % frequency | % frequency | N/T | T/N |
| Bladder | 0.0000 | 0.0026 | 0.0000 | undef |
| Breast | 0.0038 | 0.0019 | 2.0416 | 0.4898 |
| Small intestine | 0.0031 | 0.0000 | undef | 0.0000 |
| Ovary | 0.0000 | 0.0000 | undef | undef |
| Endocrine tissue | 0.0034 | 0.0000 | undef | 0.0000 |
| Gastrointestinal | 0.0057 | 0.0000 | undef | 0.0000 |
| Brain | 0.0015 | 0.0010 | 1.4399 | 0.6945 |
| Hematopoietic | 0.0040 | 0.0000 | undef | 0.0000 |
| Skin | 0.0037 | 0.0000 | undef | 0.0000 |
| Hepatic | 0.0000 | 0.0129 | 0.0000 | undef |
| Heart | 0.0000 | 0.0000 | undef | undef |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0000 | 0.0120 | 0.0000 | undef |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0032 |  |  |  |
| Prostate hyperplasia | 0.0000 |  |  |  |
| Seminal vesicle | 0.0000 |  |  |  |
| Sensory organs | 0.0000 |  |  |  |
| White blood cells | 0.0035 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0000 |
| Hepatic | 0.0000 | Gastrointestinal | 0.0122 |
| Heart-blood vessels | 0.0000 | Hematopoietic | 0.0000 |
| Lung | 0.0000 | Skin-muscle | 0.0032 |
| Suprarenal gland | 0.0000 | Testicles | 0.0000 |
| Kidney | 0.0000 | Lung | 0.0000 |
| Placenta | 0.0000 | Nerves | 0.0030 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 37

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0010 | 0.0000 | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0044 | 0.0021 | 2.0473 | 0.4885 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0032 |  |  |  |
| Prostate hyperplasia | 0.0000 |  |  |  |
| Seminal vesicle | 0.0000 |  |  |  |
| Sensory organs | 0.0118 |  |  |  |
| White blood cells | 0.0000 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 38

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0030 | 0.0000 | undef | 0.0000 |
| Endocrine tissue | 0.0034 | 0.0000 | undef | 0.0000 |
| Gastrointestinal | 0.0019 | 0.0000 | undef | 0.0000 |
| Brain | 0.0007 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0058 | 0.0000 | undef | 0.0000 |
| Lung | 0.0000 | 0.0000 | undef | undef |
| Stomach-esophagus | 0.0000 | 0.0000 | undef | undef |
| Muscle-skeleton | 0.0069 | 0.0120 | 0.5711 | 1.7510 |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0000 | 0.0000 | undef | undef |
| Uterus-endometrium | 0.0000 | 0.1055 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0032 |  |  |  |
| Prostate hyperplasia | 0.0000 |  |  |  |
| Seminal vesicle | 0.0000 |  |  |  |
| Sensory organs | 0.0000 |  |  |  |
| White blood cells | 0.0000 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0139 | Breast | 0.0000 |
| Gastrointestinal | 0.0000 | Ovary_n | 0.0000 |
| Brain | 0.0063 | Ovary_t | 0.0000 |
| Hematopoietic | 0.0000 | Endocrine tissue | 0.0000 |
| Skin | 0.0000 | Fetal | 0.0023 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0032 |
| Suprarenal gland | 0.0000 | Testicles | 0.0077 |
| Kidney | 0.0000 | Lung | 0.0000 |
| Placenta | 0.0000 | Nerves | 0.0030 |

-continued

| | | | | |
|---|---|---|---|---|
| Prostate | 0.0000 | Prostate | | 0.0000 |
| Sensory organs | 0.0000 | Sensory Organs | | 0.0077 |
| | | Uterus_n | | 0.0000 |

Electronic Northern for SEQ. ID NO.: 39

| | NORMAL | TUMOR | Ratios | |
|---|---|---|---|---|
| | % frequency | % frequency | N/T | T/N |
| Bladder | 0.0000 | 0.0051 | 0.0000 | undef |
| Breast | 0.0013 | 0.0038 | 0.3403 | 2.9389 |
| Small intestine | 0.0000 | 0.0000 | undef | undef |
| Ovary | 0.0030 | 0.0052 | 0.5756 | 1.7372 |
| Endocrine tissue | 0.0000 | 0.0075 | 0.0000 | undef |
| Gastrointestinal | 0.0019 | 0.0046 | 0.4142 | 2.4145 |
| Brain | 0.0000 | 0.0010 | 0.0000 | undef |
| Hematopoietic | 0.0000 | 0.0000 | undef | undef |
| Skin | 0.0404 | 0.0000 | undef | 0.0000 |
| Hepatic | 0.0000 | 0.0065 | 0.0000 | undef |
| Heart | 0.0000 | 0.0000 | undef | undef |
| Testicles | 0.0000 | 0.0000 | undef | undef |
| Lung | 0.0073 | 0.0020 | 3.5562 | 0.2812 |
| Stomach-esophagus | 0.0000 | 0.0000 | undef | undef |
| Muscle-skeleton | 0.0000 | 0.0000 | undef | undef |
| Kidney | 0.0000 | 0.0068 | 0.0000 | undef |
| Pancreas | 0.0050 | 0.0055 | 0.8974 | 1.1143 |
| Penis | 0.0269 | 0.1066 | 0.2527 | 3.9571 |
| Prostate | 0.0022 | 0.0021 | 1.0236 | 0.9769 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0064 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0106 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0101 |
| Hematopoietic | 0.0000 | Endocrine tissue | 0.0000 |
| Skin | 0.0000 | Fetal | 0.0064 |
| Hepatic | 0.0000 | Gastrointestinal | 0.0000 |
| Heart-blood vessels | 0.0036 | Hematopoietic | 0.0000 |
| Lung | 0.0108 | Skin-muscle | 0.0000 |
| Suprarenal gland | 0.0000 | Testicles | 0.0000 |
| Kidney | 0.0062 | Lung | 0.0082 |
| Placenta | 0.0000 | Nerves | 0.0000 |
| Prostate | 0.0000 | Prostate | 0.0068 |
| Sensory organs | 0.0000 | Sensory Organs | 0.0000 |
| | | Uterus_n | 0.0042 |

Electronic Northern for SEQ. ID NO.: 40

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0000 | 0.0019 | 0.0000 | undef |
| Small intestine | 0.0184 | 0.0000 | undef | 0.0000 |
| Ovary | 0.0030 | 0.0156 | 0.1919 | 5.2117 |
| Endocrine tissue | 0.0000 | 0.0000 | undef | undef |
| Gastrointestinal | 0.0096 | 0.0231 | 0.4142 | 2.4145 |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0065 | 0.0000 | undef |
| Heart | 0.0000 | 0.0000 | undef | undef |
| Testicles | 0.0000 | 0.0000 | undef | undef |
| Lung | 0.0010 | 0.0000 | undef | 0.0000 |
| Stomach-esophagus | 0.0000 | 0.0077 | 0.0000 | undef |
| Muscle-skeleton | 0.0000 | 0.0000 | undef | undef |
| Kidney | 0.0027 | 0.0068 | 0.3965 | 2.5219 |
| Pancreas | 0.0083 | 0.0000 | undef | 0.0000 |
| Penis | 0.0000 | 0.0000 | undef | undef |
| Prostate | 0.0022 | 0.0106 | 0.2047 | 4.8846 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0064 | | | |
| Prostate hyperplasia | 0.0089 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0139 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0047 |
| Hepatic | 0.0000 | Gastrointestinal | 0.0000 |
| Heart-blood vessels | 0.0000 | Hematopoietic | 0.0000 |
| Lung | 0.0072 | Skin-muscle | 0.0000 |
| Suprarenal gland | 0.0000 | Testicles | 0.0000 |
| Kidney | 0.0000 | Lung | 0.0082 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 41

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0057 |

-continued

| | | | | |
|---|---|---|---|---|
| Lung | 0.0000 | Skin-muscle | | 0.0000 |
| Suprarenal gland | 0.0000 | Testicles | | 0.0000 |
| Kidney | 0.0000 | Lung | | 0.0000 |
| Placenta | 0.0000 | Nerves | | 0.0000 |
| Prostate | 0.0000 | Prostate | | 0.0000 |
| Sensory organs | 0.0000 | Sensory Organs | | 0.0000 |
| | | Uterus_n | | 0.0000 |

Electronic Northern for SEQ. ID NO.: 42

| | NORMAL | TUMOR | Ratios | |
|---|---|---|---|---|
| | % frequency | % frequency | N/T | T/N |
| Bladder | 0.0156 | 0.0077 | 2.0339 | 0.4917 |
| Breast | 0.0051 | 0.0113 | 0.4537 | 2.2042 |
| Small intestine | 0.0092 | 0.0165 | 0.5561 | 1.7982 |
| Ovary | 0.0000 | 0.0208 | 0.0000 | undef |
| Endocrine tissue | 0.0136 | 0.0251 | 0.5434 | 1.8403 |
| Gastrointestinal | 0.0153 | 0.0185 | 0.8283 | 1.2072 |
| Brain | 0.0118 | 0.0041 | 2.8798 | 0.3472 |
| Hematopoietic | 0.0067 | 0.0000 | undef | 0.0000 |
| Skin | 0.0073 | 0.0000 | undef | 0.0000 |
| Hepatic | 0.0095 | 0.0129 | 0.7353 | 1.3600 |
| Heart | 0.0064 | 0.0275 | 0.2313 | 4.3235 |
| Testicles | 0.0000 | 0.0234 | 0.0000 | undef |
| Lung | 0.0187 | 0.0164 | 1.1431 | 0.8748 |
| Stomach-esophagus | 0.0000 | 0.0000 | undef | undef |
| Muscle-skeleton | 0.0069 | 0.0060 | 1.1422 | 0.8755 |
| Kidney | 0.0081 | 0.0205 | 0.3965 | 2.5219 |
| Pancreas | 0.0182 | 0.0055 | 3.2906 | 0.3039 |
| Penis | 0.0120 | 0.0267 | 0.4493 | 2.2259 |
| Prostate | 0.0131 | 0.0213 | 0.6142 | 1.6282 |
| Uterus-endometrium | 0.0135 | 0.1583 | 0.0854 | 11.7158 |
| Uterus-myometrium | 0.0000 | 0.0000 | undef | undef |
| Uterus-general | 0.0000 | 0.0000 | undef | undef |
| Breast hyperplasia | 0.0192 | | | |
| Prostate hyperplasia | 0.0089 | | | |
| Seminal vesicle | 0.0089 | | | |
| Sensory organs | 0.0000 | | | |
| White blood cells | 0.0199 | | | |
| Cervix | 0.0106 | | | |

| | FETUS % frequency | STANDARDIZED/SUB-TRACTED LIBRARIES % frequency | |
|---|---|---|---|
| Development | 0.0000 | Breast | 0.0204 |
| Gastrointestinal | 0.0028 | Ovary_n | 0.0000 |
| Brain | 0.0000 | Ovary_t | 0.0101 |
| Hematopoietic | 0.0039 | Endocrine tissue | 0.0490 |
| Skin | 0.0000 | Fetal | 0.0122 |
| Hepatic | 0.0000 | Gastrointestinal | 0.0000 |
| Heart-blood vessels | 0.0071 | Hematopoietic | 0.0399 |
| Lung | 0.0072 | Skin-muscle | 0.0454 |
| Suprarenal gland | 0.0000 | Testicles | 0.0231 |
| Kidney | 0.0000 | Lung | 0.0082 |
| Placenta | 0.0182 | Nerves | 0.0301 |
| Prostate | 0.0499 | Prostate | 0.0068 |
| Sensory organs | 0.0126 | Sensory Organs | 0.0000 |
| | | Uterus_n | 0.0167 |

Electronic Northern for SEQ. ID NO.: 43

| | NORMAL | TUMOR | Ratios | |
|---|---|---|---|---|
| | % frequency | % frequency | N/T | T/N |
| Bladder | 0.0117 | 0.0102 | 1.1441 | 0.8741 |
| Breast | 0.0102 | 0.0226 | 0.4537 | 2.2042 |
| Small intestine | 0.0123 | 0.0165 | 0.7415 | 1.3487 |
| Ovary | 0.0030 | 0.0078 | 0.3838 | 2.6058 |
| Endocrine tissue | 0.0136 | 0.0150 | 0.9057 | 1.1042 |
| Gastrointestinal | 0.0153 | 0.0046 | 3.3134 | 0.3018 |
| Brain | 0.0074 | 0.0103 | 0.7200 | 1.3890 |
| Hematopoietic | 0.0053 | 0.0379 | 0.1412 | 7.0845 |
| Skin | 0.0000 | 0.0000 | undef | undef |
| Hepatic | 0.0143 | 0.0129 | 1.1029 | 0.9067 |
| Heart | 0.0074 | 0.0137 | 0.5397 | 1.8529 |
| Testicles | 0.0173 | 0.0000 | undef | 0.0000 |
| Lung | 0.0125 | 0.0164 | 0.7621 | 1.3122 |
| Stomach-esophagus | 0.0097 | 0.0153 | 0.6303 | 1.5866 |
| Muscle-skeleton | 0.0154 | 0.0060 | 2.5700 | 0.3891 |
| Kidney | 0.0109 | 0.0137 | 0.7930 | 1.2610 |
| Pancreas | 0.0083 | 0.0276 | 0.2991 | 3.3428 |
| Penis | 0.0150 | 0.0533 | 0.2808 | 3.5614 |
| Prostate | 0.0196 | 0.0149 | 1.3161 | 0.7598 |
| Uterus-endometrium | 0.0000 | 0.1055 | 0.0000 | undef |
| Uterus-myometrium | 0.0000 | 0.0136 | 0.0000 | undef |
| Uterus-general | 0.0153 | 0.0000 | undef | 0.0000 |
| Breast hyperplasia | 0.0032 | | | |
| Prostate hyperplasia | 0.0208 | | | |
| Seminal vesicle | 0.0178 | | | |
| Sensory organs | 0.0706 | | | |
| White blood cells | 0.0251 | | | |
| Cervix | 0.0106 | | | |

| | FETUS % frequency | STANDARDIZED/SUB-TRACTED LIBRARIES % frequency | |
|---|---|---|---|
| Development | 0.0139 | Breast | 0.0272 |
| Gastrointestinal | 0.0139 | Ovary_n | 0.0000 |
| Brain | 0.0125 | Ovary_t | 0.0557 |
| Hematopoietic | 0.0118 | Endocrine tissue | 0.0245 |
| Skin | 0.0000 | Fetal | 0.0402 |
| Hepatic | 0.0000 | Gastrointestinal | 0.0610 |
| Heart-blood vessels | 0.0000 | Hematopoietic | 0.0342 |
| Lung | 0.0217 | Skin-muscle | 0.0486 |
| Suprarenal gland | 0.0254 | Testicles | 0.0309 |
| Kidney | 0.0185 | Lung | 0.0328 |
| Placenta | 0.0303 | Nerves | 0.0100 |
| Prostate | 0.0000 | Prostate | 0.0274 |
| Sensory organs | 0.0000 | Sensory Organs | 0.0310 |
| | | Uterus_n | 0.0291 |

Electronic Northern for SEQ. ID NO.: 44

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0026 | 0.0019 | 1.3611 | 0.7347 |
| Small intestine | 0.0000 | 0.0000 | undef | undef |
| Ovary | 0.0030 | 0.0000 | undef | 0.0000 |
| Endocrine tissue | 0.0017 | 0.0000 | undef | 0.0000 |
| Gastrointestinal | 0.0019 | 0.0000 | undef | 0.0000 |
| Brain | 0.0007 | 0.0000 | undef | 0.0000 |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0117 | 0.0000 | undef |
| Lung | 0.0000 | 0.0020 | 0.0000 | undef |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0000 | Ovary_n | 0.0000 |
| Brain | 0.0000 | Ovary_t | 0.0000 |

-continued

| | | | |
|---|---|---|---|
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0082 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 45

| | NORMAL | TUMOR | Ratios | |
|---|---|---|---|---|
| | % frequency | % frequency | N/T | T/N |
| Bladder | 0.0039 | 0.0051 | 0.7627 | 1.3111 |
| Breast | 0.0013 | 0.0094 | 0.1361 | 7.3472 |
| Small intestine | 0.0000 | 0.0000 | undef | undef |
| Ovary | 0.0030 | 0.0026 | 1.1513 | 0.8686 |
| Endocrine tissue | 0.0017 | 0.0100 | 0.1698 | 5.8889 |
| Gastrointestinal | 0.0134 | 0.0093 | 1.4496 | 0.6898 |
| Brain | 0.0052 | 0.0062 | 0.8400 | 1.1905 |
| Hematopoietic | 0.0000 | 0.0000 | undef | undef |
| Skin | 0.0073 | 0.0000 | undef | 0.0000 |
| Hepatic | 0.0000 | 0.0000 | undef | undef |
| Heart | 0.0053 | 0.0412 | 0.1285 | 7.7824 |
| Testicles | 0.0058 | 0.0117 | 0.4920 | 2.0326 |
| Lung | 0.0052 | 0.0000 | undef | 0.0000 |
| Stomach-esophagus | 0.0000 | 0.0000 | undef | undef |
| Muscle-skeleton | 0.0069 | 0.0060 | 1.1422 | 0.8755 |
| Kidney | 0.0027 | 0.0068 | 0.3965 | 2.5219 |
| Pancreas | 0.0017 | 0.0221 | 0.0748 | 13.3713 |
| Penis | 0.0090 | 0.0000 | undef | 0.0000 |
| Prostate | 0.0087 | 0.0085 | 1.0236 | 0.9769 |
| Uterus-endometrium | 0.0000 | 0.1583 | 0.0000 | undef |
| Uterus-myometrium | 0.0152 | 0.0204 | 0.7482 | 1.3366 |
| Uterus-general | 0.0051 | 0.0000 | undef | 0.0000 |
| Breast hyperplasia | 0.0032 | | | |
| Prostate hyperplasia | 0.0059 | | | |
| Seminal vesicle | 0.0000 | | | |
| Sensory organs | 0.0000 | | | |
| White blood cells | 0.0035 | | | |
| Cervix | 0.0000 | | | |

| | FETUS % frequency | STANDARDIZED/SUBTRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0063 | Ovary_t | 0.0051 |
| Hematopoietic | 0.0000 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0036 | Hematopoietic | 0.0000 |
| Lung | 0.0072 | Skin-muscle | 0.0000 |
| Suprarenal gland | 0.0000 | Testicles | 0.0000 |
| Kidney | 0.0000 | Lung | 0.0000 |
| Placenta | 0.0182 | Nerves | 0.0040 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 46

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0061 | 0.0000 | undef | 0.0000 |
| Ovary | 0.0000 | 0.0026 | 0.0000 | undef |
| Endocrine tissue | 0.0000 | 0.0025 | 0.0000 | undef |
| Gastrointestinal | 0.0000 | 0.0000 | undef | undef |
| Brain | 0.0022 | 0.0010 | 2.1599 | 0.4630 |
| Hematopoietic | 0.0000 | 0.0000 | undef | undef |
| Skin | 0.0000 | 0.0000 | undef | undef |
| Hepatic | 0.0048 | 0.0000 | undef | 0.0000 |
| Heart | 0.0042 | 0.0000 | undef | 0.0000 |
| Testicles | 0.0000 | 0.0000 | undef | undef |
| Lung | 0.0000 | 0.0000 | undef | undef |
| Stomach-esophagus | 0.0097 | 0.0000 | undef | 0.0000 |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0032 | | | |
| Prostate hyperplasia | 0.0030 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUBTRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0107 | Hematopoietic | 0.0000 |
| Lung | 0.0036 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0249 | Prostate | 0.0000 |
| Sensory organs | 0.0000 | Sensory Organs | 0.0000 |
| | | Uterus_n | 0.0000 |

Electronic Northern for SEQ. ID NO.: 47

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0012 | 0.0000 | undef | 0.0000 |
| Small intestine | 0.0031 | 0.0000 | undef | 0.0000 |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0015 | 0.0010 | 1.4399 | 0.6945 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0017 | 0.0060 | 0.2856 | 3.5020 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0152 | 0.0000 | undef | 0.0000 |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0000 | | | |

-continued

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 48

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0015 | 0.0010 | 1.4399 | 0.6945 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0017 | 0.0060 | 0.2856 | 3.5020 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.2111 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 49

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0000 | undef | 0.0000 |
| Small intestine | 0.0000 | 0.0165 | 0.0000 | undef |
| Ovary | 0.0000 | 0.0000 | undef | undef |
| Endocrine tissue | 0.0017 | 0.0050 | 0.3396 | 2.9444 |
| Gastrointestinal | 0.0000 | 0.0000 | undef | undef |
| Brain | 0.0000 | 0.0010 | 0.0000 | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0000 | 0.0000 | undef | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0204 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0000 | Hematopoietic | 0.0000 |
| Lung | 0.0036 | Skin-muscle | 0.0065 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 50

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |

-continued

| | | | | |
|---|---|---|---|---|
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 51

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB- TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 52

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0030 | 0.0000 | undef | 0.0000 |
| Endocrine tissue | 0.0000 | 0.0125 | 0.0000 | undef |
| Gastrointestinal | 0.0000 | 0.0000 | undef | undef |
| Brain | 0.0044 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0000 | 0.0000 | undef | undef |
| Penis | 0.0000 | 0.0000 | undef | undef |
| Prostate | 0.0022 | 0.0021 | 1.0236 | 0.9769 |
| Uterus-endometrium | 0.0000 | 0.1583 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0106 | | | |

| | FETUS % frequency | STANDARDIZED/SUB- TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0006 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0040 |
| Prostate | 0.0000 | Prostate | 0.0068 |
| Sensory organs | 0.0000 | Sensory Organs | 0.0000 |
| | | Uterus_n | 0.0000 |

Electronic Northern for SEQ. ID NO.: 53

| | NORMAL | TUMOR | Ratios | |
|---|---|---|---|---|
| | % frequency | % frequency | N/T | T/N |
| Bladder | 0.0039 | 0.0051 | 0.7627 | 1.3111 |
| Breast | 0.0051 | 0.0000 | undef | 0.0000 |
| Small intestine | 0.0000 | 0.0000 | undef | undef |
| Ovary | 0.0000 | 0.0000 | undef | undef |
| Endocrine tissue | 0.0034 | 0.0025 | 1.3585 | 0.7361 |
| Gastrointestinal | 0.0019 | 0.0000 | undef | 0.0000 |
| Brain | 0.0015 | 0.0031 | 0.4800 | 2.0835 |
| Hematopoietic | 0.0067 | 0.0000 | undef | 0.0000 |
| Skin | 0.0441 | 0.0000 | undef | 0.0000 |
| Hepatic | 0.0048 | 0.0065 | 0.7353 | 1.3600 |
| Heart | 0.0064 | 0.0000 | undef | 0.0000 |
| Testicles | 0.0000 | 0.0000 | undef | undef |
| Lung | 0.0010 | 0.0020 | 0.5080 | 1.9684 |
| Stomach-esophagus | 0.0000 | 0.0000 | undef | undef |
| Muscle-skeleton | 0.0017 | 0.0060 | 0.2856 | 3.5020 |

-continued

| | | | |
|---|---|---|---|
| Kidney | 0.0027 | 0.0000 | undef | 0.0000 |
| Pancreas | 0.0000 | 0.0000 | undef | undef |
| Penis | 0.0000 | 0.0267 | 0.0000 | undef |
| Prostate | 0.0044 | 0.0000 | undef | 0.0000 |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0954 | 0.0000 | undef |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0026 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0101 |
| Hematopoietic | 0.0000 | Endocrine tissue | 0.0000 |
| Skin | 0.0000 | Fetal | 0.0017 |
| Hepatic | 0.0000 | Gastrointestinal | 0.0244 |
| Heart-blood vessels | 0.0000 | Hematopoietic | 0.0000 |
| Lung | 0.0000 | Skin-muscle | 0.0065 |
| Suprarenal gland | 0.0254 | Testicles | 0.0077 |
| Kidney | 0.0000 | Lung | 0.0082 |
| Placenta | 0.0061 | Nerves | 0.0010 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 54

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0026 | 0.0019 | 1.3611 | 0.7347 |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0019 | 0.0000 | undef | 0.0000 |
| Brain | 0.0000 | 0.0000 | undef | undef |
| Hematopoietic | 0.0013 | 0.0000 | undef | 0.0000 |
| Skin | 0.0000 | 0.0000 | undef | undef |
| Hepatic | 0.0000 | 0.0000 | undef | undef |
| Heart | 0.0021 | 0.0000 | undef | 0.0000 |
| Testicles | 0.0000 | 0.0000 | undef | undef |
| Lung | 0.0010 | 0.0020 | 0.5080 | 1.9684 |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0000 | 0.0000 | undef | undef |
| Penis | 0.0000 | 0.0000 | undef | undef |
| Prostate | 0.0022 | 0.0106 | 0.2047 | 4.8846 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0032 | | | |
| Prostate hyperplasia | 0.0059 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0122 |
| Heart-blood vessels | 0.0071 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0061 | Nerves | 0.0000 |
| Prostate | 0.0000 | Prostate | 0.0000 |
| Sensory organs | 0.0126 | Sensory Organs | 0.0000 |
| | | Uterus_n | 0.0000 |

Electronic Northern for SEQ. ID NO.: 55

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0019 | 0.6805 | 1.4694 |
| Small intestine | 0.0031 | 0.0000 | undef | 0.0000 |
| Ovary | 0.0060 | 0.0026 | 2.3025 | 0.4343 |
| Endocrine tissue | 0.0017 | 0.0050 | 0.3396 | 2.9444 |
| Gastrointestinal | 0.0022 | 0.0093 | 0.6213 | 1.6096 |
| Brain | 0.0027 | 0.0041 | 0.5400 | 1.8520 |
| Hematopoietic | 0.0000 | 0.0000 | undef | 0.0000 |
| Skin | 0.0048 | 0.0000 | undef | undef |
| Hepatic | 0.0000 | 0.0000 | undef | 0.0000 |
| Heart | 0.0000 | 0.0000 | undef | undef |
| Testicles | 0.0010 | 0.0117 | 0.0000 | undef |
| Lung | 0.0000 | 0.0020 | 0.5080 | 1.9684 |
| Stomach-esophagus | 0.0000 | 0.0077 | 0.0000 | undef |
| Muscle-skeleton | 0.0054 | 0.0000 | undef | undef |
| Kidney | 0.0000 | 0.0068 | 0.7930 | 1.2610 |
| Pancreas | 0.0000 | 0.0000 | undef | undef |
| Penis | 0.0007 | 0.0000 | undef | undef |
| Prostate | 0.0068 | 0.0000 | undef | 0.0000 |
| Uterus-endometrium | 0.0000 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0017 |
| Hepatic | 0.0000 | Gastrointestinal | 0.0000 |
| Heart-blood vessels | 0.0036 | Hematopoietic | 0.0000 |
| Lung | 0.0036 | Skin-muscle | 0.0032 |
| Suprarenal gland | 0.0000 | Testicles | 0.0000 |
| Kidney | 0.0062 | Lung | 0.0000 |
| Placenta | 0.0061 | Nerves | 0.0030 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 56

| | NORMAL | TUMOR | Ratios | |
|---|---|---|---|---|
| | % frequency | % frequency | N/T | T/N |
| Bladder | 0.0117 | 0.0128 | 0.9153 | 1.0926 |
| Breast | 0.0051 | 0.0132 | 0.3889 | 2.5715 |
| Small intestine | 0.0061 | 0.0000 | undef | 0.0000 |
| Ovary | 0.0000 | 0.0208 | 0.0000 | undef |
| Endocrine tissue | 0.0102 | 0.0125 | 0.8151 | 1.2268 |
| Gastrointestinal | 0.0134 | 0.0046 | 2.8992 | 0.3449 |
| Brain | 0.0103 | 0.0113 | 0.9163 | 1.0913 |
| Hematopoietic | 0.0027 | 0.0000 | undef | 0.0000 |
| Skin | 0.0037 | 0.0000 | undef | 0.0000 |
| Hepatic | 0.0000 | 0.0194 | 0.0000 | undef |
| Heart | 0.0085 | 0.0000 | undef | 0.0000 |

-continued

| | | | |
|---|---|---|---|
| Testicles | 0.0173 | 0.0234 | 0.7380 | 1.3551 |
| Lung | 0.0145 | 0.0123 | 1.1854 | 0.8436 |
| Stomach-esophagus | 0.0097 | 0.0077 | 1.2605 | 0.7933 |
| Muscle-skeleton | 0.0069 | 0.0000 | undef | 0.0000 |
| Kidney | 0.0190 | 0.0000 | undef | 0.0000 |
| Pancreas | 0.0050 | 0.0055 | 0.8974 | 1.1143 |
| Penis | 0.0090 | 0.0000 | undef | 0.0000 |
| Prostate | 0.0022 | 0.0085 | 0.2559 | 3.9077 |
| Uterus-endometrium | 0.0068 | 0.1055 | 0.0640 | 15.6211 |
| Uterus-myometrium | 0.0076 | 0.0068 | 1.1223 | 0.8911 |
| Uterus-general | 0.0000 | 0.0000 | undef | undef |
| Breast hyperplasia | 0.0096 | | | |
| Prostate hyperplasia | 0.0030 | | | |
| Seminal vesicle | 0.0178 | | | |
| Sensory organs | 0.0000 | | | |
| White blood cells | 0.0052 | | | |
| Cervix | 0.0000 | | | |

| | FETUS % frequency | STANDARDIZED/SUB-TRACTED LIBRARIES % frequency | | |
|---|---|---|---|---|
| Development | 0.0000 | Breast | 0.0000 |
| Gastrointestinal | 0.0028 | Ovary_n | 0.0000 |
| Brain | 0.0063 | Ovary_t | 0.0051 |
| Hematopoietic | 0.0000 | Endocrine tissue | 0.0000 |
| Skin | 0.0000 | Fetal | 0.0012 |
| Hepatic | 0.0260 | Gastrointestinal | 0.0366 |
| Heart-blood vessels | 0.0107 | Hematopoietic | 0.0000 |
| Lung | 0.0000 | Skin-muscle | 0.0000 |
| Suprarenal gland | 0.0000 | Testicles | 0.0000 |
| Kidney | 0.0062 | Lung | 0.0082 |
| Placenta | 0.0000 | Nerves | 0.0020 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 57

| | NORMAL % frequency | TUMOR % frequency | Ratios N/T | T/N |
|---|---|---|---|---|
| Bladder | 0.0078 | 0.0000 | undef | 0.0000 |
| Breast | 0.0038 | 0.0075 | 0.5104 | 1.9593 |
| Small intestine | 0.0031 | 0.0000 | undef | 0.0000 |
| Ovary | 0.0000 | 0.0078 | 0.0000 | undef |
| Endocrine tissue | 0.0000 | 0.0000 | undef | undef |
| Gastrointestinal | 0.0077 | 0.0185 | 0.4142 | 2.4145 |
| Brain | 0.0096 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0117 | 0.0000 | undef |
| Lung | 0.0010 | 0.0000 | undef | 0.0000 |
| Stomach-esophagus | 0.0000 | 0.0153 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0109 | 0.0085 | 1.2795 | 0.7815 |
| Uterus-endometrium | 0.0000 | 0.1583 | 0.0000 | undef |
| Uterus-myometrium | 0.0000 | 0.0000 | undef | undef |
| Uterus-general | 0.0000 | 0.1908 | 0.0000 | undef |
| Breast hyperplasia | 0.0032 | | | |
| Prostate hyperplasia | 0.0089 | | | |
| Seminal vesicle | 0.0000 | | | |
| Sensory organs | 0.0000 | | | |
| White blood cells | 0.0000 | | | |
| Cervix | 0.0106 | | | |

| | FETUS % frequency | STANDARDIZED/SUB-TRACTED LIBRARIES % frequency | |
|---|---|---|---|
| Development | 0.0000 | Breast | 0.0068 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0072 | Skin-muscle | 0.0000 |
| Suprarenal gland | 0.0000 | Testicles | 0.0000 |
| Kidney | 0.0124 | Lung | 0.0000 |
| Placenta | 0.0000 | Nerves | 0.0050 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 58

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0017 | 0.0000 | undef | 0.0000 |
| Gastrointestinal | 0.0019 | 0.0000 | undef | 0.0000 |
| Brain | 0.0007 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.0000 | undef | undef |
| Uterus-myometrium | 0.0000 | 0.1055 | 0.0000 | undef |
| Uterus-general | 0.0000 | 0.0000 | undef | undef |
| Breast hyperplasia | 0.0000 | 0.0000 | undef | undef |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 59

| | NORMAL % frequency | TUMOR % frequency | Ratios N/T | T/N |
|---|---|---|---|---|
| Bladder | 0.0039 | 0.0026 | 1.5254 | 0.6555 |
| Breast | 0.0281 | 0.0226 | 1.2476 | 0.8015 |
| Small intestine | 0.0307 | 0.0000 | undef | 0.0000 |
| Ovary | 0.0000 | 0.0026 | 0.0000 | undef |
| Endocrine tissue | 0.0085 | 0.0000 | undef | 0.0000 |
| Gastrointestinal | 0.0153 | 0.0324 | 0.4733 | 2.1127 |
| Brain | 0.0044 | 0.0072 | 0.6171 | 1.6205 |

-continued

| | | | |
|---|---|---|---|
| Hematopoietic | 0.0053 | 0.0000 | undef | 0.0000 |
| Skin | 0.0257 | 0.0000 | undef | 0.0000 |
| Hepatic | 0.0048 | 0.0065 | 0.7353 | 1.3600 |
| Heart | 0.0032 | 0.0000 | undef | 0.0000 |
| Testicles | 0.0000 | 0.0000 | undef | undef |
| Lung | 0.0000 | 0.0061 | 0.0000 | undef |
| Stomach-esophagus | 0.0000 | 0.0153 | 0.0000 | undef |
| Muscle-skeleton | 0.0154 | 0.0180 | 0.8567 | 1.1673 |
| Kidney | 0.0217 | 0.0068 | 3.1722 | 0.3152 |
| Pancreas | 0.0000 | 0.0166 | 0.0000 | undef |
| Penis | 0.0030 | 0.0000 | undef | 0.0000 |
| Prostate | 0.0000 | 0.0021 | 0.0000 | undef |
| Uterus-endometrium | 0.0135 | 0.1055 | 0.1280 | 7.8106 |
| Uterus-myometrium | 0.0000 | 0.0000 | undef | undef |
| Uterus-general | 0.0000 | 0.0000 | undef | undef |
| Breast hyperplasia | 0.0128 | | | |
| Prostate hyperplasia | 0.0000 | | | |
| Seminal vesicle | 0.0000 | | | |
| Sensory organs | 0.0235 | | | |
| White blood cells | 0.0000 | | | |
| Cervix | 0.0106 | | | |

| | FETUS % frequency | STANDARDIZED/SUB-TRACTED LIBRARIES % frequency | |
|---|---|---|---|
| Development | 0.0139 | Breast | 0.0476 |
| Gastrointestinal | 0.0139 | Ovary_n | 0.0000 |
| Brain | 0.0000 | Ovary_t | 0.0101 |
| Hematopoietic | 0.0000 | Endocrine tissue | 0.0000 |
| Skin | 0.0000 | Fetal | 0.0151 |
| Hepatic | 0.0000 | Gastrointestinal | 0.0000 |
| Heart-blood vessels | 0.0000 | Hematopoietic | 0.0057 |
| Lung | 0.0181 | Skin-muscle | 0.0000 |
| Suprarenal gland | 0.0254 | Testicles | 0.0000 |
| Kidney | 0.0000 | Lung | 0.0082 |
| Placenta | 0.0303 | Nerves | 0.0050 |
| Prostate | 0.0000 | Prostate | 0.0137 |
| Sensory organs | 0.0000 | Sensory Organs | 0.0000 |
| | | Uterus_n | 0.0208 |

Electronic Northern for SEQ. ID NO.: 60

| | NORMAL % frequency | TUMOR % frequency | Ratios N/T | Ratios T/N |
|---|---|---|---|---|
| Bladder | 0.0156 | 0.0102 | 1.5254 | 0.6555 |
| Breast | 0.0115 | 0.0207 | 0.5568 | 1.7960 |
| Small intestine | 0.0215 | 0.0165 | 1.2976 | 0.7707 |
| Ovary | 0.0240 | 0.0260 | 0.9210 | 1.0858 |
| Endocrine tissue | 0.0119 | 0.0176 | 0.6792 | 1.4722 |
| Gastrointestinal | 0.0172 | 0.0139 | 1.2425 | 0.8048 |
| Brain | 0.0170 | 0.0246 | 0.6900 | 1.4494 |
| Hematopoietic | 0.0040 | 0.0000 | undef | 0.0000 |
| Skin | 0.0184 | 0.0000 | undef | 0.0000 |
| Hepatic | 0.0238 | 0.0194 | 1.2255 | 0.8160 |
| Heart | 0.0180 | 0.0275 | 0.6553 | 1.5260 |
| Testicles | 0.0058 | 0.0117 | 0.4920 | 2.0326 |
| Lung | 0.0156 | 0.0164 | 0.9526 | 1.0498 |
| Stomach-esophagus | 0.0193 | 0.0000 | undef | 0.0000 |
| Muscle-skeleton | 0.0103 | 0.0060 | 1.7133 | 0.5837 |
| Kidney | 0.0081 | 0.0411 | 0.1983 | 5.0439 |
| Pancreas | 0.0116 | 0.0055 | 2.0940 | 0.4775 |
| Penis | 0.0150 | 0.0267 | 0.5616 | 1.7807 |
| Prostate | 0.0131 | 0.0043 | 3.0709 | 0.3256 |
| Uterus-endometrium | 0.0135 | 0.1055 | 0.1280 | 7.8106 |
| Uterus-myometrium | 0.0000 | 0.0068 | 0.0000 | undef |
| Uterus-general | 0.0153 | 0.0000 | undef | 0.0000 |
| Breast hyperplasia | 0.0096 | | | |
| Prostate hyperplasia | 0.0059 | | | |
| Seminal vesicle | 0.0000 | | | |
| Sensory organs | 0.0118 | | | |
| White blood cells | 0.0061 | | | |
| Cervix | 0.0426 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0139 | Ovary_n | 0.0000 |
| Brain | 0.0125 | Ovary_t | 0.0000 |
| Hematopoietic | 0.0157 | Endocrine tissue | 0.0245 |
| Skin | 0.0000 | Fetal | 0.0151 |
| Hepatic | 0.0260 | Gastrointestinal | 0.0122 |
| Heart-blood vessels | 0.0213 | Hematopoietic | 0.0000 |
| Lung | 0.0036 | Skin-muscle | 0.0194 |
| Suprarenal gland | 0.0000 | Testicles | 0.0000 |
| Kidney | 0.0062 | Lung | 0.0246 |
| Placenta | 0.0061 | Nerves | 0.0211 |
| Prostate | 0.0000 | Prostate | 0.0274 |
| Sensory organs | 0.0126 | Sensory Organs | 0.0000 |
| | | Uterus_n | 0.0125 |

Electronic Northern for SEQ. ID NO.: 61

| | NORMAL % frequency | TUMOR % frequency | Ratios N/T | Ratios T/N |
|---|---|---|---|---|
| Bladder | 0.0000 | 0.0128 | 0.0000 | undef |
| Breast | 0.0000 | 0.0056 | 0.0000 | undef |
| Small intestine | 0.0061 | 0.0000 | undef | 0.0000 |
| Ovary | 0.0030 | 0.0000 | undef | 0.0000 |
| Endocrine tissue | 0.0119 | 0.0075 | 1.5849 | 0.6309 |
| Gastrointestinal | 0.0057 | 0.0000 | undef | 0.0000 |
| Brain | 0.0059 | 0.0072 | 0.8228 | 1.2153 |
| Hematopoietic | 0.0067 | 0.0000 | undef | 0.0000 |
| Skin | 0.0037 | 0.0000 | undef | 0.0000 |
| Hepatic | 0.0048 | 0.0129 | 0.3676 | 2.7200 |
| Heart | 0.0053 | 0.0000 | undef | 0.0000 |
| Testicles | 0.0058 | 0.0000 | undef | 0.0000 |
| Lung | 0.0031 | 0.0020 | 1.5241 | 0.6561 |
| Stomach-esophagus | 0.0193 | 0.0000 | undef | 0.0000 |
| Muscle-skeleton | 0.0017 | 0.0120 | 0.1428 | 7.0040 |
| Kidney | 0.0136 | 0.0000 | undef | 0.0000 |
| Pancreas | 0.0033 | 0.0276 | 0.1197 | 8.3571 |
| Penis | 0.0030 | 0.0000 | undef | 0.0000 |
| Prostate | 0.0153 | 0.0170 | 0.8957 | 1.1165 |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0032 | | | |
| Prostate hyperplasia | 0.0030 | | | |
| Seminal vesicle | 0.0000 | | | |
| Sensory organs | 0.0000 | | | |
| White blood cells | 0.0026 | | | |
| Cervix | 0.0106 | | | |

| | FETUS % frequency | STANDARDIZED/SUB-TRACTED LIBRARIES % frequency | |
|---|---|---|---|
| Development | 0.0000 | Breast | 0.0136 |
| Gastrointestinal | 0.0083 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0058 |
| Hepatic | 0.0000 | Gastrointestinal | 0.0122 |
| Heart-blood vessels | 0.0036 | Hematopoietic | 0.0057 |
| Lung | 0.0000 | Skin-muscle | 0.0000 |
| Suprarenal gland | 0.0000 | Testicles | 0.0154 |
| Kidney | 0.0124 | Lung | 0.0000 |
| Placenta | 0.0061 | Nerves | 0.0030 |
| Prostate | 0.0249 | Prostate | 0.0000 |
| Sensory organs | 0.0000 | Sensory Organs | 0.0000 |
| | | Uterus_n | 0.0000 |

-continued

Electronic Northern for SEQ. ID NO.: 62

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0017 | 0.0000 | undef | 0.0000 |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.0000 | undef | undef |
| Uterus-myometrium | 0.0000 | 0.1055 | 0.0000 | undef |
| Uterus-general | 0.0000 | 0.0000 | undef | undef |
| Breast hyperplasia | 0.0000 | 0.0000 | undef | undef |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|  | FETUS | STANDARDIZED/SUB-TRACTED LIBRARIES | |
|---|---|---|---|
|  | % frequency | | % frequency |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 63

|  | NORMAL | TUMOR | Ratios | |
|---|---|---|---|---|
|  | % frequency | % frequency | N/T | T/N |
| Bladder | 0.0078 | 0.0051 | 1.5254 | 0.6555 |
| Breast | 0.0038 | 0.0094 | 0.4083 | 2.4491 |
| Small intestine | 0.0031 | 0.0331 | 0.0927 | 10.7893 |
| Ovary | 0.0150 | 0.0208 | 0.7195 | 1.3898 |
| Endocrine tissue | 0.0136 | 0.0100 | 1.3585 | 0.7361 |
| Gastrointestinal | 0.0230 | 0.0046 | 4.9700 | 0.2012 |
| Brain | 0.0096 | 0.0082 | 1.1699 | 0.8547 |
| Hematopoietic | 0.0094 | 0.0000 | undef | 0.0000 |
| Skin | 0.0110 | 0.0000 | undef | 0.0000 |
| Hepatic | 0.0000 | 0.0065 | 0.0000 | undef |
| Heart | 0.0053 | 0.0000 | undef | 0.0000 |
| Testicles | 0.0173 | 0.0000 | undef | 0.0000 |
| Lung | 0.0052 | 0.0041 | 1.2701 | 0.7873 |
| Stomach-esophagus | 0.0387 | 0.0077 | 5.0421 | 0.1983 |
| Muscle-skeleton | 0.0051 | 0.0120 | 0.4283 | 2.3347 |
| Kidney | 0.0081 | 0.0274 | 0.2974 | 2.3626 |
| Pancreas | 0.0083 | 0.0110 | 0.7479 | 1.3371 |
| Penis | 0.0150 | 0.0267 | 0.5616 | 1.7807 |
| Prostate | 0.0044 | 0.0043 | 1.0236 | 0.9769 |
| Uterus-endometrium | 0.0068 | 0.2111 | 0.0320 | 31.2422 |
| Uterus-myometrium | 0.0076 | 0.0068 | 1.1223 | 0.8911 |
| Uterus-general | 0.0051 | 0.0000 | undef | 0.0000 |
| Breast hyperplasia | 0.0256 | | | |
| Prostate hyperplasia | 0.0089 | | | |
| Seminal vesicle | 0.0000 | | | |
| Sensory organs | 0.0235 | | | |
| White blood cells | 0.0061 | | | |
| Cervix | 0.0000 | | | |

|  | FETUS | STANDARDIZED/SUB-TRACTED LIBRARIES | |
|---|---|---|---|
|  | % frequency | | % frequency |
| Development | 0.0278 | Breast | 0.0204 |
| Gastrointestinal | 0.0056 | Ovary_n | 0.1595 |
| Brain | 0.0000 | Ovary_t | 0.0000 |
| Hematopoietic | 0.0236 | Endocrine tissue | 0.0000 |
| Skin | 0.0000 | Fetal | 0.0047 |
| Hepatic | 0.0000 | Gastrointestinal | 0.0000 |
| Heart-blood vessels | 0.0356 | Hematopoietic | 0.0228 |
| Lung | 0.0289 | Skin-muscle | 0.0097 |
| Suprarenal gland | 0.0000 | Testicles | 0.0231 |
| Kidney | 0.0124 | Lung | 0.0000 |
| Placenta | 0.0000 | Nerves | 0.0100 |
| Prostate | 0.0000 | Prostate | 0.0000 |
| Sensory organs | 0.0628 | Sensory Organs | 0.0000 |
|  |  | Uterus_n | 0.0083 |

Electronic Northern for SEQ. ID NO.: 64

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|  | FETUS | STANDARDIZED/SUB-TRACTED LIBRARIES | |
|---|---|---|---|
|  | % frequency | | % frequency |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |

Electronic Northern for SEQ. ID NO.: 65

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0007 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0244 | 0.0137 | 1.7843 | 0.5604 |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0041 |
| Hepatic | 0.0000 | Gastrointestinal | 0.0000 |
| Heart-blood vessels | 0.0000 | Hematopoietic | 0.0057 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 66

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 67

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0038 | 0.0000 | undef |
| Small intestine | 0.0031 | 0.0000 | undef | 0.0000 |
| Ovary | 0.0000 | 0.0052 | 0.0000 | undef |
| Endocrine tissue | 0.0034 | 0.0000 | undef | 0.0000 |
| Gastrointestinal | 0.0000 | 0.0000 | undef | undef |
| Brain | 0.0022 | 0.0010 | 2.1599 | 0.4630 |
| Hematopoietic | 0.0013 | 0.0000 | undef | 0.0000 |
| Skin | 0.0000 | 0.0000 | undef | undef |
| Hepatic | 0.0000 | 0.0000 | undef | undef |
| Heart | 0.0032 | 0.0000 | undef | 0.0000 |
| Testicles | 0.0058 | 0.0000 | undef | 0.0000 |
| Lung | 0.0010 | 0.0020 | 0.5080 | 1.9684 |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0030 | 0.0000 | undef | 0.0000 |
| Uterus-endometrium | 0.0044 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0047 |
| Hepatic | 0.0000 | Gastrointestinal | 0.0000 |
| Heart-blood vessels | 0.0000 | Hematopoietic | 0.0000 |

-continued

| | | | | |
|---|---|---|---|---|
| Lung | 0.0000 | Skin-muscle | | 0.0097 |
| Suprarenal gland | 0.0000 | Testicles | | 0.0000 |
| Kidney | 0.0000 | Lung | | 0.0000 |
| Placenta | 0.0000 | Nerves | | 0.0000 |
| Prostate | 0.0000 | Prostate | | 0.0068 |
| Sensory organs | 0.0000 | Sensory Organs | | 0.0000 |
| | | Uterus_n | | 0.0125 |

Electronic Northern for SEQ. ID NO.: 68

| | NORMAL | TUMOR | Ratios | |
|---|---|---|---|---|
| | % frequency | % frequency | N/T | T/N |
| Bladder | 0.0078 | 0.0128 | 0.6102 | 1.6389 |
| Breast | 0.0038 | 0.0188 | 0.2042 | 4.8982 |
| Small intestine | 0.0153 | 0.0331 | 0.4634 | 2.1579 |
| Ovary | 0.0120 | 0.0208 | 0.5756 | 1.7372 |
| Endocrine tissue | 0.0136 | 0.0125 | 1.0868 | 0.9201 |
| Gastrointestinal | 0.0077 | 0.0000 | undef | 0.0000 |
| Brain | 0.0052 | 0.0041 | 1.2599 | 0.7937 |
| Hematopoietic | 0.0027 | 0.0000 | undef | 0.0000 |
| Skin | 0.0000 | 0.0847 | 0.0000 | undef |
| Hepatic | 0.0095 | 0.0194 | 0.4902 | 2.0400 |
| Heart | 0.0307 | 0.0275 | 1.1179 | 0.8945 |
| Testicles | 0.0000 | 0.0351 | 0.0000 | undef |
| Lung | 0.0042 | 0.0286 | 0.1452 | 6.8893 |
| Stomach-esophagus | 0.0000 | 0.0000 | undef | undef |
| Muscle-skeleton | 0.0051 | 0.0120 | 0.4283 | 2.3347 |
| Kidney | 0.0054 | 0.0137 | 0.3965 | 2.5219 |
| Pancreas | 0.0116 | 0.0110 | 1.0470 | 0.9551 |
| Penis | 0.0030 | 0.0000 | undef | 0.0000 |
| Prostate | 0.0044 | 0.0106 | 0.4095 | 2.4423 |
| Uterus-endometrium | 0.0135 | 0.1583 | 0.0854 | 11.7158 |
| Uterus-myometrium | 0.0076 | 0.0204 | 0.3741 | 2.6732 |
| Uterus-general | 0.0102 | 0.1908 | 0.0534 | 18.7357 |
| Breast hyperplasia | 0.0160 | | | |
| Prostate hyperplasia | 0.0119 | | | |
| Seminal vesicle | 0.0089 | | | |
| Sensory organs | 0.0000 | | | |
| White blood cells | 0.0130 | | | |
| Cervix | 0.0000 | | | |

| | FETUS | STANDARDIZED/SUB-TRACTED LIBRARIES | |
|---|---|---|---|
| | % frequency | % frequency | |
| Development | 0.0557 | Breast | 0.0000 |
| Gastrointestinal | 0.0194 | Ovary_n | 0.0000 |
| Brain | 0.0000 | Ovary_t | 0.0000 |
| Hematopoietic | 0.0079 | Endocrine tissue | 0.0245 |
| Skin | 0.0000 | Fetal | 0.0105 |
| Hepatic | 0.0000 | Gastrointestinal | 0.0122 |
| Heart-blood vessels | 0.0142 | Hematopoietic | 0.0000 |
| Lung | 0.0108 | Skin-muscle | 0.0421 |
| Suprarenal gland | 0.0254 | Testicles | 0.0077 |
| Kidney | 0.0000 | Lung | 0.0082 |
| Placenta | 0.0061 | Nerves | 0.0030 |
| Prostate | 0.0748 | Prostate | 0.0137 |
| Sensory organs | 0.0126 | Sensory Organs | 0.0000 |
| | | Uterus_n | 0.0083 |

Electronic Northern for SEQ. ID NO.: 69

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0000 | | | |

| | FETUS | STANDARDIZED/SUB-TRACTED LIBRARIES | |
|---|---|---|---|
| | % frequency | % frequency | |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0010 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 70

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS | STANDARDIZED/SUB-TRACTED LIBRARIES | |
|---|---|---|---|
| | % frequency | % frequency | |
| Development | 0.0000 | Breast | 0.0000 |
| Gastrointestinal | 0.0000 | Ovary_n | 0.0000 |
| Brain | 0.0000 | Ovary_t | 0.0000 |

| | | | | |
|---|---|---|---|---|
| Hematopoietic | 0.0000 | Endocrine tissue | 0.0000 | |
| Skin | 0.0000 | Fetal | 0.0000 | |
| Hepatic | 0.0000 | Gastrointestinal | 0.0000 | |
| Heart-blood vessels | 0.0000 | Hematopoietic | 0.0000 | |
| Lung | 0.0000 | Skin-muscle | 0.0000 | |
| Suprarenal gland | 0.0000 | Testicles | 0.0000 | |
| Kidney | 0.0000 | Lung | 0.0000 | |
| Placenta | 0.0000 | Nerves | 0.0000 | |
| Prostate | 0.0000 | Prostate | 0.0000 | |
| Sensory organs | 0.0000 | Sensory Organs | 0.0000 | |
| | | Uterus_n | 0.0000 | |

Electronic Northern for SEQ. ID NO.: 71

| | NORMAL | TUMOR | Ratios | |
|---|---|---|---|---|
| | % frequency | % frequency | N/T | T/N |
| Bladder | 0.0000 | 0.0230 | 0.0000 | undef |
| Breast | 0.0051 | 0.0056 | 0.9074 | 1.1021 |
| Small intestine | 0.0215 | 0.0000 | undef | 0.0000 |
| Ovary | 0.0060 | 0.0182 | 0.3289 | 3.0402 |
| Endocrine tissue | 0.0068 | 0.0000 | undef | 0.0000 |
| Gastrointestinal | 0.0728 | 0.0185 | 3.9346 | 0.2542 |
| Brain | 0.0000 | 0.0010 | 0.0000 | undef |
| Hematopoietic | 0.0027 | 0.0000 | undef | 0.0000 |
| Skin | 0.0000 | 0.0000 | undef | undef |
| Hepatic | 0.0048 | 0.0259 | 0.1838 | 5.4400 |
| Heart | 0.0011 | 0.0000 | undef | 0.0000 |
| Testicles | 0.0173 | 0.0000 | undef | 0.0000 |
| Lung | 0.0114 | 0.0061 | 1.8628 | 0.5368 |
| Stomach-esophagus | 0.0387 | 0.0000 | undef | 0.0000 |
| Muscle-skeleton | 0.0017 | 0.0000 | undef | 0.0000 |
| Kidney | 0.0081 | 0.0000 | undef | 0.0000 |
| Pancreas | 0.0033 | 0.0068 | 1.1896 | 0.8406 |
| Penis | 0.0000 | 0.0055 | 0.5983 | 1.6714 |
| Prostate | 0.0065 | 0.0000 | undef | undef |
| Uterus-endometrium | 0.0000 | 0.0106 | 0.6142 | 1.6282 |
| Uterus-myometrium | 0.0000 | 0.1055 | 0.0000 | undef |
| Uterus-general | 0.0000 | 0.0000 | undef | undef |
| Breast hyperplasia | 0.0000 | 0.0000 | undef | undef |
| Prostate hyperplasia | 0.0030 | | | |
| Seminal vesicle | 0.0089 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0136 |
| Gastrointestinal | 0.0083 | Ovary_n | 0.0000 |
| Brain | 0.0000 | Ovary_t | 0.0608 |
| Hematopoietic | 0.0000 | Endocrine tissue | 0.0000 |
| Skin | 0.0000 | Fetal | 0.0047 |
| Hepatic | 0.0000 | Gastrointestinal | 0.0000 |
| Heart-blood vessels | 0.0000 | Hematopoietic | 0.0000 |
| Lung | 0.0072 | Skin-muscle | 0.0000 |
| Suprarenal gland | 0.0000 | Testicles | 0.0000 |
| Kidney | 0.0062 | Lung | 0.0164 |
| Placenta | 0.0061 | Nerves | 0.0000 |
| Prostate | 0.0000 | Prostate | 0.0068 |
| Sensory organs | 0.0000 | Sensory Organs | 0.0000 |
| | | Uterus_n | 0.0000 |

Electronic Northern for SEQ. ID NO.: 72

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0026 | 0.0000 | undef |
| Endocrine tissue | 0.0000 | 0.0050 | 0.0000 | undef |
| Gastrointestinal | 0.0019 | 0.0000 | undef | 0.0000 |
| Brain | 0.0007 | 0.0000 | undef | 0.0000 |
| Hematopoietic | 0.0013 | 0.0000 | undef | 0.0000 |
| Skin | 0.0037 | 0.0000 | undef | 0.0000 |
| Hepatic | 0.0000 | 0.0000 | undef | undef |
| Heart | 0.0021 | 0.0000 | undef | 0.0000 |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0034 | 0.0000 | undef | 0.0000 |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0000 | 0.0000 | undef | undef |
| Uterus-endometrium | 0.0068 | 0.2111 | 0.0320 | 31.2422 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0068 |
| Gastrointestinal | 0.0000 | Ovary_n | 0.0000 |
| Brain | 0.0063 | Ovary_t | 0.0051 |
| Hematopoietic | 0.0000 | Endocrine tissue | 0.0000 |
| Skin | 0.0000 | Fetal | 0.0047 |
| Hepatic | 0.0000 | Gastrointestinal | 0.0366 |
| Heart-blood vessels | 0.0036 | Hematopoietic | 0.0000 |
| Lung | 0.0000 | Skin-muscle | 0.0000 |
| Suprarenal gland | 0.0000 | Testicles | 0.0154 |
| Kidney | 0.0309 | Lung | 0.0000 |
| Placenta | 0.0000 | Nerves | 0.0040 |
| Prostate | 0.0000 | Prostate | 0.0000 |
| Sensory organs | 0.0000 | Sensory Organs | 0.0000 |
| | | Uterus_n | 0.0125 |

Electronic Northern for SEQ. ID NO.: 73

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0019 | 0.6805 | 1.4694 |
| Small intestine | 0.0000 | 0.0165 | 0.0000 | undef |
| Ovary | 0.0000 | 0.0078 | 0.0000 | undef |
| Endocrine tissue | 0.0000 | 0.0000 | undef | undef |
| Gastrointestinal | 0.0019 | 0.0000 | undef | 0.0000 |
| Brain | 0.0007 | 0.0021 | 0.3600 | 2.7779 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0021 | 0.0000 | undef | 0.0000 |
| Testicles | 0.0000 | 0.0234 | 0.0000 | undef |
| Lung | 0.0021 | 0.0061 | 0.3387 | 2.9526 |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0043 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0017 | | | |
| Cervix | 0.0000 | | | |

|  | FETUS % frequency | STANDARDIZED/SUB-TRACTED LIBRARIES % frequency |  |
|---|---|---|---|
| Development | 0.0000 | Breast | 0.0136 |
| Gastrointestinal | 0.0000 | Ovary_n | 0.0000 |
| Brain | 0.0063 | Ovary_t | 0.0000 |
| Hematopoietic | 0.0039 | Endocrine tissue | 0.0000 |
| Skin | 0.0000 | Fetal | 0.0029 |
| Hepatic | 0.0000 | Gastrointestinal | 0.0000 |
| Heart-blood vessels | 0.0071 | Hematopoietic | 0.0114 |
| Lung | 0.0072 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0010 |
| Prostate | 0.0000 | Prostate | 0.0137 |
| Sensory organs | 0.0000 | Sensory Organs | 0.0000 |
|  |  | Uterus_n | 0.0000 |

Electronic Northern for SEQ. ID NO.: 74

|  | NORMAL % frequency | TUMOR % frequency | Ratios N/T | Ratios T/N |
|---|---|---|---|---|
| Bladder | 0.0078 | 0.0051 | 1.5254 | 0.6555 |
| Breast | 0.0051 | 0.0075 | 0.6805 | 1.4694 |
| Small intestine | 0.0031 | 0.0000 | undef | 0.0000 |
| Ovary | 0.0090 | 0.0000 | undef | 0.0000 |
| Endocrine tissue | 0.0119 | 0.0125 | 0.9509 | 1.0516 |
| Gastrointestinal | 0.0057 | 0.0046 | 1.2425 | 0.8048 |
| Brain | 0.0059 | 0.0051 | 1.1519 | 0.8681 |
| Hematopoietic | 0.0187 | 0.0379 | 0.4940 | 2.0241 |
| Skin | 0.0000 | 0.0000 | undef | undef |
| Hepatic | 0.0000 | 0.0000 | undef | undef |
| Heart | 0.0085 | 0.0000 | undef | 0.0000 |
| Testicles | 0.0000 | 0.0117 | 0.0000 | undef |
| Lung | 0.0073 | 0.0041 | 1.7781 | 0.5624 |
| Stomach-esophagus | 0.0000 | 0.0077 | 0.0000 | undef |
| Muscle-skeleton | 0.0000 | 0.0120 | 0.0000 | undef |
| Kidney | 0.0000 | 0.0068 | 0.0000 | undef |
| Pancreas | 0.0033 | 0.0000 | undef | 0.0000 |
| Penis | 0.0030 | 0.0000 | undef | 0.0000 |
| Prostate | 0.0065 | 0.0043 | 1.5354 | 0.6513 |
| Uterus-endometrium | 0.0000 | 0.1583 | 0.0000 | undef |
| Uterus-myometrium | 0.0229 | 0.0000 | undef | 0.0000 |
| Uterus-general | 0.0204 | 0.0000 | undef | 0.0000 |
| Breast hyperplasia | 0.0000 |  |  |  |
| Prostate hyperplasia | 0.0000 |  |  |  |
| Seminal vesicle | 0.0089 |  |  |  |
| Sensory organs | 0.0000 |  |  |  |
| White blood cells | 0.0035 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0068 |
| Gastrointestinal | 0.0028 | Ovary_n | 0.0000 |
| Brain | 0.0000 | Ovary_t | 0.0000 |
| Hematopoietic | 0.0079 | Endocrine tissue | 0.0000 |
| Skin | 0.2513 | Fetal | 0.0023 |
| Hepatic | 0.0000 | Gastrointestinal | 0.0000 |
| Heart-blood vessels | 0.0000 | Hematopoietic | 0.0000 |
| Lung | 0.0072 | Skin-muscle | 0.0065 |
| Suprarenal gland | 0.0000 | Testicles | 0.0154 |
| Kidney | 0.0124 | Lung | 0.0246 |
| Placenta | 0.0061 | Nerves | 0.0010 |
| Prostate | 0.0000 | Prostate | 0.0000 |
| Sensory organs | 0.0000 | Sensory Organs | 0.0077 |
|  |  | Uterus_n | 0.0083 |

Electronic Northern for SEQ. ID NO.: 75

|  | NORMAL % frequency | TUMOR % frequency | Ratios N/T | Ratios T/N |
|---|---|---|---|---|
| Bladder | 0.0039 | 0.0051 | 0.7627 | 1.3111 |
| Breast | 0.0026 | 0.0038 | 0.6805 | 1.4694 |
| Small intestine | 0.0000 | 0.0000 | undef | undef |
| Ovary | 0.0090 | 0.0078 | 1.1513 | 0.8686 |
| Endocrine tissue | 0.0051 | 0.0075 | 0.6792 | 1.4722 |
| Gastrointestinal | 0.0019 | 0.0231 | 0.0828 | 12.0723 |
| Brain | 0.0089 | 0.0031 | 2.8798 | 0.3472 |
| Hematopoietic | 0.0027 | 0.0000 | undef | 0.0000 |
| Skin | 0.0000 | 0.0000 | undef | undef |
| Hepatic | 0.0048 | 0.0000 | undef | 0.0000 |
| Heart | 0.0032 | 0.0000 | undef | 0.0000 |
| Testicles | 0.0058 | 0.0000 | undef | 0.0000 |
| Lung | 0.0031 | 0.0061 | 0.5080 | 1.9684 |
| Stomach-esophagus | 0.0000 | 0.0077 | 0.0000 | undef |
| Muscle-skeleton | 0.0034 | 0.0060 | 0.5711 | 1.7510 |
| Kidney | 0.0054 | 0.0000 | undef | 0.0000 |
| Pancreas | 0.0000 | 0.0055 | 0.0000 | undef |
| Penis | 0.0090 | 0.0000 | undef | 0.0000 |
| Prostate | 0.0022 | 0.0043 | 0.5118 | 1.9538 |
| Uterus-endometrium | 0.0000 | 0.1055 | 0.0000 | undef |
| Uterus-myometrium | 0.0000 | 0.0068 | 0.0000 | undef |
| Uterus-general | 0.0051 | 0.0000 | undef | 0.0000 |
| Breast hyperplasia | 0.0032 |  |  |  |
| Prostate hyperplasia | 0.0030 |  |  |  |
| Seminal vesicle | 0.0000 |  |  |  |
| Sensory organs | 0.0000 |  |  |  |
| White blood cells | 0.0017 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0151 |
| Hepatic | 0.0000 | Gastrointestinal | 0.0000 |
| Heart-blood vessels | 0.0036 | Hematopoietic | 0.0114 |
| Lung | 0.0000 | Skin-muscle | 0.0130 |
| Suprarenal gland | 0.0254 | Testicles | 0.0000 |
| Kidney | 0.0000 | Lung | 0.0082 |
| Placenta | 0.0000 | Nerves | 0.0060 |
| Prostate | 0.0000 | Prostate | 0.0137 |
| Sensory organs | 0.0000 | Sensory Organs | 0.0000 |
|  |  | Uterus_n | 0.0208 |

Electronic Northern for SEQ. ID NO.: 76

|  | NORMAL % frequency | TUMOR % frequency | Ratios N/T | Ratios T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |

-continued

| | | | |
|---|---|---|---|
| Uterus-endometrium | 0.0000 | 0.2111 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 77

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 78

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0213 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 79

| | NORMAL % frequency | TUMOR % frequency | Ratios N/T | T/N |
|---|---|---|---|---|
| Bladder | 0.0000 | 0.0000 | undef | undef |
| Breast | 0.0013 | 0.0000 | undef | 0.0000 |
| Small intestine | 0.0000 | 0.0000 | undef | undef |
| Ovary | 0.0030 | 0.0000 | undef | 0.0000 |
| Endocrine tissue | 0.0017 | 0.0050 | 0.3396 | 2.9444 |
| Gastrointestinal | 0.0019 | 0.0000 | undef | 0.0000 |
| Brain | 0.0007 | 0.0031 | 0.2400 | 4.1669 |
| Hematopoietic | 0.0000 | 0.0000 | undef | undef |
| Skin | 0.0000 | 0.0000 | undef | undef |
| Hepatic | 0.0048 | 0.0129 | 0.3676 | 2.7200 |
| Heart | 0.0000 | 0.0000 | undef | undef |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0034 | 0.0000 | undef | 0.0000 |

-continued

| | | | |
|---|---|---|---|
| Kidney | 0.0000 | 0.0000 | undef | undef |
| Pancreas | 0.0000 | 0.0055 | 0.0000 | undef |
| Penis | 0.0000 | 0.0000 | undef | undef |
| Prostate | 0.0044 | 0.0021 | 2.0473 | 0.4885 |
| Uterus-endometrium | 0.0000 | 0.1583 | 0.0000 | undef |
| Uterus myometrium | 0.0000 | 0.0068 | 0.0000 | undef |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0000 | | | |
| Sensory organs | 0.0118 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0278 | Breast | 0.0068 |
| Gastrointestinal | 0.0056 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0164 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 80

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0000 | undef | 0.0000 |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0055 | 0.0000 | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0278 | Breast | 0.0068 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 81

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 82

| | NORMAL | TUMOR | Ratios | |
|---|---|---|---|---|
| | % frequency | % frequency | N/T | T/N |
| Bladder | 0.0000 | 0.0051 | 0.0000 | undef |
| Breast | 0.0077 | 0.0150 | 0.5104 | 1.9593 |
| Small intestine | 0.0184 | 0.0000 | undef | 0.0000 |
| Ovary | 0.0090 | 0.0208 | 0.4317 | 2.3163 |
| Endocrine tissue | 0.0068 | 0.0150 | 0.4528 | 2.2083 |
| Gastrointestinal | 0.0268 | 0.0231 | 1.1597 | 0.8623 |
| Brain | 0.0081 | 0.0123 | 0.6600 | 1.5152 |
| Hematopoietic | 0.0027 | 0.0000 | undef | 0.0000 |
| Skin | 0.0000 | 0.0000 | undef | undef |
| Hepatic | 0.0095 | 0.0065 | 1.4706 | 0.6800 |
| Heart | 0.0011 | 0.0412 | 0.0257 | 38.9113 |

|   |   |   |   |
|---|---|---|---|
| Testicles | 0.0058 | 0.0000 | undef | 0.0000 |
| Lung | 0.0031 | 0.0123 | 0.2540 | 3.9367 |
| Stomach-esophagus | 0.0290 | 0.0000 | undef | 0.0000 |
| Muscle-skeleton | 0.0103 | 0.0060 | 1.7133 | 0.5837 |
| Kidney | 0.0054 | 0.0000 | undef | 0.0000 |
| Pancreas | 0.0050 | 0.0166 | 0.2991 | 3.3428 |
| Penis | 0.0060 | 0.0000 | undef | 0.0000 |
| Prostate | 0.0305 | 0.0554 | 0.5512 | 1.8143 |
| Uterus-endometrium | 0.0000 | 0.1055 | 0.0000 | undef |
| Uterus-myometrium | 0.0000 | 0.0000 | undef | undef |
| Uterus-general | 0.0051 | 0.0000 | undef | 0.0000 |
| Breast hyperplasia | 0.0032 | | | |
| Prostate hyperplasia | 0.0119 | | | |
| Seminal vesicle | 0.0000 | | | |
| Sensory organs | 0.0000 | | | |
| White blood cells | 0.0026 | | | |
| Cervix | 0.0000 | | | |

|   | FETUS % frequency | STANDARDIZED/SUB-TRACTED LIBRARIES % frequency |   |
|---|---|---|---|
| Development | 0.0139 | Breast | 0.0136 |
| Gastrointestinal | 0.0028 | Ovary_n | 0.0000 |
| Brain | 0.0125 | Ovary_t | 0.0253 |
| Hematopoietic | 0.0039 | Endocrine tissue | 0.0000 |
| Skin | 0.0000 | Fetal | 0.0070 |
| Hepatic | 0.0000 | Gastrointestinal | 0.0122 |
| Heart-blood vessels | 0.0036 | Hematopoietic | 0.0000 |
| Lung | 0.0000 | Skin-muscle | 0.0097 |
| Suprarenal gland | 0.0507 | Testicles | 0.0000 |
| Kidney | 0.0000 | Lung | 0.0082 |
| Placenta | 0.0000 | Nerves | 0.0131 |
| Prostate | 0.0000 | Prostate | 0.0205 |
| Sensory organs | 0.0000 | Sensory Organs | 0.0000 |
| | | Uterus_n | 0.0083 |

Electronic Northern for SEQ. ID NO.: 83

|   | NORMAL | TUMOR | Ratios | |
|---|---|---|---|---|
|   | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|   | FETUS % frequency | STANDARDIZED/SUB-TRACTED LIBRARIES % frequency |   |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0050 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 84

|   | NORMAL | TUMOR | Ratios | |
|---|---|---|---|---|
|   | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|   | FETUS % frequency | STANDARDIZED/SUB-TRACTED LIBRARIES % frequency |   |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0254 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 85

|   | NORMAL | TUMOR | Ratios | |
|---|---|---|---|---|
|   | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |

-continued

| | | | |
|---|---|---|---|
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 86

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0068 |
| Sensory organs | 0.0000 | Sensory Organs | 0.0000 |
| | | Uterus_n | 0.0000 |

Electronic Northern for SEQ. ID NO.: 87

| | NORMAL | TUMOR | Ratios | |
|---|---|---|---|---|
| | % frequency | % frequency | N/T | T/N |
| Bladder | 0.0039 | 0.0204 | 0.1907 | 5.2444 |
| Breast | 0.0128 | 0.0075 | 1.7013 | 0.5878 |
| Small intestine | 0.0123 | 0.0165 | 0.7415 | 1.3487 |
| Ovary | 0.0030 | 0.0078 | 0.3838 | 2.6058 |
| Endocrine tissue | 0.0000 | 0.0000 | undef | undef |
| Gastrointestinal | 0.0038 | 0.0139 | 0.2761 | 3.6217 |
| Brain | 0.0007 | 0.0000 | undef | 0.0000 |
| Hematopoietic | 0.0000 | 0.0000 | undef | undef |
| Skin | 0.0110 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0031 | 0.0000 | undef | undef |
| Stomach-esophagus | 0.0097 | 0.0000 | undef | 0.0000 |
| Muscle-skeleton | 0.0000 | 0.0077 | 1.2605 | 0.7933 |
| Kidney | 0.0054 | 0.0000 | undef | undef |
| Pancreas | 0.0050 | 0.0000 | undef | 0.0000 |
| Penis | 0.0000 | 0.0000 | undef | 0.0000 |
| Prostate | 0.0044 | 0.0000 | undef | undef |
| Uterus-endometrium | 0.0068 | 0.0149 | 0.2925 | 3.4192 |
| Uterus-myometrium | 0.0000 | 0.1055 | 0.0640 | 15.6211 |
| Uterus-general | 0.0000 | 0.0000 | undef | undef |
| Breast hyperplasia | 0.0192 | 0.0000 | undef | undef |
| Prostate hyperplasia | 0.0089 | | | |
| Seminal vesicle | 0.0089 | | | |
| Sensory organs | 0.0000 | | | |
| White blood cells | 0.0000 | | | |
| Cervix | 0.0106 | | | |

| | FETUS % frequency | STANDARDIZED/SUB-TRACTED LIBRARIES % frequency | |
|---|---|---|---|
| Development | 0.0000 | Breast | 0.0068 |
| Gastrointestinal | 0.0000 | Ovary_n | 0.0000 |
| Brain | 0.0000 | Ovary_t | 0.0051 |
| Hematopoietic | 0.0000 | Endocrine tissue | 0.0000 |
| Skin | 0.0000 | Fetal | 0.0000 |
| Hepatic | 0.0000 | Gastrointestinal | 0.0122 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0082 |
| Placenta | 0.0000 | Nerves | 0.0000 |
| Prostate | 0.0000 | Prostate | 0.0068 |
| Sensory organs | 0.0000 | Sensory Organs | 0.0000 |
| | | Uterus_n | 0.0000 |

-continued

Electronic Northern for SEQ. ID NO.: 88

| | NORMAL | TUMOR | Ratios | |
| --- | --- | --- | --- | --- |
| | % frequency | % frequency | N/T | T/N |
| Bladder | 0.0000 | 0.0026 | 0.0000 | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0050 | 0.0000 | undef |
| Gastrointestinal | 0.0019 | 0.0000 | undef | 0.0000 |
| Brain | 0.0007 | 0.0010 | 0.7200 | 1.3890 |
| Hematopoietic | 0.0000 | 0.0000 | undef | undef |
| Skin | 0.0000 | 0.0000 | undef | undef |
| Hepatic | 0.0048 | 0.0000 | undef | 0.0000 |
| Heart | 0.0011 | 0.0000 | undef | 0.0000 |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0017 | 0.0000 | undef | 0.0000 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0021 | 0.0000 | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0118 | | | |
| White blood cells | 0.0017 | | | |
| Cervix | 0.0000 | | | |

| | FETUS % frequency | STANDARDIZED/SUB-TRACTED LIBRARIES % frequency | |
| --- | --- | --- | --- |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0114 |
| Lung | 0.0036 | Skin-muscle | 0.0032 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 89

| | NORMAL | TUMOR | Ratios | |
| --- | --- | --- | --- | --- |
| | % frequency | % frequency | N/T | T/N |
| Bladder | 0.0000 | 0.0000 | undef | undef |
| Breast | 0.0013 | 0.0000 | undef | 0.0000 |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0055 | 0.0000 | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
| --- | --- | --- | --- |
| Development | 0.0287 | Breast | 0.0068 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0042 |

Electronic Northern for SEQ. ID NO.: 90

| | NORMAL | TUMOR | Ratios | |
| --- | --- | --- | --- | --- |
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
| --- | --- | --- | --- |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |

-continued

| | | | | |
|---|---|---|---|---|
| Prostate | 0.0000 | Prostate | | 0.0000 |
| Sensory organs | 0.0000 | Sensory Organs | | 0.0000 |
| | | Uterus_n | | 0.0000 |

Electronic Northern for SEQ. ID NO.: 91

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0090 | 0.0038 | 2.3818 | 0.4198 |
| Small intestine | 0.0000 | 0.0000 | undef | undef |
| Ovary | 0.0030 | 0.0052 | 0.5756 | 1.7372 |
| Endocrine tissue | 0.0034 | 0.0025 | 1.3585 | 0.7361 |
| Gastrointestinal | 0.0096 | 0.0000 | undef | 0.0000 |
| Brain | 0.0037 | 0.0021 | 1.7999 | 0.5556 |
| Hematopoietic | 0.0027 | 0.0000 | undef | 0.0000 |
| Skin | 0.0110 | 0.0847 | 0.1300 | 7.6946 |
| Hepatic | 0.0095 | 0.0065 | 1.4706 | 0.6800 |
| Heart | 0.0042 | 0.0000 | undef | 0.0000 |
| Testicles | 0.0000 | 0.0117 | 0.0000 | undef |
| Lung | 0.0010 | 0.0020 | 0.5080 | 1.9684 |
| Stomach-esophagus | 0.0000 | 0.0077 | 0.0000 | undef |
| Muscle-skeleton | 0.0000 | 0.0000 | undef | undef |
| Kidney | 0.0027 | 0.0000 | undef | 0.0000 |
| Pancreas | 0.0017 | 0.0166 | 0.0997 | 10.0285 |
| Penis | 0.0030 | 0.0000 | undef | 0.0000 |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0118 | | | |
| White blood cells | 0.0026 | | | |
| Cervix | 0.0106 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0111 | Ovary_n | 0.0000 |
| Brain | 0.0063 | Ovary_t | 0.0000 |
| Hematopoietic | 0.0000 | Endocrine tissue | 0.0000 |
| Skin | 0.0000 | Fetal | 0.0041 |
| Hepatic | 0.0000 | Gastrointestinal | 0.0000 |
| Heart-blood vessels | 0.0036 | Hematopoietic | 0.0057 |
| Lung | 0.0108 | Skin-muscle | 0.0065 |
| Suprarenal gland | 0.0000 | Testicles | 0.0000 |
| Kidney | 0.0000 | Lung | 0.0000 |
| Placenta | 0.0061 | Nerves | 0.0050 |
| Prostate | 0.0249 | Prostate | 0.0000 |
| Sensory organs | 0.0000 | Sensory Organs | 0.0000 |
| | | Uterus_n | 0.0125 |

Electronic Northern for SEQ. ID NO.: 92

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0017 | 0.0000 | undef | 0.0000 |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 93

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0000 | 0.0020 | 0.0000 | undef |
| Stomach-esophagus | 0.0000 | 0.0000 | undef | undef |
| Muscle-skeleton | 0.0000 | 0.0060 | 0.0000 | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0000 | Hematopoietic | 0.0000 |

-continued

| | | | | |
|---|---|---|---|---|
| Lung | 0.0000 | Skin-muscle | | 0.0000 |
| Suprarenal gland | 0.0000 | Testicles | | 0.0000 |
| Kidney | 0.0000 | Lung | | 0.0000 |
| Placenta | 0.0000 | Nerves | | 0.0000 |
| Prostate | 0.0000 | Prostate | | 0.0000 |
| Sensory organs | 0.0000 | Sensory Organs | | 0.0000 |
| | | Uterus_n | | 0.0000 |

Electronic Northern for SEQ. ID NO.: 94

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0000 | undef | 0.0000 |
| Small intestine | 0.0000 | 0.0165 | 0.0000 | undef |
| Ovary | 0.0000 | 0.0000 | undef | undef |
| Endocrine tissue | 0.0051 | 0.0075 | 0.6792 | 1.4722 |
| Gastrointestinal | 0.0000 | 0.0000 | undef | undef |
| Brain | 0.0022 | 0.0010 | 2.1599 | 0.4630 |
| Hematopoietic | 0.0000 | 0.0000 | undef | undef |
| Skin | 0.0037 | 0.0000 | undef | 0.0000 |
| Hepatic | 0.0000 | 0.0065 | 0.0000 | undef |
| Heart | 0.0021 | 0.0000 | undef | 0.0000 |
| Testicles | 0.0115 | 0.0000 | undef | 0.0000 |
| Lung | 0.0010 | 0.0020 | 0.5080 | 1.9684 |
| Stomach-esophagus | 0.0000 | 0.0000 | undef | undef |
| Muscle-skeleton | 0.0034 | 0.0000 | undef | 0.0000 |
| Kidney | 0.0000 | 0.0000 | undef | undef |
| Pancreas | 0.0000 | 0.0000 | undef | undef |
| Penis | 0.0030 | 0.0000 | undef | 0.0000 |
| Prostate | 0.0044 | 0.0000 | undef | 0.0000 |
| Uterus-endometrium | 0.0000 | 0.1055 | 0.0000 | undef |
| Uterus-myometrium | 0.0076 | 0.0136 | 0.5611 | 1.7821 |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0089 | | | |
| Sensory organs | 0.0000 | | | |
| White blood cells | 0.0000 | | | |
| Cervix | 0.0000 | | | |

| | FETUS | STANDARDIZED/SUB-TRACTED LIBRARIES | |
|---|---|---|---|
| | % frequency | | % frequency |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.2513 | Fetal | 0.0029 |
| Hepatic | 0.0000 | Gastrointestinal | 0.0000 |
| Heart-blood vessels | 0.0107 | Hematopoietic | 0.0000 |
| Lung | 0.0036 | Skin-muscle | 0.0065 |
| Suprarenal gland | 0.0000 | Testicles | 0.0154 |
| Kidney | 0.0000 | Lung | 0.0000 |
| Placenta | 0.0121 | Nerves | 0.0010 |
| Prostate | 0.0000 | Prostate | 0.0000 |
| Sensory organs | 0.0000 | Sensory Organs | 0.0000 |
| | | Uterus_n | 0.0208 |

Electronic Northern for SEQ. ID NO.: 95

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.0000 | undef | undef |
| Uterus-myometrium | 0.0000 | 0.1055 | 0.0000 | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS | STANDARDIZED/SUB-TRACTED LIBRARIES | |
|---|---|---|---|
| | % frequency | | % frequency |
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 96

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0030 | 0.0000 | undef | 0.0000 |
| Endocrine tissue | 0.0017 | 0.0000 | undef | 0.0000 |
| Gastrointestinal | 0.0000 | 0.0000 | undef | undef |
| Brain | 0.0007 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

| | FETUS | STANDARDIZED/SUB-TRACTED LIBRARIES | |
|---|---|---|---|
| | % frequency | | % frequency |
| Development | 0.0000 | Breast | 0.0000 |
| Gastrointestinal | 0.0000 | Ovary_n | 0.0000 |
| Brain | 0.0000 | Ovary_t | 0.0000 |

Electronic Northern for SEQ. ID NO.: 97

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0019 | 0.6805 | 1.4694 |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0022 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0117 | 0.0000 | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0055 | 0.0000 | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0010 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 98

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0000 | 0.0000 | undef | undef |
| Small intestine | 0.0000 | 0.0000 | undef | undef |
| Ovary | 0.0030 | 0.0026 | 1.1513 | 0.8686 |
| Endocrine tissue | 0.0000 | 0.0000 | undef | undef |
| Gastrointestinal | 0.0038 | 0.0000 | undef | 0.0000 |
| Brain | 0.0000 | 0.0000 | undef | undef |
| Hematopoietic | 0.0040 | 0.0000 | undef | 0.0000 |
| Skin | 0.0330 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0055 | 0.0000 | undef |
| Penis | 0.0000 | 0.0533 | 0.0000 | undef |
| Prostate | 0.0022 | 0.0021 | 1.0236 | 0.9769 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0064 | | | |
| Prostate hyperplasia | 0.0000 | | | |
| Seminal vesicle | 0.0000 | | | |
| Sensory organs | 0.0000 | | | |
| White blood cells | 0.0017 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0063 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0030 |
| Prostate | 0.0000 | Prostate | 0.0000 |
| Sensory organs | 0.0000 | Sensory Organs | 0.0000 |
| | | Uterus_n | 0.0083 |

Electronic Northern for SEQ. ID NO.: 99

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0057 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 100

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0051 | 0.0025 | 2.0377 | 0.4907 |
| Gastrointestinal | 0.0000 | 0.0000 | undef | undef |
| Brain | 0.0022 | 0.0010 | 2.1599 | 0.4630 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0032 | 0.0000 | undef | 0.0000 |
| Testicles | 0.0000 | 0.0000 | undef | undef |
| Lung | 0.0052 | 0.0020 | 2.5402 | 0.3937 |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0000 | 0.0000 | undef | undef |
| Penis | 0.0030 | 0.0000 | undef | 0.0000 |
| Prostate | 0.0000 | 0.0000 | undef | undef |
| Uterus-endometrium | 0.0000 | 0.1055 | 0.0000 | undef |
| Uterus-myometrium | 0.0000 | 0.0068 | 0.0000 | undef |
| Uterus-general | 0.0000 | 0.0000 | undef | undef |
| Breast hyperplasia | 0.0032 |  |  |  |
| Prostate hyperplasia | 0.0000 |  |  |  |
| Seminal vesicle | 0.0089 |  |  |  |
| Sensory organs | 0.0000 |  |  |  |
| White blood cells | 0.0009 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0036 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0061 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 101

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 |  |  |  |
| Prostate hyperplasia | 0.0000 |  |  |  |
| Seminal vesicle | 0.0000 |  |  |  |
| Sensory organs | 0.0000 |  |  |  |
| White blood cells | 0.0000 |  |  |  |
| Cervix | 0.0000 |  |  |  |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 102

|  | NORMAL | TUMOR | Ratios | |
|---|---|---|---|---|
|  | % frequency | % frequency | N/T | T/N |
| Bladder | 0.0039 | 0.0000 | undef | 0.0000 |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |

-continued

| | | | | |
|---|---|---|---|---|
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 103

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0064 | 0.0000 | undef | 0.0000 |
| Small intestine | 0.0000 | 0.0165 | 0.0000 | undef |
| Ovary | 0.0000 | 0.0078 | 0.0000 | undef |
| Endocrine tissue | 0.0000 | 0.0025 | 0.0000 | undef |
| Gastrointestinal | 0.0000 | 0.0000 | undef | undef |
| Brain | 0.0015 | 0.0021 | 0.7200 | 1.3890 |
| Hematopoietic | 0.0013 | 0.0000 | undef | 0.0000 |
| Skin | 0.0000 | 0.0000 | undef | undef |
| Hepatic | 0.0000 | 0.0000 | undef | undef |
| Heart | 0.0032 | 0.0000 | undef | 0.0000 |
| Testicles | 0.0000 | 0.0000 | undef | undef |
| Lung | 0.0010 | 0.0041 | 0.2540 | 3.9367 |
| Stomach-esophagus | 0.0000 | 0.0077 | 0.0000 | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0068 | 0.0000 | undef |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0032 |
| Lung | 0.0000 | Skin-muscle | 0.0000 |
| Suprarenal gland | 0.0000 | Testicles | 0.0000 |
| Kidney | 0.0000 | Lung | 0.0040 |
| Placenta | 0.0000 | Nerves | 0.0000 |
| Prostate | 0.0249 | Prostate | 0.0000 |
| Sensory organs | 0.0000 | Sensory Organs | 0.0000 |
| | | Uterus_n | 0.0000 |

Electronic Northern for SEQ. ID NO.: 104

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0010 | 0.0020 | 0.5080 | 1.9684 |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 105

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0090 | 0.0038 | 2.3818 | 0.4198 |
| Small intestine | 0.0000 | 0.0000 | undef | undef |
| Ovary | 0.0030 | 0.0052 | 0.5756 | 1.7372 |
| Endocrine tissue | 0.0034 | 0.0025 | 1.3585 | 0.7361 |
| Gastrointestinal | 0.0096 | 0.0000 | undef | 0.0000 |
| Brain | 0.0037 | 0.0021 | 0.7999 | 0.5556 |
| Hematopoietic | 0.0027 | 0.0000 | undef | 0.0000 |
| Skin | 0.0110 | 0.0847 | 0.1300 | 7.6946 |
| Hepatic | 0.0095 | 0.0065 | 1.4706 | 0.6800 |
| Heart | 0.0042 | 0.0000 | undef | 0.0000 |
| Testicles | 0.0000 | 0.0117 | 0.0000 | undef |
| Lung | 0.0010 | 0.0020 | 0.5080 | 1.9684 |
| Stomach-esophagus | 0.0000 | 0.0077 | 0.0000 | undef |
| Muscle-skeleton | 0.0000 | 0.0000 | undef | undef |

-continued

| | | | | |
|---|---|---|---|---|
| Kidney | 0.0027 | 0.0000 | undef | 0.0000 |
| Pancreas | 0.0017 | 0.0166 | 0.0997 | 10.0285 |
| Penis | 0.0030 | 0.0000 | undef | 0.0000 |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0118 | | | |
| White blood cells | 0.0026 | | | |
| Cervix | 0.0106 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0111 | Ovary_n | 0.0000 |
| Brain | 0.0063 | Ovary_t | 0.0000 |
| Hematopoietic | 0.0000 | Endocrine tissue | 0.0000 |
| Skin | 0.0000 | Fetal | 0.0041 |
| Hepatic | 0.0000 | Gastrointestinal | 0.0000 |
| Heart-blood vessels | 0.0036 | Hematopoietic | 0.0057 |
| Lung | 0.0108 | Skin-muscle | 0.0065 |
| Suprarenal gland | 0.0000 | Testicles | 0.0000 |
| Kidney | 0.0000 | Lung | 0.0000 |
| Placenta | 0.0061 | Nerves | 0.0050 |
| Prostate | 0.0249 | Prostate | 0.0000 |
| Sensory organs | 0.0000 | Sensory Organs | 0.0000 |
| | | Uterus_n | 0.0125 |

Electronic Northern for SEQ. ID NO.: 106

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0007 | 0.0000 | undef | 0.0000 |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 107

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0030 | 0.0000 | undef | 0.0000 |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 108

| | NORMAL % frequency | TUMOR % frequency | Ratios N/T | T/N |
|---|---|---|---|---|
| Bladder | 0.0000 | 0.0051 | 0.0000 | undef |
| Breast | 0.0051 | 0.0038 | 1.3611 | 0.7347 |
| Small intestine | 0.0031 | 0.0165 | 0.1854 | 5.3946 |
| Ovary | 0.0000 | 0.0026 | 0.0000 | undef |
| Endocrine tissue | 0.0034 | 0.0050 | 0.6792 | 1.4722 |
| Gastrointestinal | 0.0019 | 0.0000 | undef | 0.0000 |
| Brain | 0.0037 | 0.0062 | 0.6000 | 1.6668 |
| Hematopoietic | 0.0040 | 0.0000 | undef | 0.0000 |
| Skin | 0.0000 | 0.0000 | undef | undef |
| Hepatic | 0.0048 | 0.0000 | undef | 0.0000 |
| Heart | 0.0064 | 0.0000 | undef | 0.0000 |

-continued

| | | | | |
|---|---|---|---|---|
| Testicles | 0.0000 | 0.0000 | undef | undef |
| Lung | 0.0031 | 0.0041 | 0.7621 | 1.3122 |
| Stomach-esophagus | 0.0000 | 0.0000 | undef | undef |
| Muscle-skeleton | 0.0017 | 0.0000 | undef | 0.0000 |
| Kidney | 0.0000 | 0.0000 | undef | undef |
| Pancreas | 0.0000 | 0.0000 | undef | undef |
| Penis | 0.0030 | 0.0267 | 0.1123 | 8.9035 |
| Prostate | 0.0000 | 0.0000 | undef | undef |
| Uterus-endometrium | 0.0068 | 0.1055 | 0.0640 | 15.6211 |
| Uterus-myometrium | 0.0152 | 0.0068 | 2.2445 | 0.4455 |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0118 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0136 |
| Gastrointestinal | 0.0028 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0035 |
| Hepatic | 0.0000 | Gastrointestinal | 0.0000 |
| Heart-blood vessels | 0.0000 | Hematopoietic | 0.0057 |
| Lung | 0.0036 | Skin-muscle | 0.0032 |
| Suprarenal gland | 0.0000 | Testicles | 0.0077 |
| Kidney | 0.0000 | Lung | 0.0164 |
| Placenta | 0.0000 | Nerves | 0.0030 |
| Prostate | 0.0249 | Prostate | 0.0000 |
| Sensory organs | 0.0126 | Sensory Organs | 0.0310 |
| | | Uterus_n | 0.0042 |

Electronic Northern for SEQ. ID NO.: 109

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 110

| | NORMAL % frequency | TUMOR % frequency | Ratios N/T | T/N |
|---|---|---|---|---|
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0068 |
| Sensory organs | 0.0000 | Sensory Organs | 0.0000 |
| | | Uterus_n | 0.0000 |

Electronic Northern for SEQ. ID NO.: 111

| | NORMAL % frequency | TUMOR % frequency | Ratios N/T | T/N |
|---|---|---|---|---|
| Bladder | 0.0000 | 0.0000 | undef | undef |
| Breast | 0.0051 | 0.0000 | undef | 0.0000 |
| Small intestine | 0.0000 | 0.0000 | undef | undef |
| Ovary | 0.0000 | 0.0052 | 0.0000 | undef |
| Endocrine tissue | 0.0017 | 0.0000 | undef | 0.0000 |
| Gastrointestinal | 0.0000 | 0.0000 | undef | undef |
| Brain | 0.0022 | 0.0021 | 1.0799 | 0.9260 |

-continued

| | | | |
|---|---|---|---|
| Hematopoietic | 0.0027 | 0.0000 | undef | 0.0000 |
| Skin | 0.0037 | 0.0000 | undef | 0.0000 |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0010 | 0.0041 | 0.2540 | 3.9367 |
| Stomach-esophagus | 0.0000 | 0.0000 | undef | undef |
| Muscle-skeleton | 0.0034 | 0.0060 | 0.5711 | 1.7510 |
| Kidney | 0.0000 | 0.0000 | undef | undef |
| Pancreas | 0.0017 | 0.0000 | undef | 0.0000 |
| Penis | 0.0000 | 0.0000 | undef | undef |
| Prostate | 0.0022 | 0.0000 | undef | 0.0000 |
| Uterus-endometrium | 0.0000 | 0.1583 | 0.0000 | undef |
| Uterus-myometrium | 0.0076 | 0.0000 | undef | 0.0000 |
| Uterus-general | 0.0000 | 0.0000 | undef | undef |
| Breast hyperplasia | 0.0032 | | | |
| Prostate hyperplasia | 0.0089 | | | |
| Seminal vesicle | 0.0089 | | | |
| Sensory organs | 0.0000 | | | |
| White blood cells | 0.0000 | | | |
| Cervix | 0.0106 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0051 |
| Hematopoietic | 0.0039 | Endocrine tissue | 0.0000 |
| Skin | 0.0000 | Fetal | 0.0070 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0231 |
| Kidney | 0.0000 | Lung | 0.0164 |
| Placenta | 0.0000 | Nerves | 0.0050 |
| Prostate | 0.0000 | Prostate | 0.0000 |
| Sensory organs | 0.0000 | Sensory Organs | 0.0000 |
| | | Uterus_n | 0.0125 |

Electronic Northern for SEQ. ID NO.: 112

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0017 | 0.0000 | undef | 0.0000 |
| Gastrointestinal | 0.0019 | 0.0000 | undef | 0.0000 |
| Brain | 0.0022 | 0.0010 | 2.1599 | 0.4630 |
| Hematopoietic | 0.0027 | 0.0000 | undef | 0.0000 |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0097 | 0.0000 | undef | 0.0000 |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0076 | 0.0000 | undef | 0.0000 |
| Uterus-general | 0.0051 | 0.0000 | undef | 0.0000 |
| Breast hyperplasia | 0.0032 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0125 |

Electronic Northern for SEQ. ID NO.: 113

| | NORMAL | TUMOR | Ratios | |
|---|---|---|---|---|
| | % frequency | % frequency | N/T | T/N |
| Bladder | 0.0000 | 0.0077 | 0.0000 | undef |
| Breast | 0.0038 | 0.0038 | 1.0208 | 0.9796 |
| Small intestine | 0.0031 | 0.0165 | 0.1854 | 5.3946 |
| Ovary | 0.0000 | 0.0026 | 0.0000 | undef |
| Endocrine tissue | 0.0051 | 0.0050 | 0.0189 | 0.9815 |
| Gastrointestinal | 0.0019 | 0.0000 | undef | 0.0000 |
| Brain | 0.0037 | 0.0062 | 0.6000 | 1.6668 |
| Hematopoietic | 0.0067 | 0.0000 | undef | 0.0000 |
| Skin | 0.0000 | 0.0000 | undef | undef |
| Hepatic | 0.0048 | 0.0000 | undef | 0.0000 |
| Heart | 0.0064 | 0.0000 | undef | 0.0000 |
| Testicles | 0.0000 | 0.0000 | undef | undef |
| Lung | 0.0031 | 0.0041 | 0.7621 | 1.3122 |
| Stomach-esophagus | 0.0000 | 0.0000 | undef | undef |
| Muscle-skeleton | 0.0017 | 0.0000 | undef | 0.0000 |
| Kidney | 0.0000 | 0.0000 | undef | undef |
| Pancreas | 0.0000 | 0.0000 | undef | undef |
| Penis | 0.0060 | 0.0267 | 0.2246 | 4.4517 |
| Prostate | 0.0000 | 0.0021 | 0.0000 | undef |
| Uterus-endometrium | 0.0068 | 0.1055 | 0.0640 | 15.6211 |
| Uterus-myometrium | 0.0152 | 0.0068 | 2.2445 | 0.4455 |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0118 | | | |
| White blood cells | 0.0017 | | | |
| Cervix | 0.0000 | | | |

| | FETUS<br>% frequency | STANDARDIZED/SUB-<br>TRACTED LIBRARIES<br>% frequency | |
|---|---|---|---|
| Development | 0.0000 | Breast | 0.0136 |
| Gastrointestinal | 0.0028 | Ovary_n | 0.0000 |
| Brain | 0.0000 | Ovary_t | 0.0000 |
| Hematopoietic | 0.0039 | Endocrine tissue | 0.0000 |
| Skin | 0.0000 | Fetal | 0.0052 |
| Hepatic | 0.0000 | Gastrointestinal | 0.0000 |
| Heart-blood vessels | 0.0036 | Hematopoietic | 0.0057 |
| Lung | 0.0036 | Skin-muscle | 0.0032 |
| Suprarenal gland | 0.0000 | Testicles | 0.0077 |
| Kidney | 0.0000 | Lung | 0.0164 |
| Placenta | 0.0000 | Nerves | 0.0030 |
| Prostate | 0.0249 | Prostate | 0.0000 |
| Sensory organs | 0.0126 | Sensory Organs | 0.0310 |
| | | Uterus_n | 0.0042 |

-continued

Electronic Northern for SEQ. ID NO.: 114

|  | NORMAL | TUMOR | Ratios | |
|---|---|---|---|---|
|  | % frequency | % frequency | N/T | T/N |
| Bladder | 0.0156 | 0.0000 | undef | 0.0000 |
| Breast | 0.0013 | 0.0019 | 0.6815 | 1.4694 |
| Small intestine | 0.0000 | 0.0000 | undef | undef |
| Ovary | 0.0060 | 0.0078 | 0.7675 | 1.3029 |
| Endocrine tissue | 0.0000 | 0.0025 | 0.0000 | undef |
| Gastrointestinal | 0.0038 | 0.0093 | 0.4142 | 2.4145 |
| Brain | 0.0022 | 0.0021 | 1.0799 | 0.9260 |
| Hematopoietic | 0.0027 | 0.0000 | undef | 0.0000 |
| Skin | 0.0110 | 0.0000 | undef | 0.0000 |
| Hepatic | 0.0000 | 0.0000 | undef | undef |
| Heart | 0.0095 | 0.0412 | 0.2313 | 4.3235 |
| Testicles | 0.0000 | 0.0000 | undef | undef |
| Lung | 0.0031 | 0.0164 | 0.1905 | 5.2490 |
| Stomach-esophagus | 0.0193 | 0.0000 | undef | 0.0000 |
| Muscle-skeleton | 0.0069 | 0.0180 | 0.3807 | 2.6265 |
| Kidney | 0.0027 | 0.0000 | undef | 0.0000 |
| Pancreas | 0.0000 | 0.0000 | undef | undef |
| Penis | 0.0030 | 0.0000 | undef | 0.0000 |
| Prostate | 0.0022 | 0.0064 | 0.3412 | 2.9308 |
| Uterus-endometrium | 0.0068 | 0.2111 | 0.0320 | 31.2422 |
| Uterus-myometrium | 0.0000 | 0.0204 | 0.0000 | undef |
| Uterus-general | 0.0102 | 0.0000 | undef | 0.0000 |
| Breast hyperplasia | 0.0032 | | | |
| Prostate hyperplasia | 0.0089 | | | |
| Seminal vesicle | 0.0000 | | | |
| Sensory organs | 0.0000 | | | |
| White blood cells | 0.0017 | | | |
| Cervix | 0.0106 | | | |

|  | FETUS % frequency | STANDARDIZED/SUB-TRACTED LIBRARIES % frequency |  |
|---|---|---|---|
| Development | 0.0139 | Breast | 0.0000 |
| Gastrointestinal | 0.0000 | Ovary_n | 0.1595 |
| Brain | 0.0000 | Ovary_t | 0.0000 |
| Hematopoietic | 0.0039 | Endocrine tissue | 0.0000 |
| Skin | 0.0000 | Fetal | 0.0087 |
| Hepatic | 0.0260 | Gastrointestinal | 0.0244 |
| Heart-blood vessels | 0.0107 | Hematopoietic | 0.0057 |
| Lung | 0.0000 | Skin-muscle | 0.0356 |
| Suprarenal gland | 0.0254 | Testicles | 0.0000 |
| Kidney | 0.0062 | Lung | 0.0164 |
| Placenta | 0.0061 | Nerves | 0.0010 |
| Prostate | 0.0000 | Prostate | 0.0000 |
| Sensory organs | 0.0000 | Sensory Organs | 0.0000 |
|  |  | Uterus_n | 0.0250 |

Electronic Northern for SEQ. ID NO.: 115

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0058 | 0.0000 | undef | 0.0000 |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0017 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 116

|  | NORMAL | TUMOR | Ratios | |
|---|---|---|---|---|
|  | % frequency | % frequency | N/T | T/N |
| Bladder | 0.0039 | 0.0077 | 0.5085 | 1.9666 |
| Breast | 0.0128 | 0.0000 | undef | 0.0000 |
| Small intestine | 0.0061 | 0.0165 | 0.3707 | 2.6973 |
| Ovary | 0.0060 | 0.0000 | undef | 0.0000 |
| Endocrine tissue | 0.0068 | 0.0050 | 1.3585 | 0.7361 |
| Gastrointestinal | 0.0038 | 0.0046 | 0.8283 | 1.2072 |
| Brain | 0.0037 | 0.0051 | 0.7200 | 1.3890 |
| Hematopoietic | 0.0027 | 0.0000 | undef | 0.0000 |
| Skin | 0.0147 | 0.0000 | undef | 0.0000 |
| Hepatic | 0.0000 | 0.0000 | undef | undef |
| Heart | 0.0042 | 0.0137 | 0.3084 | 3.2426 |
| Testicles | 0.0058 | 0.0000 | undef | 0.0000 |
| Lung | 0.0042 | 0.0041 | 1.0161 | 0.9842 |
| Stomach-esophagus | 0.0000 | 0.0000 | undef | undef |
| Muscle-skeleton | 0.0086 | 0.0000 | undef | 0.0000 |
| Kidney | 0.0054 | 0.0068 | 0.7930 | 1.2610 |
| Pancreas | 0.0033 | 0.0000 | undef | 0.0000 |
| Penis | 0.0090 | 0.0000 | undef | 0.0000 |
| Prostate | 0.0022 | 0.0043 | 0.5118 | 1.9538 |
| Uterus-endometrium | 0.0068 | 0.1055 | 0.0640 | 15.6211 |
| Uterus-myometrium | 0.0076 | 0.0000 | undef | 0.0000 |
| Uterus-general | 0.0051 | 0.0000 | undef | 0.0000 |
| Breast hyperplasia | 0.0128 | | | |
| Prostate hyperplasia | 0.0089 | | | |
| Seminal vesicle | 0.0000 | | | |
| Sensory organs | 0.0118 | | | |
| White blood cells | 0.0061 | | | |
| Cervix | 0.0106 | | | |

|  | FETUS % frequency | STANDARDIZED/SUB-TRACTED LIBRARIES % frequency |  |
|---|---|---|---|
| Development | 0.0139 | Breast | 0.0000 |
| Gastrointestinal | 0.0056 | Ovary_n | 0.0000 |
| Brain | 0.0000 | Ovary_t | 0.0051 |
| Hematopoietic | 0.0039 | Endocrine tissue | 0.0245 |
| Skin | 0.0000 | Fetal | 0.0076 |
| Hepatic | 0.0000 | Gastrointestinal | 0.0000 |
| Heart-blood vessels | 0.0000 | Hematopoietic | 0.0228 |
| Lung | 0.0036 | Skin-muscle | 0.0227 |
| Suprarenal gland | 0.0000 | Testicles | 0.0000 |
| Kidney | 0.0000 | Lung | 0.0000 |
| Placenta | 0.0061 | Nerves | 0.0060 |

-continued

| | | | |
|---|---|---|---|
| Prostate | 0.0000 | Prostate | 0.0068 |
| Sensory organs | 0.0000 | Sensory Organs | 0.0155 |
| | | Uterus_n | 0.0083 |

Electronic Northern for SEQ. ID NO.: 117

| | NORMAL | TUMOR | Ratios | |
|---|---|---|---|---|
| | % frequency | % frequency | N/T | T/N |
| Bladder | 0.0039 | 0.0026 | 1.5254 | 0.6555 |
| Breast | 0.0038 | 0.0094 | 0.4083 | 2.4491 |
| Small intestine | 0.0061 | 0.0000 | undef | 0.0000 |
| Ovary | 0.0030 | 0.0052 | 0.5756 | 1.7372 |
| Endocrine tissue | 0.0000 | 0.0050 | 0.0000 | undef |
| Gastrointestinal | 0.0019 | 0.0046 | 0.4142 | 2.4145 |
| Brain | 0.0037 | 0.0000 | undef | 0.0000 |
| Hematopoietic | 0.0040 | 0.0000 | undef | 0.0000 |
| Skin | 0.0037 | 0.0000 | undef | 0.0000 |
| Hepatic | 0.0048 | 0.0000 | undef | 0.0000 |
| Heart | 0.0021 | 0.0137 | 0.1542 | 6.4853 |
| Testicles | 0.0000 | 0.0000 | undef | undef |
| Lung | 0.0000 | 0.0041 | 0.0000 | undef |
| Stomach-esophagus | 0.0000 | 0.0000 | undef | undef |
| Muscle-skeleton | 0.0000 | 0.0000 | undef | undef |
| Kidney | 0.0027 | 0.0000 | undef | 0.0000 |
| Pancreas | 0.0000 | 0.0000 | undef | undef |
| Penis | 0.0030 | 0.0000 | undef | 0.0000 |
| Prostate | 0.0044 | 0.0128 | 0.3412 | 2.9308 |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0096 | | | |
| Prostate hyperplasia | 0.0030 | | | |
| Seminal vesicle | 0.0000 | | | |
| Sensory organs | 0.0000 | | | |
| White blood cells | 0.0087 | | | |
| Cervix | 0.0000 | | | |

| | FETUS % frequency | STANDARDIZED/SUB-TRACTED LIBRARIES % frequency | | |
|---|---|---|---|---|
| Development | 0.0000 | Breast | | 0.0000 |
| Gastrointestinal | 0.0000 | Ovary_n | | 0.0000 |
| Brain | 0.0000 | Ovary_t | | 0.0101 |
| Hematopoietic | 0.0000 | Endocrine tissue | | 0.0000 |
| Skin | 0.0000 | Fetal | | 0.0041 |
| Hepatic | 0.0000 | Gastrointestinal | | 0.0000 |
| Heart-blood vessels | 0.0000 | Hematopoietic | | 0.0456 |
| Lung | 0.0000 | Skin-muscle | | 0.0000 |
| Suprarenal gland | 0.0000 | Testicles | | 0.0154 |
| Kidney | 0.0000 | Lung | | 0.0000 |
| Placenta | 0.0000 | Nerves | | 0.0010 |
| Prostate | 0.0000 | Prostate | | 0.0068 |
| Sensory organs | 0.0000 | Sensory Organs | | 0.0000 |
| | | Uterus_n | | 0.0042 |

Electronic Northern for SEQ. ID NO.: 118

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0026 | 0.0000 | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | | |
|---|---|---|---|---|
| Development | 0.0000 | Breast | | 0.0000 |
| Gastrointestinal | 0.0000 | Ovary_n | | 0.0000 |
| Brain | 0.0000 | Ovary_t | | 0.0000 |
| Hematopoietic | 0.0000 | Endocrine tissue | | 0.0000 |
| Skin | 0.0000 | Fetal | | 0.0000 |
| Hepatic | 0.0000 | Gastrointestinal | | 0.0000 |
| Heart-blood vessels | 0.0000 | Hematopoietic | | 0.0000 |
| Lung | 0.0000 | Skin-muscle | | 0.0000 |
| Suprarenal gland | 0.0000 | Testicles | | 0.0077 |
| Kidney | 0.0000 | Lung | | 0.0000 |
| Placenta | 0.0000 | Nerves | | 0.0000 |
| Prostate | 0.0000 | Prostate | | 0.0000 |
| Sensory organs | 0.0000 | Sensory Organs | | 0.0000 |
| | | Uterus_n | | 0.0000 |

Electronic Northern for SEQ. ID NO.: 119

| | NORMAL | TUMOR | Ratios | |
|---|---|---|---|---|
| | % frequency | % frequency | N/T | T/N |
| Bladder | 0.0039 | 0.0000 | undef | 0.0000 |
| Breast | 0.0013 | 0.0038 | 0.3403 | 2.9389 |
| Small intestine | 0.0000 | 0.0000 | undef | undef |
| Ovary | 0.0000 | 0.0052 | 0.0000 | undef |
| Endocrine tissue | 0.0034 | 0.0050 | 0.6792 | 1.4722 |
| Gastrointestinal | 0.0019 | 0.0000 | undef | 0.0000 |
| Brain | 0.0007 | 0.0041 | 0.1800 | 5.5559 |
| Hematopoietic | 0.0040 | 0.0000 | undef | 0.0000 |
| Skin | 0.0037 | 0.0000 | undef | 0.0000 |
| Hepatic | 0.0000 | 0.0000 | undef | undef |
| Heart | 0.0011 | 0.0000 | undef | 0.0000 |
| Testicles | 0.0000 | 0.0000 | undef | undef |
| Lung | 0.0010 | 0.0000 | undef | 0.0000 |
| Stomach-esophagus | 0.0000 | 0.0153 | 0.0000 | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0022 | 0.0021 | 1.0236 | 0.9769 |
| Uterus-endometrium | 0.0068 | 0.1055 | 0.0640 | 15.6211 |
| Uterus-myometrium | 0.0000 | 0.0000 | undef | undef |
| Uterus-general | 0.0102 | 0.0000 | undef | 0.0000 |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0026 | | | |
| Cervix | 0.0000 | | | |

| | FETUS % frequency | STANDARDIZED/SUB-TRACTED LIBRARIES % frequency | | |
|---|---|---|---|---|
| Development | 0.0000 | Breast | | 0.0000 |
| Gastrointestinal | 0.0028 | Ovary_n | | 0.0000 |
| Brain | 0.0000 | Ovary_t | | 0.0000 |
| Hematopoietic | 0.0000 | Endocrine tissue | | 0.0000 |
| Skin | 0.0000 | Fetal | | 0.0023 |
| Hepatic | 0.0000 | Gastrointestinal | | 0.0000 |
| Heart-blood vessels | 0.0000 | Hematopoietic | | 0.0000 |

-continued

| | | | | |
|---|---|---|---|---|
| Lung | 0.0000 | Skin-muscle | | 0.0032 |
| Suprarenal gland | 0.0000 | Testicles | | 0.0000 |
| Kidney | 0.0000 | Lung | | 0.0000 |
| Placenta | 0.0061 | Nerves | | 0.0110 |
| Prostate | 0.0000 | Prostate | | 0.0000 |
| Sensory organs | 0.0126 | Sensory Organs | | 0.0155 |
| | | Uterus_n | | 0.0000 |

Electronic Northern for SEQ. ID NO.: 120

| | NORMAL | TUMOR | Ratios | |
|---|---|---|---|---|
| | % frequency | % frequency | N/T | T/N |
| Bladder | 0.0195 | 0.0077 | 2.5424 | 0.3933 |
| Breast | 0.0090 | 0.0075 | 1.1909 | 0.8397 |
| Small intestine | 0.0031 | 0.0000 | undef | 0.0000 |
| Ovary | 0.0060 | 0.0078 | 0.7675 | 1.3029 |
| Endocrine tissue | 0.0068 | 0.0125 | 0.5434 | 1.8403 |
| Gastrointestinal | 0.0038 | 0.0093 | 0.4142 | 2.4145 |
| Brain | 0.0059 | 0.0031 | 1.9199 | 0.5209 |
| Hematopoietic | 0.0027 | 0.0758 | 0.0353 | 28.3379 |
| Skin | 0.0037 | 0.0000 | undef | 0.0000 |
| Hepatic | 0.0000 | 0.0065 | 0.0000 | undef |
| Heart | 0.0042 | 0.0000 | undef | 0.0000 |
| Testicles | 0.0000 | 0.0000 | undef | undef |
| Lung | 0.0042 | 0.0041 | 1.0161 | 0.9842 |
| Stomach-esophagus | 0.0000 | 0.0000 | undef | undef |
| Muscle-skeleton | 0.0034 | 0.0060 | 0.5711 | 1.7510 |
| Kidney | 0.0109 | 0.0137 | 0.7930 | 1.2610 |
| Pancreas | 0.0033 | 0.0000 | undef | 0.0000 |
| Penis | 0.0150 | 0.0000 | undef | 0.0000 |
| Prostate | 0.0087 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0118 | | | |
| White blood cells | 0.0043 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0028 | Ovary_n | 0.0000 |
| Brain | 0.0000 | Ovary_t | 0.0051 |
| Hematopoietic | 0.0000 | Endocrine tissue | 0.0000 |
| Skin | 0.0000 | Fetal | 0.0012 |
| Hepatic | 0.0000 | Gastrointestinal | 0.0000 |
| Heart-blood vessels | 0.0071 | Hematopoietic | 0.0228 |
| Lung | 0.0145 | Skin-muscle | 0.0000 |
| Suprarenal gland | 0.0000 | Testicles | 0.0154 |
| Kidney | 0.0000 | Lung | 0.0000 |
| Placenta | 0.0000 | Nerves | 0.0060 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 121

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0010 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 122

| | NORMAL | TUMOR | Ratios | |
|---|---|---|---|---|
| | % frequency | % frequency | N/T | T/N |
| Bladder | 0.0234 | 0.0230 | 1.0170 | 0.9833 |
| Breast | 0.0269 | 0.0207 | 1.2992 | 0.7697 |
| Small intestine | 0.0061 | 0.0662 | 0.0927 | 10.7893 |
| Ovary | 0.0150 | 0.0572 | 0.2616 | 3.8219 |
| Endocrine tissue | 0.0085 | 0.0100 | 0.8491 | 1.1778 |
| Gastrointestinal | 0.0134 | 0.0463 | 0.2899 | 3.4492 |
| Brain | 0.0015 | 0.0092 | 0.1600 | 6.2504 |
| Hematopoietic | 0.0094 | 0.0000 | undef | 0.0000 |
| Skin | 0.0551 | 0.0000 | undef | 0.0000 |
| Hepatic | 0.0143 | 0.0388 | 0.3676 | 2.7200 |
| Heart | 0.0085 | 0.0000 | undef | 0.0000 |
| Testicles | 0.0058 | 0.0117 | 0.4920 | 2.0326 |
| Lung | 0.0073 | 0.0286 | 0.2540 | 3.9367 |
| Stomach-esophagus | 0.0966 | 0.0077 | 12.6053 | 0.0793 |
| Muscle-skeleton | 0.0000 | 0.0060 | 0.0000 | undef |
| Kidney | 0.0054 | 0.0068 | 0.7930 | 1.2610 |
| Pancreas | 0.0050 | 0.0055 | 0.8974 | 1.1143 |
| Penis | 0.0329 | 0.1600 | 0.2059 | 4.8565 |
| Prostate | 0.0087 | 0.0043 | 2.0473 | 0.4885 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0128 | | | |
| Prostate hyperplasia | 0.0148 | | | |
| Seminal vesicle | 0.0178 | | | |
| Sensory organs | 0.0000 | | | |
| White blood cells | 0.0017 | | | |
| Cervix | 0.0532 | | | |

| | FETUS % frequency | STANDARDIZED/SUB-TRACTED LIBRARIES % frequency | |
|---|---|---|---|
| Development | 0.0417 | Breast | 0.0136 |
| Gastrointestinal | 0.0056 | Ovary_n | 0.0000 |
| Brain | 0.0000 | Ovary_t | 0.0101 |

-continued

| | | | | |
|---|---|---|---|---|
| Hematopoietic | 0.0000 | Endocrine tissue | 0.0000 | |
| Skin | 0.0000 | Fetal | 0.0146 | |
| Hepatic | 0.0000 | Gastrointestinal | 0.0366 | |
| Heart-blood vessels | 0.0071 | Hematopoietic | 0.0000 | |
| Lung | 0.0036 | Skin-muscle | 0.0032 | |
| Suprarenal gland | 0.0000 | Testicles | 0.0000 | |
| Kidney | 0.0062 | Lung | 0.0573 | |
| Placenta | 0.0121 | Nerves | 0.0040 | |
| Prostate | 0.0249 | Prostate | 0.0205 | |
| Sensory organs | 0.0000 | Sensory Organs | 0.0077 | |
| | | Uterus_n | 0.0000 | |

Electronic Northern for SEQ. ID NO.: 123

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0019 | 0.0046 | 0.4142 | 2.4145 |
| Brain | 0.0007 | 0.0031 | 0.2400 | 4.1669 |
| Hematopoietic | 0.0027 | 0.0000 | undef | 0.0000 |
| Skin | 0.0073 | 0.0000 | undef | 0.0000 |
| Hepatic | 0.0000 | 0.0065 | 0.0000 | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1583 | 0.0000 | undef |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0030 | | | |
| Seminal vesicle | 0.0089 | | | |
| Sensory organs | 0.0000 | | | |
| White blood cells | 0.0000 | | | |
| Cervix | 0.0000 | | | |

| | FETUS | STANDARDIZED/SUB- TRACTED LIBRARIES | | |
|---|---|---|---|---|
| | % frequency | % frequency | | |
| Development | 0.0000 | Breast | 0.0000 | |
| Gastrointestinal | 0.0000 | Ovary_n | 0.0000 | |
| Brain | 0.0000 | Ovary_t | 0.0000 | |
| Hematopoietic | 0.0000 | Endocrine tissue | 0.0000 | |
| Skin | 0.0000 | Fetal | 0.0000 | |
| Hepatic | 0.0000 | Gastrointestinal | 0.0000 | |
| Heart-blood vessels | 0.0000 | Hematopoietic | 0.0000 | |
| Lung | 0.0036 | Skin-muscle | 0.0000 | |
| Suprarenal gland | 0.0000 | Testicles | 0.0000 | |
| Kidney | 0.0000 | Lung | 0.0000 | |
| Placenta | 0.0000 | Nerves | 0.0000 | |
| Prostate | 0.0000 | Prostate | 0.0000 | |
| Sensory organs | 0.0000 | Sensory Organs | 0.0000 | |
| | | Uterus_n | 0.0000 | |

Electronic Northern for SEQ. ID NO.: 124

| | NORMAL | TUMOR | Ratios | |
|---|---|---|---|---|
| | % frequency | % frequency | N/T | T/N |
| Bladder | 0.0000 | 0.0051 | 0.0000 | undef |
| Breast | 0.0000 | 0.0000 | undef | undef |
| Small intestine | 0.0000 | 0.0165 | 0.0000 | undef |
| Ovary | 0.0000 | 0.0026 | 0.0000 | undef |
| Endocrine tissue | 0.0051 | 0.0000 | undef | 0.0000 |
| Gastrointestinal | 0.0096 | 0.0000 | undef | 0.0000 |
| Brain | 0.0037 | 0.0010 | 3.5998 | 0.2778 |
| Hematopoietic | 0.0000 | 0.0000 | undef | undef |
| Skin | 0.0073 | 0.0000 | undef | 0.0000 |
| Hepatic | 0.0095 | 0.0065 | 1.4706 | 0.6800 |
| Heart | 0.0000 | 0.0000 | undef | 0.0000 |
| Testicles | 0.0095 | 0.0000 | undef | undef |
| Lung | 0.0021 | 0.0020 | 1.0161 | 0.9842 |
| Stomach-esophagus | 0.0000 | 0.0000 | undef | undef |
| Muscle-skeleton | 0.0017 | 0.0060 | 0.2856 | 3.5020 |
| Kidney | 0.0027 | 0.0068 | 0.3965 | 2.5219 |
| Pancreas | 0.0017 | 0.0110 | 0.1496 | 6.6857 |
| Penis | 0.0000 | 0.0000 | undef | undef |
| Prostate | 0.0065 | 0.0000 | undef | 0.0000 |
| Uterus-endometrium | 0.0068 | 0.1055 | 0.0640 | 15.6211 |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS | STANDARDIZED/SUB- TRACTED LIBRARIES | | |
|---|---|---|---|---|
| | % frequency | % frequency | | |
| Development | 0.0000 | Breast | 0.0000 | |
| Gastrointestinal | 0.0028 | Ovary_n | 0.0000 | |
| Brain | 0.0063 | Ovary_t | 0.0000 | |
| Hematopoietic | 0.0000 | Endocrine tissue | 0.0245 | |
| Skin | 0.0000 | Fetal | 0.0082 | |
| Hepatic | 0.0000 | Gastrointestinal | 0.0122 | |
| Heart-blood vessels | 0.0036 | Hematopoietic | 0.0000 | |
| Lung | 0.0036 | Skin-muscle | 0.0032 | |
| Suprarenal gland | 0.0000 | Testicles | 0.0000 | |
| Kidney | 0.0062 | Lung | 0.0246 | |
| Placenta | 0.0000 | Nerves | 0.0100 | |
| Prostate | 0.0000 | Prostate | 0.0000 | |
| Sensory organs | 0.0126 | Sensory Organs | 0.0077 | |
| | | Uterus_n | 0.0042 | |

Electronic Northern for SEQ. ID NO.: 125

| | NORMAL | TUMOR | Ratios | |
|---|---|---|---|---|
| | % frequency | % frequency | N/T | T/N |
| Bladder | 0.0195 | 0.0077 | 2.5424 | 0.3933 |
| Breast | 0.0064 | 0.0075 | 0.8507 | 1.1756 |
| Small intestine | 0.0061 | 0.0000 | undef | 0.0000 |
| Ovary | 0.0000 | 0.0130 | 0.0000 | undef |
| Endocrine tissue | 0.0153 | 0.0226 | 0.6792 | 1.4722 |
| Gastrointestinal | 0.0077 | 0.0093 | 0.8283 | 1.2072 |
| Brain | 0.0081 | 0.0092 | 0.8800 | 1.1364 |
| Hematopoietic | 0.0067 | 0.0379 | 0.1764 | 5.6676 |
| Skin | 0.0110 | 0.0000 | undef | 0.0000 |
| Hepatic | 0.0048 | 0.0194 | 0.2451 | 4.0800 |
| Heart | 0.0106 | 0.0000 | undef | 0.0000 |
| Testicles | 0.0000 | 0.0000 | undef | undef |
| Lung | 0.0083 | 0.0102 | 0.8129 | 1.2302 |
| Stomach-esophagus | 0.0000 | 0.0153 | 0.0000 | undef |
| Muscle-skeleton | 0.0103 | 0.0180 | 0.5711 | 1.7510 |
| Kidney | 0.0081 | 0.0068 | 1.1896 | 0.8406 |
| Pancreas | 0.0033 | 0.0000 | undef | 0.0000 |
| Penis | 0.0329 | 0.0000 | undef | 0.0000 |
| Prostate | 0.0153 | 0.0064 | 2.3885 | 0.4187 |
| Uterus-endometrium | 0.0135 | 0.1055 | 0.1280 | 7.8106 |
| Uterus-myometrium | 0.0305 | 0.0136 | 2.2445 | 0.4455 |
| Uterus-general | 0.0051 | 0.0000 | undef | 0.0000 |
| Breast hyperplasia | 0.0064 | | | |
| Prostate hyperplasia | 0.0059 | | | |
| Seminal vesicle | 0.0000 | | | |
| Sensory organs | 0.0118 | | | |
| White blood cells | 0.0069 | | | |
| Cervix | 0.0106 | | | |

-continued

|  | FETUS % frequency | STANDARDIZED/SUB- TRACTED LIBRARIES % frequency |  |
|---|---|---|---|
| Development | 0.0139 | Breast | 0.0136 |
| Gastrointestinal | 0.0056 | Ovary_n | 0.0000 |
| Brain | 0.0000 | Ovary_t | 0.0203 |
| Hematopoietic | 0.0157 | Endocrine tissue | 0.0245 |
| Skin | 0.0000 | Fetal | 0.0099 |
| Hepatic | 0.0000 | Gastrointestinal | 0.0122 |
| Heart-blood vessels | 0.0036 | Hematopoietic | 0.0171 |
| Lung | 0.0000 | Skin-muscle | 0.0097 |
| Suprarenal gland | 0.0000 | Testicles | 0.0000 |
| Kidney | 0.0000 | Lung | 0.0246 |
| Placenta | 0.0121 | Nerves | 0.0060 |
| Prostate | 0.0249 | Prostate | 0.0342 |
| Sensory organs | 0.0000 | Sensory Organs | 0.0387 |
|  |  | Uterus_n | 0.0250 |

Electronic Northern for SEQ. ID NO.: 126

|  | NORMAL % frequency | TUMOR % frequency | Ratios N/T | T/N |
|---|---|---|---|---|
| Bladder | 0.0039 | 0.0000 | undef | 0.0000 |
| Breast | 0.0013 | 0.0019 | 0.6805 | 1.4694 |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0010 | 0.0000 | undef |
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 |  |  |  |
| Prostate hyperplasia | 0.0000 |  |  |  |
| Seminal vesicle | 0.0000 |  |  |  |
| Sensory organs | 0.0000 |  |  |  |
| White blood cells | 0.0000 |  |  |  |
| Cervix | 0.0000 |  |  |  |

|  | FETUS % frequency | STANDARDIZED/SUB- TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0032 |
| Suprarenal gland | 0.0000 | Testicles | 0.0000 |
| Kidney | 0.0000 | Lung | 0.0000 |
| Placenta | 0.0000 | Nerves | 0.0010 |
| Prostate | 0.0000 | Prostate | 0.0000 |
| Sensory organs | 0.0000 | Sensory Organs | 0.0000 |
|  |  | Uterus_n | 0.0000 |

Electronic Northern for SEQ. ID NO.: 127

|  | NORMAL % frequency | TUMOR % frequency | Ratios N/T | T/N |
|---|---|---|---|---|
| Bladder | 0.0312 | 0.0486 | 0.6423 | 1.5569 |
| Breast | 0.0192 | 0.0282 | 0.6805 | 1.4694 |
| Small intestine | 0.0399 | 0.0000 | undef | 0.0000 |
| Ovary | 0.0210 | 0.0364 | 0.5756 | 1.7372 |
| Endocrine tissue | 0.0290 | 0.0326 | 0.8882 | 1.1258 |
| Gastrointestinal | 0.0460 | 0.0231 | 1.9880 | 0.5030 |
| Brain | 0.0532 | 0.0575 | 0.9257 | 1.0803 |
| Hematopoietic | 0.0348 | 0.0379 | 0.9175 | 1.0899 |
| Skin | 0.0367 | 0.0000 | undef | 0.0000 |
| Hepatic | 0.0048 | 0.0647 | 0.0735 | 13.5999 |
| Heart | 0.0699 | 0.0412 | 1.6961 | 0.5896 |
| Testicles | 0.0288 | 0.4210 | 0.0683 | 14.6349 |
| Lung | 0.0343 | 0.0368 | 0.9314 | 1.0737 |
| Stomach-esophagus | 0.0773 | 0.0230 | 3.3614 | 0.2975 |
| Muscle-skeleton | 0.0497 | 0.0660 | 0.7528 | 1.3283 |
| Kidney | 0.0353 | 0.1575 | 0.2241 | 4.4619 |
| Pancreas | 0.0165 | 0.0939 | 0.1760 | 5.6828 |
| Penis | 0.0299 | 0.0267 | 1.1232 | 0.8903 |
| Prostate | 0.0196 | 0.0298 | 0.6580 | 1.5197 |
| Uterus-endometrium | 0.0270 | 0.1583 | 0.1707 | 5.8579 |
| Uterus-myometrium | 0.0229 | 0.0679 | 0.3367 | 2.9702 |
| Uterus-general | 0.0051 | 0.0954 | 0.0534 | 18.7357 |
| Breast hyperplasia | 0.0192 |  |  |  |
| Prostate hyperplasia | 0.0505 |  |  |  |
| Seminal vesicle | 0.0890 |  |  |  |
| Sensory organs | 0.0353 |  |  |  |
| White blood cells | 0.0399 |  |  |  |
| Cervix | 0.0319 |  |  |  |

|  | FETUS % frequency | STANDARDIZED/SUB- TRACTED LIBRARIES % frequency |  |
|---|---|---|---|
| Development | 0.0417 | Breast | 0.0000 |
| Gastrointestinal | 0.0333 | Ovary_n | 0.0000 |
| Brain | 0.0313 | Ovary_t | 0.0152 |
| Hematopoietic | 0.0197 | Endocrine tissue | 0.0000 |
| Skin | 0.0000 | Fetal | 0.0082 |
| Hepatic | 0.0000 | Gastrointestinal | 0.0244 |
| Heart-blood vessels | 0.0783 | Hematopoietic | 0.0057 |
| Lung | 0.0217 | Skin-muscle | 0.0032 |
| Suprarenal gland | 0.0507 | Testicles | 0.0077 |
| Kidney | 0.0309 | Lung | 0.0082 |
| Placenta | 0.0727 | Nerves | 0.0141 |
| Prostate | 0.0997 | Prostate | 0.0000 |
| Sensory organs | 0.0000 | Sensory Organs | 0.0310 |
|  |  | Uterus_n | 0.0125 |

Electronic Northern for SEQ. ID NO.: 128

|  | NORMAL % frequency | TUMOR % frequency | Ratios N/T | T/N |
|---|---|---|---|---|
| Bladder | 0.0039 | 0.0077 | 0.5085 | 1.9666 |
| Breast | 0.0038 | 0.0000 | undef | 0.0000 |
| Small intestine | 0.0031 | 0.0000 | undef | 0.0000 |
| Ovary | 0.0030 | 0.0000 | undef | 0.0000 |
| Endocrine tissue | 0.0068 | 0.0025 | 2.7170 | 0.3681 |
| Gastrointestinal | 0.0019 | 0.0046 | 0.4142 | 2.4145 |
| Brain | 0.0007 | 0.0031 | 0.2400 | 4.1669 |
| Hematopoietic | 0.0013 | 0.0000 | undef | 0.0000 |
| Skin | 0.0000 | 0.0000 | undef | undef |
| Hepatic | 0.0000 | 0.0065 | 0.0000 | undef |
| Heart | 0.0074 | 0.0000 | undef | 0.0000 |
| Testicles | 0.0173 | 0.0117 | 1.4759 | 0.6775 |
| Lung | 0.0021 | 0.0000 | undef | 0.0000 |
| Stomach-esophagus | 0.0000 | 0.0000 | undef | undef |
| Muscle-skeleton | 0.0086 | 0.0000 | undef | 0.0000 |
| Kidney | 0.0081 | 0.0000 | undef | 0.0000 |
| Pancreas | 0.0033 | 0.0000 | undef | 0.0000 |
| Penis | 0.0030 | 0.0000 | undef | 0.0000 |
| Prostate | 0.0022 | 0.0043 | 0.5118 | 1.9538 |

|  | -continued | | |
|---|---|---|---|
| Uterus-endometrium | 0.0135 | 0.1055 | 0.1280 | 7.8106 |
| Uterus-myometrium | 0.0000 | 0.0000 | undef | undef |
| Uterus-general | 0.0051 | 0.0000 | undef | 0.0000 |
| Breast hyperplasia | 0.0000 | | | |
| Prostate hyperplasia | 0.0030 | | | |
| Seminal vesicle | 0.0089 | | | |
| Sensory organs | 0.0325 | | | |
| White blood cells | 0.0026 | | | |
| Cervix | 0.0000 | | | |

|  | FETUS % frequency | STANDARDIZED/SUB-TRACTED LIBRARIES % frequency |  |
|---|---|---|---|
| Development | 0.0139 | Breast | 0.0204 |
| Gastrointestinal | 0.0056 | Ovary_n | 0.0000 |
| Brain | 0.0063 | Ovary_t | 0.0152 |
| Hematopoietic | 0.0079 | Endocrine tissue | 0.0000 |
| Skin | 0.0000 | Fetal | 0.0082 |
| Hepatic | 0.0000 | Gastrointestinal | 0.0122 |
| Heart-blood vessels | 0.0000 | Hematopoietic | 0.0057 |
| Lung | 0.0036 | Skin-muscle | 0.0032 |
| Suprarenal gland | 0.0000 | Testicles | 0.0154 |
| Kidney | 0.0000 | Lung | 0.0164 |
| Placenta | 0.0061 | Nerves | 0.0060 |
| Prostate | 0.0000 | Prostate | 0.0205 |
| Sensory organs | 0.0000 | Sensory Organs | 0.0077 |
|  |  | Uterus_n | 0.0042 |

Electronic Northern for SEQ. ID NO.: 129

|  | NORMAL | TUMOR | Ratios | |
|---|---|---|---|---|
|  | % frequency | % frequency | N/T | T/N |
| Bladder | 0.0000 | 0.0000 | undef | undef |
| Breast | 0.0000 | 0.0019 | 0.0000 | undef |
| Small intestine | 0.0000 | 0.0000 | undef | undef |
| Ovary | 0.0000 | 0.0000 | undef | undef |
| Endocrine tissue | 0.0017 | 0.0000 | undef | 0.0000 |
| Gastrointestinal | 0.0000 | 0.0000 | undef | undef |
| Brain | 0.0007 | 0.0000 | undef | 0.0000 |
| Hematopoietic | 0.0000 | 0.0000 | undef | undef |
| Skin | 0.0037 | 0.0000 | undef | 0.0000 |
| Hepatic | 0.0000 | 0.0000 | undef | undef |
| Heart | 0.0021 | 0.0000 | undef | 0.0000 |
| Testicles | 0.0000 | 0.0000 | undef | undef |
| Lung | 0.0010 | 0.0000 | undef | 0.0000 |
| Stomach-esophagus | 0.0000 | 0.0000 | undef | undef |
| Muscle-skeleton | 0.0000 | 0.0000 | undef | undef |
| Kidney | 0.0027 | 0.0137 | 0.1983 | 5.0439 |
| Pancreas | 0.0017 | 0.0000 | undef | 0.0000 |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0009 | | | |
| Cervix | 0.0000 | | | |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0028 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0036 | Skin-muscle | 0.0000 |
| Suprarenal gland | 0.0254 | Testicles | 0.0077 |
| Kidney | 0.0000 | Lung | 0.0000 |
| Placenta | 0.0000 | Nerves | 0.0010 |
| Prostate | 0.0000 | Prostate | 0.0068 |
| Sensory organs | 0.0000 | Sensory Organs | 0.0000 |
|  |  | Uterus_n | 0.0000 |

Electronic Northern for SEQ. ID NO.: 130

|  | NORMAL | TUMOR | Ratios | |
|---|---|---|---|---|
|  | % frequency | % frequency | N/T | T/N |
| Bladder | 0.0039 | 0.0051 | 0.7627 | 1.3111 |
| Breast | 0.0013 | 0.0019 | 0.6805 | 1.4694 |
| Small intestine | 0.0031 | 0.0000 | undef | 0.0000 |
| Ovary | 0.0000 | 0.0000 | undef | undef |
| Endocrine tissue | 0.0000 | 0.0025 | undef | undef |
| Gastrointestinal | 0.0000 | 0.0046 | 0.0000 | undef |
| Brain | 0.0000 | 0.0010 | 0.0000 | undef |
| Hematopoietic | 0.0027 | 0.0000 | undef | 0.0000 |
| Skin | 0.0000 | 0.0000 | undef | undef |
| Hepatic | 0.0000 | 0.0000 | undef | undef |
| Heart | 0.0021 | 0.0000 | undef | 0.0000 |
| Testicles | 0.0000 | 0.0000 | undef | undef |
| Lung | 0.0010 | 0.0041 | 0.2540 | 3.9367 |
| Stomach-esophagus | 0.0000 | 0.0000 | undef | undef |
| Muscle-skeleton | 0.0017 | 0.0000 | undef | 0.0000 |
| Kidney | 0.0000 | 0.0068 | 0.0000 | undef |
| Pancreas | 0.0000 | 0.0000 | undef | undef |
| Penis | 0.0000 | 0.0000 | undef | undef |
| Prostate | 0.0000 | 0.0021 | 0.0000 | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0059 | | | |
| Sensory organs | 0.0000 | | | |
| White blood cells | 0.0009 | | | |
| Cervix | 0.0000 | | | |

|  | FETUS % frequency | STANDARDIZED/SUB-TRACTED LIBRARIES % frequency |  |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0000 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0082 |
| Placenta | 0.0000 | Nerves | 0.0000 |
| Prostate | 0.0000 | Prostate | 0.0068 |
| Sensory organs | 0.0000 | Sensory Organs | 0.0000 |
|  |  | Uterus_n | 0.0000 |

Electronic Northern for SEQ. ID NO.: 131

|  | NORMAL | TUMOR | Ratios | |
|---|---|---|---|---|
|  | % frequency | % frequency | N/T | T/N |
| Bladder | 0.0078 | 0.0128 | 0.6102 | 1.6389 |
| Breast | 0.0115 | 0.0169 | 0.6805 | 1.4694 |
| Small intestine | 0.0000 | 0.0165 | 0.0000 | undef |
| Ovary | 0.0060 | 0.0260 | 0.2303 | 4.3431 |
| Endocrine tissue | 0.0153 | 0.0176 | 0.8733 | 1.1451 |
| Gastrointestinal | 0.0019 | 0.0046 | 0.4142 | 2.4145 |
| Brain | 0.0074 | 0.0092 | 0.8000 | 1.2501 |
| Hematopoietic | 0.0080 | 0.0758 | 0.1059 | 9.4460 |
| Skin | 0.0037 | 0.0000 | undef | 0.0000 |
| Hepatic | 0.0095 | 0.0065 | 1.4706 | 0.6800 |
| Heart | 0.0201 | 0.0000 | undef | 0.0000 |
| Testicles | 0.0058 | 0.0234 | 0.2460 | 4.0652 |
| Lung | 0.0114 | 0.0164 | 0.6985 | 1.4315 |
| Stomach-esophagus | 0.0193 | 0.0077 | 2.5211 | 0.3967 |
| Muscle-skeleton | 0.0051 | 0.0120 | 0.4283 | 2.3347 |

| | | | |
|---|---|---|---|
| Kidney | 0.0136 | 0.0137 | 0.9913 | 1.0088 |
| Pancreas | 0.0066 | 0.0110 | 0.5983 | 1.6714 |
| Penis | 0.0030 | 0.0000 | undef | 0.0000 |
| Prostate | 0.0065 | 0.0128 | 0.5118 | 1.9538 |
| Uterus-endometrium | 0.0068 | 0.1055 | 0.0640 | 15.6211 |
| Uterus-myometrium | 0.0076 | 0.0000 | undef | 0.0000 |
| Uterus-general | 0.0051 | 0.0000 | undef | 0.0000 |
| Breast hyperplasia | 0.0096 | | | |
| Prostate hyperplasia | 0.0089 | | | |
| Seminal vesicle | 0.0089 | | | |
| Sensory organs | 0.0118 | | | |
| White blood cells | 0.0009 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0204 |
| Gastrointestinal | 0.0000 | Ovary_n | 0.0000 |
| Brain | 0.0000 | Ovary_t | 0.0051 |
| Hematopoietic | 0.0079 | Endocrine tissue | 0.0000 |
| Skin | 0.0000 | Fetal | 0.0099 |
| Hepatic | 0.0260 | Gastrointestinal | 0.0244 |
| Heart-blood vessels | 0.0107 | Hematopoietic | 0.0057 |
| Lung | 0.0108 | Skin-muscle | 0.0259 |
| Suprarenal gland | 0.0000 | Testicles | 0.0077 |
| Kidney | 0.0062 | Lung | 0.0082 |
| Placenta | 0.0424 | Nerves | 0.0090 |
| Prostate | 0.0000 | Prostate | 0.0000 |
| Sensory organs | 0.0000 | Sensory Organs | 0.0000 |
| | | Uterus_n | 0.0167 |

Electronic Northern for SEQ. ID NO.: 132

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0000 | 0.0000 | undef | undef |
| Small intestine | 0.0000 | 0.0000 | undef | undef |
| Ovary | 0.0000 | 0.0000 | undef | undef |
| Endocrine tissue | 0.0000 | 0.0025 | 0.0000 | undef |
| Gastrointestinal | 0.0000 | 0.0000 | undef | undef |
| Brain | 0.0000 | 0.0000 | undef | undef |
| Hematopoietic | 0.0013 | 0.0000 | undef | 0.0000 |
| Skin | 0.0000 | 0.0000 | undef | undef |
| Hepatic | 0.0000 | 0.0000 | undef | undef |
| Heart | 0.0011 | 0.0000 | undef | 0.0000 |
| Testicles | 0.0058 | 0.0000 | undef | 0.0000 |
| Lung | 0.0000 | 0.0000 | undef | undef |
| Stomach-esophagus | 0.0000 | 0.0000 | undef | undef |
| Muscle-skeleton | 0.0000 | 0.0000 | undef | undef |
| Kidney | 0.0000 | 0.0000 | undef | undef |
| Pancreas | 0.0017 | 0.0000 | undef | 0.0000 |
| Penis | 0.0000 | 0.0000 | undef | undef |
| Prostate | 0.0022 | 0.0000 | undef | 0.0000 |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0000 |
| Gastrointestinal | 0.0000 | Ovary_n | 0.0000 |
| Brain | 0.0000 | Ovary_t | 0.0051 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0057 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0061 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 133

| | NORMAL | TUMOR | Ratios | |
|---|---|---|---|---|
| | % frequency | % frequency | N/T | T/N |
| Bladder | 0.0039 | 0.0051 | 0.7627 | 1.3111 |
| Breast | 0.0141 | 0.0150 | 0.9357 | 1.0687 |
| Small intestine | 0.0184 | 0.0000 | undef | 0.0000 |
| Ovary | 0.0120 | 0.0104 | 1.1513 | 0.8686 |
| Endocrine tissue | 0.0102 | 0.0176 | 0.5822 | 1.7176 |
| Gastrointestinal | 0.0057 | 0.0139 | 0.4142 | 2.4145 |
| Brain | 0.0052 | 0.0072 | 0.7200 | 1.3890 |
| Hematopoietic | 0.0174 | 0.0000 | undef | 0.0000 |
| Skin | 0.0110 | 0.0000 | undef | 0.0000 |
| Hepatic | 0.0000 | 0.0000 | undef | undef |
| Heart | 0.0064 | 0.0000 | undef | 0.0000 |
| Testicles | 0.0058 | 0.0234 | 0.2460 | 4.0652 |
| Lung | 0.0104 | 0.0204 | 0.5080 | 1.9684 |
| Stomach-esophagus | 0.0193 | 0.0153 | 1.2605 | 0.7933 |
| Muscle-skeleton | 0.0086 | 0.0240 | 0.3569 | 2.8016 |
| Kidney | 0.0244 | 0.0000 | undef | 0.0000 |
| Pancreas | 0.0066 | 0.0110 | 0.5983 | 1.6714 |
| Penis | 0.0120 | 0.0267 | 0.4493 | 2.2259 |
| Prostate | 0.0153 | 0.0149 | 1.0236 | 0.9769 |
| Uterus-endometrium | 0.0270 | 0.2111 | 0.1280 | 7.8106 |
| Uterus-myometrium | 0.0305 | 0.0136 | 2.2445 | 0.4455 |
| Uterus-general | 0.0153 | 0.0000 | undef | 0.0000 |
| Breast hyperplasia | 0.0192 | | | |
| Prostate hyperplasia | 0.0327 | | | |
| Seminal vesicle | 0.0178 | | | |
| Sensory organs | 0.0235 | | | |
| White blood cells | 0.0000 | | | |
| Cervix | 0.0319 | | | |

| | FETUS % frequency | STANDARDIZED/SUB-TRACTED LIBRARIES % frequency | |
|---|---|---|---|
| Development | 0.0000 | Breast | 0.0068 |
| Gastrointestinal | 0.0305 | Ovary_n | 0.0000 |
| Brain | 0.0313 | Ovary_t | 0.0253 |
| Hematopoietic | 0.0039 | Endocrine tissue | 0.0245 |
| Skin | 0.0000 | Fetal | 0.0093 |
| Hepatic | 0.0520 | Gastrointestinal | 0.0122 |
| Heart-blood vessels | 0.0107 | Hematopoietic | 0.0000 |
| Lung | 0.0253 | Skin-muscle | 0.0000 |
| Suprarenal gland | 0.0000 | Testicles | 0.0000 |
| Kidney | 0.0309 | Lung | 0.0246 |
| Placenta | 0.0061 | Nerves | 0.0020 |
| Prostate | 0.0000 | Prostate | 0.0068 |
| Sensory organs | 0.0000 | Sensory Organs | 0.0000 |
| | | Uterus_n | 0.0042 |

Electronic Northern for SEQ. ID NO.: 134

| | NORMAL | TUMOR | Ratios | |
|---|---|---|---|---|
| | % frequency | % frequency | N/T | T/N |
| Bladder | 0.0273 | 0.0383 | 0.7119 | 1.4047 |
| Breast | 0.0141 | 0.0244 | 0.5758 | 1.7366 |
| Small intestine | 0.0245 | 0.0331 | 0.7415 | 1.3487 |
| Ovary | 0.0120 | 0.0312 | 0.3838 | 2.6058 |
| Endocrine tissue | 0.0290 | 0.0201 | 1.4434 | 0.6928 |
| Gastrointestinal | 0.0287 | 0.0278 | 1.0354 | 0.9658 |
| Brain | 0.0133 | 0.0298 | 0.4469 | 2.2378 |
| Hematopoietic | 0.0281 | 0.0379 | 0.7411 | 1.3494 |
| Skin | 0.0073 | 0.0847 | 0.0866 | 11.5419 |
| Hepatic | 0.0381 | 0.0259 | 1.4706 | 0.6800 |
| Heart | 0.0191 | 0.1512 | 0.1262 | 7.9265 |

| | NORMAL | TUMOR | | |
|---|---|---|---|---|
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0061 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

-continued

| | | | |
|---|---|---|---|
| Testicles | 0.0173 | 0.0702 | 0.2460 | 4.0652 |
| Lung | 0.0447 | 0.0470 | 0.9498 | 1.0528 |
| Stomach-esophagus | 0.0773 | 0.0153 | 5.0421 | 0.1983 |
| Muscle-skeleton | 0.0668 | 0.0420 | 1.5909 | 0.6286 |
| Kidney | 0.0190 | 0.0342 | 0.0551 | 1.8014 |
| Pancreas | 0.0066 | 0.0331 | 0.1994 | 5.0142 |
| Penis | 0.0150 | 0.1600 | 0.0936 | 10.6842 |
| Prostate | 0.0196 | 0.0149 | 1.3161 | 0.7598 |
| Uterus-endometrium | 0.0068 | 0.1055 | 0.0640 | 15.6211 |
| Uterus-myometrium | 0.0229 | 0.0204 | 1.1223 | 0.8911 |
| Uterus-general | 0.0102 | 0.0000 | undef | 0.0000 |
| Breast hyperplasia | 0.0000 | | | |
| Prostate hyperplasia | 0.0030 | | | |
| Seminal vesicle | 0.0089 | | | |
| Sensory organs | 0.0000 | | | |
| White blood cells | 0.1240 | | | |
| Cervix | 0.0213 | | | |

| | FETUS % frequency | STANDARDIZED/SUB-TRACTED LIBRARIES % frequency | |
|---|---|---|---|
| Development | 0.0000 | Breast | 0.0408 |
| Gastrointestinal | 0.0111 | Ovary_n | 0.0000 |
| Brain | 0.0000 | Ovary_t | 0.0253 |
| Hematopoietic | 0.0118 | Endocrine tissue | 0.0245 |
| Skin | 0.0000 | Fetal | 0.0169 |
| Hepatic | 0.0260 | Gastrointestinal | 0.0244 |
| Heart-blood vessels | 0.0107 | Hematopoietic | 0.0000 |
| Lung | 0.0036 | Skin-muscle | 0.0454 |
| Suprarenal gland | 0.0000 | Testicles | 0.0000 |
| Kidney | 0.0000 | Lung | 0.0164 |
| Placenta | 0.0364 | Nerves | 0.0000 |
| Prostate | 0.0000 | Prostate | 0.0000 |
| Sensory organs | 0.0126 | Sensory Organs | 0.0000 |
| | | Uterus_n | 0.0042 |

Electronic Northern for SEQ. ID NO.: 135

| | NORMAL | TUMOR | Ratios | |
|---|---|---|---|---|
| | % frequency | % frequency | N/T | T/N |
| Bladder | 0.0390 | 0.0383 | 1.0170 | 0.9833 |
| Breast | 0.0102 | 0.0301 | 0.3403 | 2.9389 |
| Small intestine | 0.0429 | 0.0000 | undef | 0.0000 |
| Ovary | 0.0030 | 0.0156 | 0.1919 | 5.2117 |
| Endocrine tissue | 0.0358 | 0.0351 | 1.0189 | 0.9815 |
| Gastrointestinal | 0.0115 | 0.0278 | 0.4142 | 2.4145 |
| Brain | 0.0148 | 0.0226 | 0.6545 | 1.5279 |
| Hematopoietic | 0.0227 | 0.2273 | 0.1000 | 10.0016 |
| Skin | 0.0367 | 0.1695 | 0.2166 | 4.6168 |
| Hepatic | 0.0285 | 0.0582 | 0.4902 | 2.0400 |
| Heart | 0.0445 | 0.0687 | 0.6476 | 1.5441 |
| Testicles | 0.0173 | 0.0234 | 0.7380 | 1.3551 |
| Lung | 0.0291 | 0.0470 | 0.6185 | 1.6169 |
| Stomach-esophagus | 0.0580 | 0.0153 | 3.7816 | 0.2644 |
| Muscle-skeleton | 0.0685 | 0.0840 | 0.8159 | 1.2257 |
| Kidney | 0.0244 | 0.0685 | 0.3569 | 2.8022 |
| Pancreas | 0.0116 | 0.0607 | 0.1904 | 5.2530 |
| Penis | 0.0180 | 0.0000 | undef | 0.0000 |
| Prostate | 0.0131 | 0.0064 | 2.0473 | 0.4885 |
| Uterus-endometrium | 0.0135 | 0.6332 | 0.0213 | 46.8633 |
| Uterus-myometrium | 0.0076 | 0.0408 | 0.1870 | 5.3463 |
| Uterus-general | 0.0051 | 0.0000 | undef | 0.0000 |
| Breast hyperplasia | 0.0128 | | | |
| Prostate hyperplasia | 0.0149 | | | |
| Seminal vesicle | 0.0000 | | | |
| Sensory organs | 0.0000 | | | |
| White blood cells | 0.0867 | | | |
| Cervix | 0.0639 | | | |

| | FETUS % frequency | STANDARDIZED/SUB-TRACTED LIBRARIES % frequency | |
|---|---|---|---|
| Development | 0.0000 | Breast | 0.0068 |
| Gastrointestinal | 0.0167 | Ovary_n | 0.0000 |
| Brain | 0.0000 | Ovary_t | 0.0051 |
| Hematopoietic | 0.0236 | Endocrine tissue | 0.0000 |
| Skin | 0.0000 | Fetal | 0.0035 |
| Hepatic | 0.0000 | Gastrointestinal | 0.0122 |
| Heart-blood vessels | 0.0000 | Hematopoietic | 0.0000 |
| Lung | 0.0000 | Skin-muscle | 0.0032 |
| Suprarenal gland | 0.0000 | Testicles | 0.0077 |
| Kidney | 0.0000 | Lung | 0.0000 |
| Placenta | 0.0182 | Nerves | 0.0030 |
| Prostate | 0.0997 | Prostate | 0.0000 |
| Sensory organs | 0.0000 | Sensory Organs | 0.0464 |
| | | Uterus_n | 0.0000 |

Electronic Northern for SEQ. ID NO.: 136

| | NORMAL | TUMOR | Ratios | |
|---|---|---|---|---|
| | % frequency | % frequency | N/T | T/N |
| Bladder | 0.0000 | 0.0026 | 0.0000 | undef |
| Breast | 0.0102 | 0.0038 | 2.7221 | 0.3674 |
| Small intestine | 0.0092 | 0.0165 | 0.5561 | 1.7982 |
| Ovary | 0.0090 | 0.0078 | 1.1513 | 0.8686 |
| Endocrine tissue | 0.0000 | 0.0150 | 0.0000 | undef |
| Gastrointestinal | 0.0019 | 0.0093 | 0.2071 | 4.8289 |
| Brain | 0.0059 | 0.0031 | 1.9199 | 0.5209 |
| Hematopoietic | 0.0040 | 0.0379 | 0.1059 | 9.4460 |
| Skin | 0.0073 | 0.0000 | undef | 0.0000 |
| Hepatic | 0.0048 | 0.0065 | 0.7353 | 1.3600 |
| Heart | 0.0000 | 0.0000 | undef | undef |
| Testicles | 0.0000 | 0.0117 | 0.0000 | undef |
| Lung | 0.0114 | 0.0041 | 2.7942 | 0.3579 |
| Stomach-esophagus | 0.0097 | 0.0153 | 0.6303 | 1.5866 |
| Muscle-skeleton | 0.0103 | 0.0120 | 0.8567 | 1.1673 |
| Kidney | 0.0081 | 0.0000 | undef | 0.0000 |
| Pancreas | 0.0050 | 0.0000 | undef | 0.0000 |
| Penis | 0.0060 | 0.0000 | undef | 0.0000 |
| Prostate | 0.0000 | 0.0064 | 0.0000 | undef |
| Uterus-endometrium | 0.0068 | 0.1055 | 0.0640 | 15.6211 |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0030 | | | |
| Seminal vesicle | 0.0000 | | | |
| Sensory organs | 0.0000 | | | |
| White blood cells | 0.0104 | | | |
| Cervix | 0.0000 | | | |

| | FETUS % frequency | STANDARDIZED/SUB-TRACTED LIBRARIES % frequency | |
|---|---|---|---|
| Development | 0.0139 | Breast | 0.0068 |
| Gastrointestinal | 0.0056 | Ovary_n | 0.0000 |
| Brain | 0.0000 | Ovary_t | 0.0000 |
| Hematopoietic | 0.0079 | Endocrine tissue | 0.0000 |
| Skin | 0.0000 | Fetal | 0.0076 |
| Hepatic | 0.0000 | Gastrointestinal | 0.0000 |
| Heart-blood vessels | 0.0142 | Hematopoietic | 0.0171 |
| Lung | 0.0108 | Skin-muscle | 0.0000 |
| Suprarenal gland | 0.0254 | Testicles | 0.0000 |
| Kidney | 0.0000 | Lung | 0.0164 |
| Placenta | 0.0061 | Nerves | 0.0060 |
| Prostate | 0.0000 | Prostate | 0.0068 |
| Sensory organs | 0.0126 | Sensory Organs | 0.0000 |
| | | Uterus_n | 0.0125 |

Electronic Northern for SEQ. ID NO.: 137

| | NORMAL | TUMOR | Ratios | |
|---|---|---|---|---|
| | % frequency | % frequency | N/T | T/N |
| Bladder | 0.0000 | 0.0000 | undef | undef |
| Breast | 0.0013 | 0.0000 | undef | 0.0000 |
| Small intestine | 0.0000 | 0.0000 | undef | undef |
| Ovary | 0.0000 | 0.0000 | undef | undef |
| Endocrine tissue | 0.0000 | 0.0000 | undef | undef |
| Gastrointestinal | 0.0000 | 0.0000 | undef | undef |
| Brain | 0.0000 | 0.0000 | undef | undef |

-continued

| | | | |
|---|---|---|---|
| Hematopoietic | 0.0000 | 0.0000 | undef | undef |
| Skin | 0.0000 | 0.0000 | undef | undef |
| Hepatic | 0.0000 | 0.0000 | undef | undef |
| Heart | 0.0000 | 0.0000 | undef | undef |
| Testicles | 0.0000 | 0.0000 | undef | undef |
| Lung | 0.0000 | 0.0000 | undef | undef |
| Stomach-esophagus | 0.0000 | 0.0000 | undef | undef |
| Muscle-skeleton | 0.0017 | 0.0000 | undef | 0.0000 |
| Kidney | 0.0000 | 0.0000 | undef | undef |
| Pancreas | 0.0000 | 0.0000 | undef | undef |
| Penis | 0.0000 | 0.0000 | undef | undef |
| Prostate | 0.0000 | 0.0000 | undef | undef |
| Uterus-endometrium | 0.0000 | 0.1055 | 0.0000 | undef |
| Uterus-myometrium | 0.0000 | 0.0000 | undef | undef |
| Uterus-general | 0.0000 | 0.0000 | undef | undef |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0000 | Ovary_n | 0.0000 |
| Brain | 0.0000 | Ovary_t | 0.0000 |
| Hematopoietic | 0.0000 | Endocrine tissue | 0.0000 |
| Skin | 0.0000 | Fetal | 0.0006 |
| Hepatic | 0.0000 | Gastrointestinal | 0.0000 |
| Heart-blood vessels | 0.0000 | Hematopoietic | 0.0000 |
| Lung | 0.0000 | Skin-muscle | 0.0000 |
| Suprarenal gland | 0.0000 | Testicles | 0.0000 |
| Kidney | 0.0000 | Lung | 0.0000 |
| Placenta | 0.0000 | Nerves | 0.0000 |
| Prostate | 0.0000 | Prostate | 0.0000 |
| Sensory organs | 0.0000 | Sensory Organs | 0.0000 |
| | | Uterus_n | 0.0000 |

Electronic Northern for SEQ. ID NO.: 138

| | NORMAL % frequency | TUMOR % frequency | Ratios N/T | Ratios T/N |
|---|---|---|---|---|
| Bladder | 0.0156 | 0.0051 | 3.0509 | 0.3278 |
| Breast | 0.0000 | 0.0038 | 0.0000 | undef |
| Small intestine | 0.0000 | 0.0331 | 0.0000 | undef |
| Ovary | 0.0000 | 0.0052 | 0.0000 | undef |
| Endocrine tissue | 0.0051 | 0.0050 | 1.0189 | 0.9815 |
| Gastrointestinal | 0.0077 | 0.0139 | 0.5522 | 1.8109 |
| Brain | 0.0059 | 0.0062 | 0.9599 | 1.0417 |
| Hematopoietic | 0.0040 | 0.0000 | undef | 0.0000 |
| Skin | 0.0000 | 0.0000 | undef | undef |
| Hepatic | 0.0048 | 0.0065 | 0.7353 | 1.3600 |
| Heart | 0.0085 | 0.0275 | 0.3084 | 3.2426 |
| Testicles | 0.0000 | 0.0234 | 0.0000 | undef |
| Lung | 0.0062 | 0.0143 | 0.4355 | 2.2964 |
| Stomach-esophagus | 0.0097 | 0.0000 | undef | 0.0000 |
| Muscle-skeleton | 0.0137 | 0.0000 | undef | 0.0000 |
| Kidney | 0.0000 | 0.0000 | undef | undef |
| Pancreas | 0.0033 | 0.0276 | 0.1197 | 8.3571 |
| Penis | 0.0120 | 0.0000 | undef | 0.0000 |
| Prostate | 0.0000 | 0.0064 | 0.0000 | undef |
| Uterus-endometrium | 0.0000 | 0.1055 | 0.0000 | undef |
| Uterus-myometrium | 0.0152 | 0.0068 | 2.2445 | 0.4455 |
| Uterus-general | 0.0051 | 0.0000 | undef | 0.0000 |
| Breast hyperplasia | 0.0064 | | | |
| Prostate hyperplasia | 0.0030 | | | |
| Seminal vesicle | 0.0000 | | | |
| Sensory organs | 0.0000 | | | |
| White blood cells | 0.0087 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0272 |
| Gastrointestinal | 0.0028 | Ovary_n | 0.0000 |
| Brain | 0.0000 | Ovary_t | 0.0253 |
| Hematopoietic | 0.0118 | Endocrine tissue | 0.0000 |
| Skin | 0.0000 | Fetal | 0.0151 |
| Hepatic | 0.0000 | Gastrointestinal | 0.0000 |
| Heart-blood vessels | 0.0107 | Hematopoietic | 0.0057 |
| Lung | 0.0108 | Skin-muscle | 0.0356 |
| Suprarenal gland | 0.0000 | Testicles | 0.0000 |
| Kidney | 0.0000 | Lung | 0.0000 |
| Placenta | 0.0242 | Nerves | 0.0090 |
| Prostate | 0.0249 | Prostate | 0.0068 |
| Sensory organs | 0.0000 | Sensory Organs | 0.0077 |
| | | Uterus_n | 0.0042 |

Electronic Northern for SEQ. ID NO.: 139

| | NORMAL % frequency | TUMOR % frequency | Ratios N/T | Ratios T/N |
|---|---|---|---|---|
| Bladder | 0.0000 | 0.0000 | undef | undef |
| Breast | 0.0013 | 0.0056 | 0.2268 | 4.4083 |
| Small intestine | 0.0061 | 0.0165 | 0.3707 | 2.6973 |
| Ovary | 0.0120 | 0.0052 | 2.3025 | 0.4343 |
| Endocrine tissue | 0.0017 | 0.0025 | 0.6792 | 1.4722 |
| Gastrointestinal | 0.0077 | 0.0046 | 1.6567 | 0.6036 |
| Brain | 0.0000 | 0.0021 | 0.0000 | undef |
| Hematopoietic | 0.0067 | 0.0000 | undef | 0.0000 |
| Skin | 0.0000 | 0.0000 | undef | undef |
| Hepatic | 0.0000 | 0.0000 | undef | undef |
| Heart | 0.0000 | 0.0275 | 0.0000 | undef |
| Testicles | 0.0000 | 0.0000 | undef | undef |
| Lung | 0.0000 | 0.0041 | 0.0000 | undef |
| Stomach-esophagus | 0.0000 | 0.0000 | undef | undef |
| Muscle-skeleton | 0.0017 | 0.0060 | 0.2856 | 3.5020 |
| Kidney | 0.0054 | 0.0000 | undef | 0.0000 |
| Pancreas | 0.0017 | 0.0000 | undef | 0.0000 |
| Penis | 0.0060 | 0.0000 | undef | 0.0000 |
| Prostate | 0.0044 | 0.0064 | 0.6824 | 1.4654 |
| Uterus-endometrium | 0.0000 | 0.1055 | 0.0000 | undef |
| Uterus-myometrium | 0.0076 | 0.0000 | undef | 0.0000 |
| Uterus-general | 0.0000 | 0.0000 | undef | undef |
| Breast hyperplasia | 0.0032 | | | |
| Prostate hyperplasia | 0.0030 | | | |
| Seminal vesicle | 0.0000 | | | |
| Sensory organs | 0.0235 | | | |
| White blood cells | 0.0000 | | | |
| Cervix | 0.0000 | | | |

| | FETUS % frequency | STANDARDIZED/SUB-TRACTED LIBRARIES % frequency | |
|---|---|---|---|
| Development | 0.0000 | Breast | 0.0000 |
| Gastrointestinal | 0.0056 | Ovary_n | 0.0000 |
| Brain | 0.0063 | Ovary_t | 0.0051 |
| Hematopoietic | 0.0000 | Endocrine tissue | 0.0245 |
| Skin | 0.0000 | Fetal | 0.0041 |
| Hepatic | 0.0000 | Gastrointestinal | 0.0244 |
| Heart-blood vessels | 0.0036 | Hematopoietic | 0.0000 |
| Lung | 0.0036 | Skin-muscle | 0.0032 |
| Suprarenal gland | 0.0000 | Testicles | 0.0000 |
| Kidney | 0.0000 | Lung | 0.0164 |
| Placenta | 0.0000 | Nerves | 0.0010 |
| Prostate | 0.0000 | Prostate | 0.0137 |
| Sensory organs | 0.0251 | Sensory Organs | 0.0000 |
| | | Uterus_n | 0.0000 |

-continued

Electronic Northern for SEQ. ID NO.: 140

| | NORMAL | TUMOR | Ratios | |
|---|---|---|---|---|
| | % frequency | % frequency | N/T | T/N |
| Bladder | 0.0039 | 0.0000 | undef | 0.0000 |
| Breast | 0.0051 | 0.0094 | 0.5444 | 1.8368 |
| Small intestine | 0.0000 | 0.0000 | undef | undef |
| Ovary | 0.0090 | 0.0000 | undef | 0.0000 |
| Endocrine tissue | 0.0085 | 0.0100 | 0.8491 | 1.1778 |
| Gastrointestinal | 0.0077 | 0.0000 | undef | 0.0000 |
| Brain | 0.0015 | 0.0041 | 0.3600 | 2.7779 |
| Hematopoietic | 0.0040 | 0.0000 | undef | 0.0000 |
| Skin | 0.0110 | 0.0000 | undef | 0.0000 |
| Hepatic | 0.0000 | 0.0000 | undef | undef |
| Heart | 0.0011 | 0.0137 | 0.0771 | 12.9706 |
| Testicles | 0.0058 | 0.0117 | 0.4920 | 2.0326 |
| Lung | 0.0042 | 0.0020 | 2.0321 | 0.4921 |
| Stomach-esophagus | 0.0000 | 0.0153 | 0.0000 | undef |
| Muscle-skeleton | 0.0034 | 0.0060 | 0.5711 | 1.7510 |
| Kidney | 0.0000 | 0.0000 | undef | undef |
| Pancreas | 0.0017 | 0.0110 | 0.1496 | 6.6857 |
| Penis | 0.0000 | 0.0000 | undef | undef |
| Prostate | 0.0044 | 0.0043 | 1.0236 | 0.9769 |
| Uterus-endometrium | 0.0000 | 0.1055 | 0.0000 | undef |
| Uterus-myometrium | 0.0000 | 0.0068 | 0.0000 | undef |
| Uterus-general | 0.0153 | 0.0000 | undef | 0.0000 |
| Breast hyperplasia | 0.0000 | | | |
| Prostate hyperplasia | 0.0030 | | | |
| Seminal vesicle | 0.0089 | | | |
| Sensory organs | 0.0118 | | | |
| White blood cells | 0.0026 | | | |
| Cervix | 0.0000 | | | |

| | FETUS % frequency | STANDARDIZED/SUB-TRACTED LIBRARIES % frequency |
|---|---|---|
| Development | 0.0000 | Breast 0.0204 |
| Gastrointestinal | 0.0056 | Ovary_n 0.0000 |
| Brain | 0.0063 | Ovary_t 0.0051 |
| Hematopoietic | 0.0000 | Endocrine tissue 0.0000 |
| Skin | 0.0000 | Fetal 0.0116 |
| Hepatic | 0.0000 | Gastrointestinal 0.0122 |
| Heart-blood vessels | 0.0000 | Hematopoietic 0.0000 |
| Lung | 0.0036 | Skin-muscle 0.0130 |
| Suprarenal gland | 0.0000 | Testicles 0.0000 |
| Kidney | 0.0062 | Lung 0.0164 |
| Placenta | 0.0061 | Nerves 0.0060 |
| Prostate | 0.0000 | Prostate 0.0000 |
| Sensory organs | 0.0000 | Sensory Organs 0.0000 |
| | | Uterus_n 0.0000 |

Electronic Northern for SEQ. ID NO.: 141

| | NORMAL | TUMOR | Ratios | |
|---|---|---|---|---|
| | % frequency | % frequency | N/T | T/N |
| Bladder | 0.0000 | 0.0051 | 0.0000 | undef |
| Breast | 0.0064 | 0.0150 | 0.4253 | 2.3511 |
| Small intestine | 0.0000 | 0.0496 | 0.0000 | undef |
| Ovary | 0.0060 | 0.0026 | 2.3025 | 0.4343 |
| Endocrine tissue | 0.0068 | 0.0050 | 1.3585 | 0.7361 |
| Gastrointestinal | 0.0096 | 0.0046 | 2.0708 | 0.4829 |
| Brain | 0.0052 | 0.0051 | 1.0079 | 0.9921 |
| Hematopoietic | 0.0040 | 0.0000 | undef | 0.0000 |
| Skin | 0.0037 | 0.0000 | undef | 0.0000 |
| Hepatic | 0.0000 | 0.0000 | undef | undef |
| Heart | 0.0053 | 0.0000 | undef | 0.0000 |
| Testicles | 0.0000 | 0.0000 | undef | undef |
| Lung | 0.0083 | 0.0061 | 1.3548 | 0.7381 |
| Stomach-esophagus | 0.0000 | 0.0153 | 0.0000 | undef |
| Muscle-skeleton | 0.0103 | 0.0000 | undef | 0.0000 |
| Kidney | 0.0027 | 0.0068 | 0.3965 | 2.5219 |
| Pancreas | 0.0033 | 0.0055 | 0.5983 | 1.6714 |
| Penis | 0.0120 | 0.0267 | 0.4493 | 2.2259 |
| Prostate | 0.0000 | 0.0021 | 0.0000 | undef |
| Uterus-endometrium | 0.0068 | 0.1055 | 0.0640 | 15.6211 |
| Uterus-myometrium | 0.0076 | 0.0000 | undef | 0.0000 |
| Uterus-general | 0.0153 | 0.0000 | undef | 0.0000 |
| Breast hyperplasia | 0.0000 | | | |
| Prostate hyperplasia | 0.0000 | | | |
| Seminal vesicle | 0.0000 | | | |
| Sensory organs | 0.0000 | | | |
| White blood cells | 0.0087 | | | |
| Cervix | 0.0000 | | | |

| | FETUS % frequency | STANDARDIZED/SUB-TRACTED LIBRARIES % frequency |
|---|---|---|
| Development | 0.0000 | Breast 0.0136 |
| Gastrointestinal | 0.0139 | Ovary_n 0.0000 |
| Brain | 0.0000 | Ovary_t 0.0101 |
| Hematopoietic | 0.0039 | Endocrine tissue 0.0000 |
| Skin | 0.0000 | Fetal 0.0082 |
| Hepatic | 0.0000 | Gastrointestinal 0.0000 |
| Heart-blood vessels | 0.0071 | Hematopoietic 0.0000 |
| Lung | 0.0000 | Skin-muscle 0.0032 |
| Suprarenal gland | 0.0000 | Testicles 0.0154 |
| Kidney | 0.0000 | Lung 0.0082 |
| Placenta | 0.0061 | Nerves 0.0040 |
| Prostate | 0.0000 | Prostate 0.0068 |
| Sensory organs | 0.0000 | Sensory Organs 0.0000 |
| | | Uterus_n 0.0000 |

2.2. Fisher Test

In order to decide whether a partial sequence S of a gene occurs significantly more often or less often in a library for normal tissue than in a library for degenerated tissue, Fisher's exact test, a standard statistical process, is carried out (Hays, W. L., (1991) Statistics, Harcourt Brace College Publishers, Fort Worth).

The null hypothesis reads: The two libraries cannot be distinguished with respect to the frequency of sequences homologous to S. If the null hypothesis can be rejected with high enough certainty, the gene belonging to S is accepted as an advantageous candidate for a cancer gene, and in the next step an attempt is made to achieve lengthening of its sequence.

EXAMPLE 3

Automatic Lengthening of the Partial Sequence

Automatic lengthening of partial sequence S is completed in three steps:
1. Determination of all sequences homologous to S from the total set of available sequences using BLAST
2. Assembling these sequences by means of the standard program GAP4 (Bonfield, J. K.; Smith, K. F. and Staden, R. (1995), Nucleic Acids Research 23 4992–4999) (contig formation).
3. Computation of a consensus sequence C from the assembled sequences.

Consensus sequence C will generally be longer than initial sequence S. Its electronic Northern Blot will accordingly deviate from that for S. A repeated Fisher test decides whether the alternative hypothesis of deviation from a uniform expression in the two libraries can be maintained. If this is the case, an attempt is made to lengthen C in the same way as S. This iteration is continued with consensus sequences $C_i$ (i: iteration index) obtained in each case until the alternative hypothesis is rejected (if $H_0$ Exit; truncation criterion I) or until automatic lengthening is no longer possible (while $C_i > C_{i-1}$; truncation criterion II).

In the case of truncation criterion II, with the consensus sequence present after the last iteration, a complete or roughly complete sequence of a gene which can be related to cancer with high statistical certainty is acquired.

Analogously to the above-described examples, it was possible to find from uterus tumor tissue the nucleic acid sequences described in Table I.

Furthermore, for the individual nucleic acid sequences, it was possible to determine the peptide sequences (ORF's) that are listed in Table II, in which no peptide can be assigned to a few nucleic acid sequences and more than one peptide can be assigned to some nucleic acid sequences. As already mentioned above, both the determined nucleic acid sequences and the peptide sequences assigned to the nucleic acid sequences are the subject of this invention.

EXAMPLE 4

Mapping of Nucleic Acid Sequences on the Human Genome

Human genes were mapped using the Stanford G3 Hybrid Panel (Stewart et al., 1997), which is marketed by Research Genetics, Huntsville, Ala. This panel consists of 83 different genomic DNAs of human-hamster hybrid cell lines and allows resolution of 500 kilobases. The hybrid cell lines were obtained by fusion of irradiated diploid human cells with cells of the Chinese hamster. The retention pattern of the human chromosome fragments is determined by means of gene-specific primers in a polymerase chain reaction and is analyzed using software available from the Stanford RH server (http://www.stanford.edu/RH/rhserver_form2.html).

This program determines the STS marker that is nearest to the desired gene. The corresponding cytogenetic band was determined using the "Mapview" program of the Genome Database (GDB), (http://gdbwww.dkfz-heidelberg.de).

In addition to mapping of genes on the human chromosome set by various experimental methods, it is possible to determine the location of genes on this by biocomputer methods. To do this, the known program e-PCR was used (Schuler GD (1998) Electronic PCR: Bridging the Gap between Genome Mapping and Genome Sequencing. Trends Biotechnol 16: 456–459, Schuler GD (1997). Sequence Mapping by Electronic PCR. Genome Res. 7: 541–550). The database used here no longer corresponds to the one cited in the literature, but is a further development which includes data from the public database RHdb (http://www.ebi.ac.uk/RHdb/-index.html). Analogously to the mapping by the hybrid panels, the results were evaluated with the above-mentioned software and the software of the Whitehead Institute (http://carbon.wi.mit.edu:8000/cgi-bin/contig/rhmapper.pl).

References to the modules:

Pfam: Protein families database of alignments and HMMs (pfam@sanger.ac.uk)

PROSITE: The PROSITE database, its status in 1999. Nucleic Acids Res. 27: 215–219 (http://www.expasy.ch/sprot/prosite.html)

TABLE I

Col. 1 - Sequence ID No.:
Col. 2 - Expression in the endometrial tumor:
Col. 3 - Function
Col. 4 - Modules
Col. 5 - Length of the applied sequence in bases
Col. 6 - Cytogenetic localization
Col. 7 - Next marker
[Key to Table I:]
[Col. 2:]
[Seq. ID Nos. 1–62] erhöht = elevated
[Col. 3:]
[Seq. ID Nos.: 1, 7–15, 78–126, 136] unbekannt = unknown
[Seq. ID Nos.: 3, 4, 38, 67–72] Homolog zu . . . = homologous to . . .
[Seq. ID Nos.: 531–555] Verlängerung von Seq. ID No. . . . = Lengthening of Seq. ID No. . . .

| Sequenz ID No.: | Expression im Endometrium Tumor: | Funktion | Module | Länge der angemeldeten Sequenz in Basen | Cytogenetische Lokalisation | nächster Marker |
|---|---|---|---|---|---|---|
| 1 | erhöht | unbekannt | | 1046 | 2p24–2p21 | D2S174–D2S390 |
| 2 | erhöht | Mouse mammary tumor virus proviral envelope gene Polymerase protein | 2x "CSD" | 373 | | |
| 3 | erhöht | Homolog zu Human protein kinase C-binding protein RACK17 | | 1571 | 1q32.1 | D1S477–D1S504 |
| 4 | erhöht | Homolog zu Human mRNA for KIAA0079 | | 1789 | 10q21.3–q22.2 | D10S537–D10S218 |
| 5 | erhöht | Caenorhabditis elegans cosmid T23B12 | "BTB" | 2361 | | |
| 6 | erhöht | Caenorhabditis elegans cosmid C01A2 | | 1638 | 20q13.32–q13.33 | D20S100–D20S173 |
| 7 | erhöht | unbekannt | | 1034 | 12q12 | D12S1589–D12S85 |
| 8 | erhöht | unbekannt | | 947 | 17p11.2–p12 | AFMa126yd5 |
| 9 | erhöht | unbekannt | | 497 | | |
| 10 | erhöht | unbekannt | | 269 | | |
| 11 | erhöht | unbekannt | | 1717 | | |
| 12 | erhöht | unbekannt | "zf-C3HC4" | 1419 | | |
| 13 | erhöht | unbekannt | | 671 | 2q37.3 | D2S2704 |
| 14 | erhöht | unbekannt | | 524 | | |
| 15 | erhöht | unbekannt | | 345 | | |
| 16 | erhöht | rGSTK1-1 = glutahione S-transferase subunit 13 | | 1060 | 7q33–7q36.1 | WI-9353 |
| 17 | erhöht | Rattus norvegicus neuritin | | 1721 | 6p23–p25.1 | D6S1617–D6S1674 |
| 18 | erhöht | Rattus norvegicus cytosolic NADP-dependent isocitrate dehydrogenase | "isodh" | 2367 | 2q34 | WI-1247 |
| 19 | erhöht | Rat unr mRNA for unr protein with unknown function | 2x "CSD" | 1321 | 1p13.3–1q11 | D1S418–D1S252 |

TABLE I-continued

| | | | | | | |
|---|---|---|---|---|---|---|
| 20 | erhöht | Rat prostatic binding protein polypeptide c1 | | 384 | | |
| 21 | erhöht | Rat GTP-binding protein (ral B) | | 367 | | |
| 22 | erhöht | R. norvegicus mRNA for TRAP-complex gamma subunit | | 2621 | 3q24–q25.2 | D3S1570 |
| 23 | erhöht | P. sativum mRNA for Cop1 protein | 2x "G-beta" | 2019 | 1q23.3–q24.3 | D1S242–D1S416 |
| 24 | erhöht | P. falciparum pfmdr1 gene | | 1866 | 18q12.1–q12.3 | AFM164ya9 |
| 25 | erhöht | ORF 5' of ECLF2 . . . ECRF3 = G protein-coupled receptor homolog | | 1189 | | |
| 26 | erhöht | O. cuniculus lambda-crystallin mRNA | "3HCDH" | 1418 | | |
| 27 | erhöht | Mus musculus flotillin | | 814 | | |
| 28 | erhöht | Mouse glycerol-3-phosphate acyltransferase | | 3039 | 10q25.1–q25.2 | D10S1465 |
| 29 | erhöht | Mouse clathrin-associated protein (AP47) | "Adap_comp_sub" | 1448 | | |
| 30 | erhöht | Lycopersicon esculentum biotin-containing subunit of methylcrotonyl-CoA carboxylase | "CPSase_L_chain", "biotin_req_enzy" | 1394 | | |
| 31 | erhöht | Leucine aminopeptidase, bovine | "Peptidase_M17" | 734 | | |
| 32 | erhöht | Klebsiella pneumoniae possible RNA helicase (deaD) | 2x "DEAD" | 692 | | |
| 33 | erhöht | Human mammaglobin Homolog | "Uteroglobin" | 517 | | |
| 34 | erhöht | Human DNA sequence from PAC 138A5 on chromosome X | | 322 | | |
| 35 | erhöht | Human DNA sequence from clone 230G1 | | 1559 | | |
| 36 | erhöht | Human DNA sequence from clone 217C2 | | 1072 | | |
| 37 | erhöht | Human Cosmid Clone 26a1 | "RhoGAP" | 454 | 22.q11.21–q11.23 | D22S420–D22S446 |
| 38 | erhöht | Homolog zu Human chromosome 3p21.1 gene sequence | | 700 | 3p21.1 | |
| 39 | erhöht | Homo sapiens DNA from chromosome 19-cosmid f21246 | | 914 | | |
| 40 | erhöht | H. sapiens mRNA for Ptg-1 protein | | 1669 | 17q21.31–q21.33 | D17S791–D17S797 |
| 41 | erhöht | H. sapiens CpG island DNA genomic Mse1 fragment | | 355 | | |
| 42 | erhöht | H. sapiens (TL5) mRNA from LNCaP cell line | | 2628 | 3q24 | D3S3413 |
| 43 | erhöht | Genomic sequence from Human 9q34 | | 2535 | 9q34.11–q34.13 | D9S179–D9S164 |
| 44 | erhöht | Drosophila melanogaster misato gene | "MYB_3" | 805 | 1q21.2 | D1S305–D1S506 |
| 45 | erhöht | Chicken mRNA for vitellogenin I | | 1279 | | |
| 46 | erhöht | Caenorhabditis elegans DNA from clone F31D4 | | 1923 | | |
| 47 | erhöht | Caenorhabditis elegans cosmid ZK863 | | 706 | | |
| 48 | erhöht | Caenorhabditis elegans cosmid ZK863 | | 749 | | |
| 49 | erhöht | Caenorhabditis elegans cosmid ZK596 | | 857 | 10q26.13 | D10S212 |
| 50 | erhöht | Caenorhabditis elegans cosmid T26A5 | | 268 | | |
| 51 | erhöht | Caenorhabditis elegans cosmid T21G5 | | 297 | | |
| 52 | erhöht | Caenorhabditis elegans cosmid F56D5 | | 590 | | |
| 53 | erhöht | Caenorhabditis elegans cosmid F25D7 | | 1714 | | |
| 54 | erhöht | Caenorhabditis elegans cosmid F08C6 | | 1340 | | |
| 55 | erhöht | C. botulinum bont (partial) and ntnh genes | | 765 | 3q24–q23 | D3S3409 |
| 56 | erhöht | Bovine mRNA fragment for 40 kDa subunit of mitochondrial NADH:ubiquinone oxidoreductase (EC 1.6.5.3) | "complex 1_4 9Kd" | 1647 | | |
| 57 | erhöht | Bos taurus (clone pTKD7) dopamine and cyclic AMP-regulated neuronal phosphonprotein (DARPP-32) | | 1166 | | |
| 58 | erhöht | A. thaliana mRNA for RNA helicase | | 487 | | |
| 59 | erhöht | A. thaliana glycine-rich protein (clone atGRP-4) | | 1630 | 5q23.3–q31.1 | D5S396–D5S2119 |
| 60 | erhöht | Saccharomyces cerevisiae Grd19p (GRD19) | 2x "PX"; "BEM_DOMAIN" | 1272 | 6q21 | AFMa191wd1 |
| 61 | erhöht | Saccharomyces cerevisiae chromosome XII cosmid 9328 | 2x "DEAD"; "helicase_C" | 1914 | 7p12.3—p13 | D7S667–D7S2427 |
| 62 | erhöht | S. pombe chromosome I cosmid c13D6 | | 608 | | |
| 63 | | Rattus norvegicus RNA helicase with arginine-serine-rich domain | | 2674 | 17q21.31–q22 | D17S797–D17S788 |
| 64 | | Rattus norvegicus matrilysin (MMP-7) mRNA | | 326 | | |
| 65 | | Rattus norvegicus Diphor-1 | 2x "PDZ" | 888 | 1q12 | D1S2669–D1S498 |
| 66 | | Human herpesvirus-7 (HHV7) JI, G protein-coupled receptor (GCR) | | 202 | | |
| 67 | | Homolog zu Human synapsin I (SYN1) | | 1225 | 1p22.3–p31.1 | WI-3099 |
| 68 | | Homolog zu Human PAX3 gene | | 1093 | | |
| 69 | | Homolog zu Human multiple exostosis 2 (EXT2) | | 309 | 1p21.3–p22.1 | D1S2166 |
| 70 | | Homolog zu Homo sapiens integrin variant beta4E (ITGB4) | | 380 | | |
| 71 | | Homolog zu Homo sapiens hCPE-R mRNA for CPE-receptor | | 1253 | | |

TABLE I-continued

| | | | | | |
|---|---|---|---|---|---|
| 72 | Homolog zu *H. sapiens* mRNA for deoxyguanosine kinase | | 439 | | |
| 73 | *Caenorhabditis elegans* cosmid Y48E1B | | 1252 | 4p11–q12 | D4S1619–D4S1600 |
| 74 | *Caenorhabditis elegans* cosmid T21D12 | "WW_DOMAIN_2" | 695 | | |
| 75 | *Caenorhabditis elegans* cosmid R107 | | 2514 | 13q33.3–q34 | D13S261–D13S293 |
| 76 | *Caenorhabditis elegans* cosmid M04C9 | | 274 | | |
| 77 | Bovine opsin | "7tm_1" | 449 | | |
| 78 | unbekannt | | 346 | | |
| 79 | unbekannt | | 1329 | | |
| 80 | unbekannt | | 805 | | |
| 81 | unbekannt | | 420 | | |
| 82 | unbekannt | | 2143 | 9q21.32–q22.1 | D9S264–D9S257 |
| 83 | unbekannt | | 450 | | |
| 84 | unbekannt | | 408 | 17q23.1–q23.2 | D17S1680 |
| 85 | unbekannt | | 311 | | |
| 86 | unbekannt | | 487 | | |
| 87 | unbekannt | | 1902 | 11p12–p13 | WI-6150 |
| 88 | unbekannt | | 1048 | 1q42.11–q43 | WI-9317 |
| 89 | unbekannt | | 804 | | |
| 90 | unbekannt | | 581 | | |
| 91 | unbekannt | | 2042 | | |
| 92 | unbekannt | | 430 | | |
| 93 | unbekannt | | 592 | | |
| 94 | unbekannt | | 674 | | |
| 95 | unbekannt | | 324 | | |
| 96 | unbekannt | | 709 | 5p15.33 | D5S1954 |
| 97 | unbekannt | | 592 | | |
| 98 | unbekannt | | 1948 | 16p13.2—p12.3 | D16S499 |
| 99 | unbekannt | | 483 | | |
| 100 | unbekannt | | 437 | | |
| 101 | unbekannt | | 359 | | |
| 102 | unbekannt | | 501 | | |
| 103 | unbekannt | | 1102 | 1q23.1–q23.2 | D1S445–D1S431 |
| 104 | unbekannt | | 306 | | |
| 105 | unbekannt | | 2042 | | |
| 106 | unbekannt | | 320 | | |
| 107 | unbekannt | | 506 | | |
| 108 | unbekannt | | 1276 | | |
| 109 | unbekannt | | 373 | | |
| 110 | unbekannt | TPR_REPEAT" | 492 | | |
| 111 | unbekannt | | 1678 | 6q21 | D6S278–D6S302 |
| 112 | unbekannt | | 866 | 9q22.1–q22.2 | D9S1841–D9S196 |
| 113 | unbekannt | | 1434 | 18q12.1–q12.3 | D18S1124–D18S468 |
| 114 | unbekannt | | 914 | 7q32.3 | D7S686–D7S530 |
| 115 | unbekannt | | 685 | 8p12–p11.23 | D8S1821–D8S255 |
| 116 | unbekannt | | 2646 | | |
| 117 | unbekannt | | 2667 | | |
| 118 | unbekannt | | 544 | | |
| 119 | unbekannt | | 1340 | 18p11.21 | D18S471–D18S464 |
| 120 | unbekannt | | 2376 | | |
| 121 | unbekannt | | 225 | | |
| 122 | unbekannt | | 1967 | 6q22.33–q23.1 | D6S292–D6S1699 |
| 123 | unbekannt | | 612 | | |
| 124 | unbekannt | | 1183 | 2q32.3–q34 | D2S315–D2S2237 |
| 125 | unbekannt | | 891 | 4q28.1–q31.1 | |
| 126 | unbekannt | | 482 | | |
| 127 | Human triosephosphate isomerase mRNA | | 610 | | |
| 128 | Human ras inhibitor mRNA | | 2072 | 9q33.3–q34.11 | |
| 129 | Human R kappa B | | 980 | | |
| 130 | Human putative interferon-related protein (SM15) | | 192 | | |
| 131 | Human protein trafficking protein (S31iii125) | 2x "EMP24_GP25L" | 1092 | 14q32.2–14q32.33 | WI-9179 |
| 132 | Human protein kinase C-binding protein RACK7 | | 1523 | 20q13.13–q13.2 | D20S957 |
| 133 | Human gene for histone H1(0) | "linker_histone" | 2241 | 22q13.1 | |
| 134 | Human cathepsin B proteinase | "Cys-protease" | 631 | | |
| 135 | *Homo sapiens* cathepsin B mRNA | "Cys-protease" | 980 | | |
| 136 | unbekannt | | 2238 | 14q24.1–14q24.3 | D14S277 |
| 137 | *H. sapiens* XG mRNA | | 398 | | |
| 138 | *H. sapiens* mRNA for RAB7 protein | ras | 1084 | 7q21.3–q22.1 | D7S652 |
| 139 | *H. sapiens* mRNA for pyrroline 5-carboxylate synthetase | | 1259 | | |

TABLE I-continued

| | | | | | |
|---|---|---|---|---|---|
| 140 | H. sapiens mRNA for beta-1,4-galactosyl-transferase | | 1938 | 1q22–q23.1 | |
| 141 | H. sapiens IL-13Ra | | 1874 | Xq23 | |
| 531 | Verlängerung von Seq. ID No. 19 | 2x "CSD" | 1708 | 1p13.3–1q11 | D1S418–D1S252 |
| 532 | Verlängerung von Seq. ID No. 23 | 2x "G-beta" | 2128 | 1q23.3–q24.3 | D1S242–D1S416 |
| 533 | Verlängerung von Seq. ID No. 25 | | 2640 | | |
| 534 | Verlängerung von Seq. ID No. 32 | 2x "DEAD" | 1245 | | |
| 535 | Verlängerung von Seq. ID No. 34 | | 822 | | |
| 536 | Verlängerung von Seq. ID No. 43 | | 2703 | 9q34.11–q34.13 | D9S179–D9S164 |
| 537 | Verlängerung von Seq. ID No. 44 | "MYB_3" | 2664 | 1q21.2 | D1S305–D1S506 |
| 538 | Verlängerung von Seq. ID No. 52 | | 3888 | | |
| 539 | Verlängerung von Seq. ID No. 54 | | 3304 | | |
| 540 | Verlängerung von Seq. ID No. 55 | | 863 | 3q24–q23 | D3S3409 |
| 541 | Verlängerung von Seq. ID No. 59 | | 1962 | 5q23.3–q31.1 | D5S396–D5S2119 |
| 542 | Verlängerung von Seq. ID No. 60 | 2x "PX"; "BEM_DOMAIN" | 1772 | 6q21 | AFMa191wd1 |
| 543 | Verlängerung von Seq. ID No. 65 | 2x "PDZ" | 1009 | 1q12 | D1S2669–D1S498 |
| 544 | Verlängerung von Seq. ID No. 69 | | 2834 | 1p21.3–p22.1 | D1S2166 |
| 545 | Verlängerung von Seq. ID No. 82 | | 2319 | 9q21.32–q22.1 | D9S264–D9S257 |
| 546 | Verlängerung von Seq. ID No. 84 | | 2456 | 17q23.1–q23.2 | D17S1680 |
| 547 | Verlängerung von Seq. ID No. 87 | | 2218 | 11p12–p13 | WI-6150 |
| 548 | Verlängerung von Seq. ID No. 88 | | 2196 | 1q42.11–q43 | WI-9317 |
| 549 | Verlängerung von Seq. ID No. 93 | | 701 | | |
| 550 | Verlängerung von Seq. ID No. 98 | | 2214 | 16p13.2–p12.3 | D16S499 |
| 551 | Verlängerung von Seq. ID No. 108 | | 1434 | | |
| 552 | Verlängerung von Seq. ID No. 111 | | 2434 | 6q21 | D6S278–D6S302 |
| 554 | Verlängerung von Seq. ID No. 114 | | 1457 | 7q32.3 | D7S686–D7S530 |
| 555 | Verlängerung von Seq. ID No. 126 | | 741 | | |

TABLE II

| DNA Sequences Seq. ID. No. DNA-Sequenzen Seq. ID. No. | Peptide Sequences (ORF's) Seq. ID. No. Peptid-Sequenzen (ORF's) Seq. ID. No. |
|---|---|
| 1 | 142 |
| | 143 |
| | 144 |
| 2 | 145 |
| | 146 |
| | 147 |
| 3 | 148 |
| | 149 |
| | 150 |
| 4 | 151 |
| | 152 |
| | 153 |
| 5 | 154 |
| | 155 |
| | 156 |
| 6 | 157 |
| | 158 |
| | 159 |
| 7 | 160 |
| | 161 |
| | 162 |
| 8 | 163 |
| | 164 |
| | 165 |
| 9 | 166 |
| | 167 |
| | 168 |
| 10 | 169 |
| | 170 |
| | 171 |
| 11 | 172 |
| | 173 |
| | 174 |
| 12 | 175 |
| 12 | 176 |
| | 177 |
| 13 | 178 |
| | 179 |
| 14 | 180 |
| | 181 |
| | 182 |
| 15 | 183 |
| | 184 |
| | 185 |
| | 186 |
| | 187 |
| 16 | 188 |
| | 189 |
| | 190 |
| 17 | 191 |
| | 192 |
| | 193 |
| 18 | 194 |
| | 195 |
| | 196 |
| 19 | 197 |
| | 198 |
| | 199 |
| 20 | 200 |
| | 201 |
| | 202 |
| 21 | 203 |
| | 204 |
| 22 | 205 |
| | 206 |
| 23 | 207 |
| | 208 |
| | 209 |
| | 210 |
| 24 | 211 |
| 24 | 212 |
| | 213 |
| 25 | 214 |
| | 215 |
| | 216 |
| 26 | 217 |
| | 218 |
| | 219 |

TABLE II-continued

| DNA Sequences Seq. ID. No. | Peptide Sequences (ORF's) Seq. ID. No. |
|---|---|
| 27 | 220 |
|  | 221 |
|  | 222 |
| 28 | 223 |
|  | 224 |
|  | 225 |
| 29 | 226 |
|  | 227 |
|  | 228 |
| 30 | 229 |
|  | 230 |
|  | 231 |
| 31 | 232 |
|  | 233 |
|  | 234 |
| 32 | 235 |
|  | 236 |
|  | 237 |
| 33 | 238 |
|  | 239 |
|  | 240 |
| 34 | 241 |
|  | 242 |
|  | 243 |
| 35 | 244 |
|  | 245 |
|  | 246 |
|  | 247 |
| 36 | 248 |
|  | 249 |
| 37 | 250 |
|  | 251 |
|  | 252 |
| 38 | 253 |
|  | 254 |
|  | 255 |
| 39 | 256 |
|  | 257 |
|  | 258 |
| 40 | 259 |
|  | 260 |
|  | 261 |
| 41 | 262 |
|  | 263 |
|  | 264 |
| 42 | 265 |
|  | 266 |
|  | 267 |
| 43 | 268 |
|  | 269 |
|  | 270 |
| 44 | 271 |
|  | 272 |
|  | 273 |
| 45 | 274 |
|  | 275 |
|  | 276 |
| 46 | 277 |
|  | 278 |
|  | 279 |
| 47 | 280 |
|  | 281 |
|  | 282 |
|  | 283 |
| 48 | 284 |
|  | 285 |
| 49 | 286 |
|  | 287 |
|  | 288 |
| 50 | 289 |
|  | 290 |
|  | 291 |
|  | 292 |
| 51 | 293 |
|  | 294 |
|  | 295 |
| 52 | 296 |
|  | 297 |
|  | 298 |
| 53 | 299 |
|  | 300 |
|  | 301 |
| 54 | 302 |
|  | 303 |
|  | 304 |
| 55 | 305 |
|  | 306 |
|  | 307 |
| 56 | 308 |
|  | 309 |
|  | 310 |
| 57 | 311 |
|  | 312 |
|  | 313 |
| 58 | 314 |
|  | 315 |
|  | 316 |
| 59 | 317 |
|  | 318 |
|  | 319 |
| 60 | 320 |
|  | 321 |
|  | 322 |
| 61 | 323 |
|  | 324 |
|  | 325 |
| 62 | 326 |
|  | 327 |
|  | 328 |
| 63 | 329 |
|  | 330 |
|  | 331 |
| 64 | 332 |
|  | 333 |
|  | 334 |
|  | 335 |
| 65 | 336 |
|  | 337 |
|  | 338 |
| 66 | 339 |
|  | 340 |
|  | 341 |
| 67 | 342 |
|  | 343 |
|  | 344 |
| 68 | 345 |
|  | 346 |
|  | 347 |
| 69 | 348 |
|  | 349 |
|  | 350 |
| 70 | 351 |
|  | 352 |
|  | 353 |
| 71 | 354 |
|  | 355 |
|  | 356 |
| 72 | 357 |
|  | 358 |
|  | 359 |
|  | 360 |
| 73 | 361 |
|  | 362 |
|  | 363 |
| 74 | 364 |
|  | 365 |
|  | 366 |
| 75 | 367 |

TABLE II-continued

| DNA Sequences Seq. ID. No. DNA-Sequenzen Seq. ID. No. | Peptide Sequences (ORF's) Seq. ID. No. Peptid-Sequenzen (ORF's) Seq. ID. No. |
|---|---|
|  | 368 |
|  | 369 |
| 76 | 370 |
|  | 371 |
|  | 372 |
| 77 | 373 |
|  | 374 |
|  | 375 |
| 78 | 376 |
|  | 377 |
|  | 378 |
| 79 | 379 |
|  | 380 |
|  | 380 |
|  | 381 |
| 80 | 382 |
|  | 383 |
|  | 384 |
| 81 | 385 |
|  | 386 |
|  | 387 |
| 82 | 388 |
|  | 389 |
|  | 390 |
| 83 | 391 |
|  | 392 |
|  | 393 |
| 84 | 394 |
|  | 395 |
| 85 | 396 |
|  | 397 |
|  | 398 |
| 86 | 399 |
|  | 400 |
|  | 401 |
|  | 402 |
| 87 | 403 |
|  | 404 |
|  | 405 |
|  | 406 |
| 88 | 407 |
|  | 408 |
|  | 409 |
| 89 | 410 |
|  | 411 |
|  | 412 |
| 90 | 413 |
|  | 414 |
|  | 415 |
| 91 | 416 |
|  | 417 |
|  | 418 |
| 92 | 419 |
|  | 420 |
|  | 421 |
|  | 422 |
| 93 | 423 |
|  | 424 |
|  | 425 |
|  | 426 |
| 94 | 427 |
|  | 428 |
| 95 | 429 |
|  | 430 |
|  | 431 |
|  | 432 |
| 96 | 433 |
|  | 434 |
|  | 435 |
| 97 | 436 |
|  | 437 |
|  | 438 |
| 98 | 439 |
|  | 440 |
|  | 441 |
| 99 | 442 |
|  | 443 |
|  | 444 |
| 100 | 445 |
|  | 446 |
|  | 447 |
| 101 | 448 |
|  | 449 |
|  | 450 |
| 102 | 451 |
|  | 452 |
|  | 453 |
| 103 | 454 |
|  | 455 |
|  | 456 |
| 104 | 457 |
|  | 458 |
|  | 459 |
|  | 460 |
| 105 | 461 |
|  | 462 |
|  | 463 |
| 106 | 464 |
|  | 465 |
| 107 | 466 |
|  | 467 |
|  | 468 |
|  | 469 |
| 108 | 470 |
|  | 471 |
|  | 472 |
| 109 | 473 |
|  | 474 |
|  | 475 |
| 110 | 476 |
|  | 477 |
|  | 478 |
| 111 | 479 |
|  | 480 |
|  | 481 |
| 112 | 482 |
|  | 483 |
|  | 484 |
|  | 485 |
| 113 | 486 |
|  | 487 |
|  | 488 |
| 114 | 489 |
|  | 490 |
|  | 491 |
| 115 | 492 |
|  | 493 |
|  | 494 |
|  | 495 |
| 116 | 496 |
|  | 497 |
|  | 498 |
| 117 | 499 |
|  | 500 |
|  | 501 |
| 118 | 502 |
|  | 503 |
|  | 504 |
| 119 | 505 |
|  | 506 |
|  | 507 |
| 120 | 508 |
|  | 509 |
|  | 510 |
| 121 | 511 |
|  | 512 |
|  | 513 |
| 122 | 514 |

TABLE II-continued

| DNA Sequences Seq. ID. No. DNA-Sequenzen Seq. ID. No. | Peptide Sequences (ORF's) Seq. ID. No. Peptid-Sequenzen (ORF's) Seq. ID. No. |
|---|---|
|  | 515 |
|  | 516 |
| 123 | 517 |
|  | 518 |
|  | 519 |
| 124 | 520 |
|  | 521 |
|  | 522 |
| 125 | 523 |
|  | 524 |
|  | 525 |
| 126 | 526 |
|  | 527 |
|  | 528 |
| 531 | 561 |
|  | 562 |
|  | 563 |
| 532 | 564 |
|  | 565 |
|  | 566 |
| 533 | 567 |
|  | 568 |
|  | 569 |
| 534 | 570 |
|  | 571 |
|  | 572 |
| 535 | 573 |
|  | 574 |
|  | 575 |
| 536 | 577 |
|  | 578 |
| 537 | 579 |
|  | 580 |
|  | 581 |
| 538 | 582 |
|  | 583 |
|  | 584 |
| 539 | 585 |
|  | 586 |
|  | 587 |
| 540 | 588 |
|  | 589 |
|  | 590 |
| 541 | 591 |
|  | 592 |
|  | 593 |
| 542 | 594 |
|  | 595 |
|  | 596 |
| 543 | 597 |
|  | 598 |
|  | 599 |
| 544 | 600 |
|  | 601 |
|  | 602 |
| 545 | 603 |
|  | 604 |
|  | 605 |
| 546 | 606 |
|  | 607 |
|  | 608 |
| 547 | 609 |
|  | 610 |
|  | 611 |
| 548 | 612 |
|  | 613 |
|  | 614 |
| 549 | 615 |
|  | 616 |
|  | 617 |
| 550 | 618 |
|  | 619 |
|  | 620 |
| 551 | 621 |
|  | 622 |
|  | 623 |
| 552 | 624 |
|  | 625 |
| 554 | 630 |
|  | 631 |
|  | 632 |
| 555 | 633 |
|  | 634 |
|  | 635 |

The inventive nucleic acid sequences Seq. ID No. 1 to Seq. ID No. 141 of the determined candidate genes and the determined amino acid sequences Seq. ID Nos. 142–528 are described in the following sequence protocol.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6620923B1). An electronic copy of the "Sequence Listing" will also be available from the USPTO upon request and payment of the fee set forth in 37 CFR 1.19(b)(3).

What is claimed is:

1. An isolated nucleic acid consisting of SEQ ID NO: 33.

* * * * *